US007622481B2

(12) United States Patent
Axten et al.

(10) Patent No.: US 7,622,481 B2
(45) Date of Patent: Nov. 24, 2009

(54) ANTIBACTERIAL COMPOUNDS

(75) Inventors: Jeffrey Michael Axten, Collegeville, PA (US); Robert A Daines, Collegeville, PA (US); David Thomas Davies, Harlow (GB); Timothy Francis Gallagher, Collegeville, PA (US); Graham Elgin Jones, Harlow (GB); William Henry Miller, Collegeville, PA (US); Neil David Pearson, Harlow (GB); Israil Pendrak, Collegeville, PA (US)

(73) Assignee: Glaxo Group Limited, Brentford, Middlesex (GB)

( * ) Notice: Subject to any disclaimer, the term of this patent is extended or adjusted under 35 U.S.C. 154(b) by 435 days.

(21) Appl. No.: 10/518,653

(22) PCT Filed: Jun. 25, 2003

(86) PCT No.: PCT/EP03/06756

§ 371 (c)(1),
(2), (4) Date: Apr. 3, 2006

(87) PCT Pub. No.: WO2004/002992

PCT Pub. Date: Jan. 8, 2004

(65) Prior Publication Data

US 2006/0189604 A1    Aug. 24, 2006

(51) Int. Cl.
C07D 513/04    (2006.01)
C07D 471/04    (2006.01)
A61K 31/542    (2006.01)
A61K 31/4375    (2006.01)

(52) U.S. Cl. .................................... 514/300; 546/122
(58) Field of Classification Search ................. 514/300; 546/122
See application file for complete search history.

(56) References Cited

U.S. PATENT DOCUMENTS

| 6,403,610 | B1 | 6/2002 | Mallcron et al. | 514/314 |
|---|---|---|---|---|
| 6,602,882 | B1 | 8/2003 | Davies et al. | 514/300 |
| 6,602,884 | B2 | 8/2003 | Bacque et al. | 514/314 |
| 6,603,005 | B2 | 8/2003 | Bacque et al. | 546/176 |
| 6,806,277 | B2 | 10/2004 | Bacque et al. | 514/314 |
| 6,815,547 | B2 | 11/2004 | Bacque et al. | 546/174 |
| 6,841,562 | B2 | 1/2005 | Bacqueet al. | 514/314 |
| 6,903,217 | B2 | 6/2005 | Bacque et al. | 546/180 |
| 6,939,970 | B2 | 9/2005 | Bourget et al. | 546/174 |
| 6,962,917 | B2 * | 11/2005 | Davies et al. | 514/248 |
| 7,109,213 | B2 | 9/2006 | Daines et al. | 514/312 |
| 7,141,564 | B2 * | 11/2006 | Brooks et al. | 514/224.2 |
| 7,223,776 | B2 | 5/2007 | Surivet et al. | 514/313 |
| 7,232,832 | B2 | 6/2007 | Axten et al. | 514/300 |
| 7,232,833 | B2 | 6/2007 | Bigot et al. | 514/314 |
| 7,232,834 | B2 | 6/2007 | Bacque et al. | 514/315 |
| 7,312,212 | B2 | 12/2007 | Daines et al. | 514/228.2 |
| 7,491,714 | B2 | 2/2009 | Axten et al. | 514/211.09 |
| 2006/0058287 | A1 | 3/2006 | Axten et al. | 514/224.2 |
| 2006/0205719 | A1 | 9/2006 | Hubscherlen et al. | 514/230.5 |
| 2007/0004710 | A1 | 1/2007 | Axten et al. | 514/224.2 |

FOREIGN PATENT DOCUMENTS

| WO | WO99/37635 | 7/1999 |
|---|---|---|
| WO | WO00/21948 | 4/2000 |
| WO | WO00/21952 | 4/2000 |
| WO | WO00/43383 | 7/2000 |
| WO | WO 02/78748 | 12/2000 |
| WO | WO01/07432 A2 | 2/2001 |
| WO | WO01/07433 A2 | 2/2001 |
| WO | WO01/25227 A2 | 4/2001 |
| WO | WO 02/08224 | 1/2002 |
| WO | WO02/24684 | 3/2002 |
| WO | WO02/40474 | 5/2002 |
| WO | WO02/50040 A1 | 6/2002 |
| WO | WO02/50061 A1 | 6/2002 |
| WO | WO 02/056882 | 7/2002 |
| WO | WO02/072572 A1 | 9/2002 |
| WO | WO 02/096907 | 12/2002 |
| WO | WO 03/010138 | 2/2003 |
| WO | WO03/064421 | 8/2003 |
| WO | WO03/064431 | 8/2003 |
| WO | WO03/087098 | 10/2003 |
| WO | WO2004/002490 | 1/2004 |
| WO | WO2004/011454 A2 | 2/2004 |
| WO | WO2004/014361 A1 | 2/2004 |
| WO | WO2004/024712 A1 | 3/2004 |
| WO | WO2004/024713 A1 | 3/2004 |
| WO | WO2004/035569 | 4/2004 |
| WO | WO2004/041210 A2 | 5/2004 |
| WO | WO2004/050036 A2 | 6/2004 |
| WO | WO2004/058144 A2 | 7/2004 |
| WO | WO2004/060886 | 7/2004 |
| WO | WO2004/087145 A2 | 10/2004 |
| WO | WO2004/087647 | 10/2004 |
| WO | WO2004/089947 | 10/2004 |
| WO | WO2004/096982 A2 | 11/2004 |

OTHER PUBLICATIONS

Werrnuth, et al., The Practise of Medicinal Chemistry, pp. 203-237 XP002190259 (1996).

* cited by examiner

Primary Examiner—Kahsay T Habte
(74) Attorney, Agent, or Firm—Reid S. Willis; John Lemanowicz

(57) ABSTRACT

Cyclohexane and cyclohexene derivatives and pharmaceutically acceptable derivatives thereof useful in methods of treatment of bacterial infections in mammals, particularly man.

24 Claims, No Drawings

ANTIBACTERIAL COMPOUNDS

This invention relates to novel compounds, compositions containing them and their use as antibacterials.

WO099/37635, WO00/21948, WO00/21952, WO00/43383, WO00/78748, WO01/07433, WO01/07432, WO02/08224, WO02/24684, WO02/50040, WO02/56882, WO02/96907, PCT/EP02/05708, WO03010138, WO01/25227 and WO0207572 disclose quinoline and naphthyridine derivatives having antibacterial activity.

This invention provides a compound of formula (I) or a pharmaceutically acceptable derivative thereof:

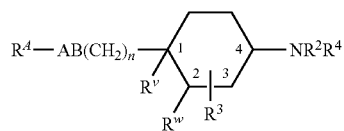

(I)

wherein:

$R^v$ and $R^w$ are hydrogen or $R^v$ and $R^w$ together are a bond;

$R^A$ is an optionally substituted bicyclic carbocyclic or heterocyclic ring system of structure:

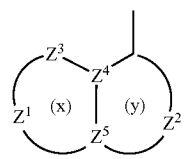

containing 0-3 heteroatoms in each ring in which:
at least one of rings (x) and (y) is aromatic;
one of $Z^4$ and $Z^5$ is C or N and the other is C;
$Z^3$ is N, $NR^{13}$, O, $S(O)_x$, CO, $CR^1$ or $CR^1R^{1a}$;
$Z^1$ and $Z^2$ are independantly a 2 or 3 atom linker group each atom of which is independently selected from N, $NR^{13}$, O, $S(O)_x$, CO, $CR^1$ and $CR^1R^{1a}$;

such that each ring is independently substituted with 0-3 groups $R^1$ and/or $R^{1a}$;

$R^1$ and $R^{1a}$ are independently selected from hydrogen; hydroxy; $(C_{1-6})$ alkoxy optionally substituted by $(C_{1-6})$ alkoxy, amino, piperidyl, guanidino or amidino any of which is optionally N-substituted by one or two $(C_{1-6})$alkyl, acyl or $(C_{1-6})$alkylsulphonyl groups, $CONH_2$, hydroxy, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkoxy-substituted $(C_{1-6})$alkyl; hydroxy $(C_{1-6})$alkyl; halogen; $(C_{1-6})$alkyl; $(C_{1-6})$alkylthio; trifluromethyl; trifluoromethoxy; cyano; carboxy; nitro; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups, or when $Z^3$ and the adjacent atom are $CR^1$ and $CR^{1a}$, $R^1$ and $R^{1a}$ may together represent $(C_{1-2})$alkylenedioxy, provided that $R^1$ and $R^{1a}$, on the same carbon atom are not both optionally substituted hydroxy or amino;

provided that (i) when $R^A$ is optionally substituted quinolin-4-yl:
it is unsubstituted in the 6-position; or
it is substituted by at least one hydroxy $(C_{1-6})$alkyl, cyano or carboxy group at the 2-, 5-, 6-, 7- or 8-position; or it is substituted by at least one trifluoromethoxy group; or $R^3$ is halogen;

(ii) when $R^A$ is optionally substituted quinazolin-4-yl, cinnolin-4-yl, 1,5-naphthyridin-4-yl, 1,7-naphthyridin-4-yl or 1,8-naphthyridin-4-yl:
it is substituted by at least one hydroxy $(C_{1-6})$alkyl, cyano or carboxy group at the 2-, 5-, 6-, 7- or 8-position as available; or
it is substituted by at least one trifluoromethoxy group; or $R^3$ is halogen;

$R^2$ is hydrogen, or $(C_{1-4})$alkyl or $(C_{2-4})$alkenyl optionally substituted with 1 to 3 groups selected from:

amino optionally substituted by one or two $(C_{1-4})$alkyl groups; carboxy; $(C_{1-4})$alkoxycarbonyl; $(C_{1-4})$alkylcarbonyl; $(C_{2-4})$alkenyloxycarbonyl; $(C_{2-4})$alkenylcarbonyl; aminocarbonyl wherein the amino group is optionally substituted by hydroxy, $(C_{1-4})$alkyl, hydroxy$(C_{1-4})$alkyl, aminocarbonyl $(C_{1-4})$alkyl, $(C_{2-4})$alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$alkenyloxycarbonyl or $(C_{2-4})$alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; halogen; $(C_{1-4})$alkylthio; trifluoromethyl; hydroxy optionally substituted by $(C_{1-4})$alkyl, $(C_{2-4})$alkenyl, $(C_{1-4})$alkoxycarbonyl, $(C_{1-4})$alkylcarbonyl, $(C_{2-4})$alkenyloxycarbonyl, $(C_{2-4})$alkenylcarbonyl; oxo; $(C_{1-4})$ alkylsulphonyl; $(C_{2-4})$alkenylsulphonyl; or $(C_{1-4})$aminosulphonyl wherein the amino group is optionally substituted by $(C_{1-4})$alkyl or $(C_{2-4})$alkenyl;

$R^3$ is hydrogen; or when $R^v$ and $R^w$ are a bond, $R^3$ is in the 2-, 3- or 4-position and when $R^v$ and $R^w$ are not a bond, $R^3$ is in the 1-, 2-, 3- or 4-position and $R^3$ is:

carboxy, $(C_{1-6})$alkoxycarbonyl; aminocarbonyl wherein the amino group is optionally substituted by hydroxy, $(C_{1-6})$alkyl, hydroxy$(C_{1-6})$alkyl, aminocarbonyl$(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy $(C_{1-6})$alkyl, aminocarbonyl$(C_{1-6})$alkyl or $(C_{2-6})$alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $(C_{1-4})$alkyl or ethenyl optionally substituted with any of the groups listed above for $R^3$ and/or 0 to 2 groups $R^{12}$ independently selected from:

halogen; $(C_{1-6})$alkylthio; trifluoromethyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$ alkyl, hydroxy$(C_{1-6})$alkyl, aminocarbonyl$(C_{1-6})$alkyl, $(C_{2-6})$ alkenyl, $(C_{1-6})$alkoxycarbonyl, $(C_{1-6})$alkylcarbonyl, $(C_{2-6})$ alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$ alkyl or $(C_{2-6})$alkenyl; or hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$ alkyl, $(C_{2-6})$alkenyl, $(C_{1-6})$alkylcarbonyl or $(C_{2-6})$alkenylcarbonyl; or amino optionally mono- or disubstituted by $(C_{1-6})$alkoxycarbonyl, $(C_{1-6})$alkylcarbonyl, $(C_{2-6})$alkenyloxycarbonyl, $(C_{2-6})$ alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; or halogen;

provided that when $R^3$ is in the 4-position it is not optionally substituted hydroxyl or amino or halogen;

in addition when $R^3$ is disubstituted with a hydroxy or amino containing substituent and a carboxy containing substituent these may optionally together form a cyclic ester or amide linkage, respectively;

$R^{10}$ is selected from $(C_{1-4})$alkyl and $(C_{2-4})$alkenyl either of which may be optionally, substituted by a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$ alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; $(C_{1-6})$alkylsulphonyl; trifluoromethylsulphonyl; $(C_{2-6})$alkenylsulphonyl; $(C_{1-6})$alkoxycarbonyl; $(C_{1-6})$ alkylcarbonyl; $(C_{2-6})$alkenyloxycarbonyl; and $(C_{2-6})$alkenylcarbonyl;

$R^4$ is a group —$CH_2$—$R^5{}_1$ in which $R^5{}_1$ is selected from:

$(C_{4-8})$alkyl; hydroxy$(C_{4-8})$alkyl; $(C_{1-4})$alkoxy$(C_4$-g)alkyl; $(C_{1-4})$alkanoyloxy$(C_{4-8})$alkyl; $(C_{3-9})$cycloalkyl$(C_{4-9})$alkyl; hydroxy-, $(C_{1-6})$alkoxy- or $(C_{1-6})$alkanoyloxy-$(C_{3-8})$cycloalkyl$(C_{4-9})$alkyl; cyano$(C_{4-8})$alkyl; $(C_{4-8})$alkenyl; $(C_{4-9})$ alkynyl; tetrahydrofuryl; mono- or di-$(C_{1-6})$alkylamino$(C_{4-8})$ alkyl; acylamino$(C_{4-9})$alkyl; $(C_{1-6})$alkyl- or acylaminocarbonyl$(C_{4-8})$alkyl; mono- or di-$(C_{1-6})$alkylamino (hydroxy) $(C_4$-g)alkyl; or $R^4$ is a group —U—$R^5{}_2$ where $R^5{}_2$ is an optionally substituted bicyclic carbocyclic or heterocyclic ring system (A):

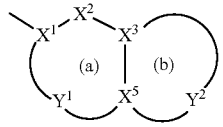

(A)

containing up to four heteroatoms in each ring in which
  at least one of rings (a) and (b) is aromatic;
  $X^1$ is C or N when part of an aromatic ring or $CR^{14}$ when part of a non aromatic ring;
  $X^2$ is N, $NR^{13}$, O, $S(O)_x$, CO or $CR^{14}$ when part of an aromatic or non-aromatic ring or may in addition be $CR^{14}R^{15}$ when part of a non aromatic ring;
  $X^3$ and $X^5$ are independently N or C;
  $Y^1$ is a 0 to 4 atom liner group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring,
  $Y^2$ is a 2 to 6 atom linker group, each atom of $Y^2$ being independently selected from N, $NR^{13}$, O, $S(O)_x$, CO and $CR^{14}$ when part of an aromatic or non-aromatic ring or may additionally be $CR^{14}R^{15}$ when part of a non aromatic ring;
  each of $R^{14}$ and $R^{15}$ is independently selected from: H; $(C_{1-4})$alkylthio; halo; carboxy$(C_{1-4})$alkyl; halo$(C_{1-4})$oxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$ alkoxycarbonyl$(C_{1-4})$alkyl; hydroxy; hydroxy$(C_{1-4})$alkyl; mercapto$(C_{1-4})$alkyl; $(C_{1-4})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; aryl; aryl$(C_{1-4})$alkyl; aryl$(C_{1-4})$alkoxy;
  each $R^{13}$ is independently H; trifluoromethyl; $(C_{1-4})$alkyl optionally substituted by hydroxy, carboxy, $(C_{1-6})$alkoxycarbonyl, $(C_{1-6})$alkoxy, $(C_{1-6})$alkylthio, halo or trifluoromethyl; $(C_{2-4})$alkenyl; aryl; aryl $(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$ alkenylcarbonyl, $(C_{1-4})$alkyl or $(C_{2-4})$alkenyl and optionally further substituted by $(C_{1-4})$alkyl or $(C_{2-4})$alkenyl;
  each x is independently 0, 1 or 2;

U is CO, $SO_2$ or $CH_2$; or $R^4$ is a group —$X^{1a}$—$X^{2a}$—$X^{3a}$—$X^{4a}$ in which:
  $X^{1a}$ is $CH_2$, CO or $SO_2$;
  $X^{2a}$ is $CR^{14a}R^{15a}$;
  $X^{3a}$ is $NR^{13a}$, O, S, $SO_2$ or $CR^{14a}R^{15a}$; wherein:
    each of $R^{14a}$ and $R^{15a}$ is independently selected from the groups listed above for $R^{14}$ and $R^{15}$, provided that $R^{14a}$ and $R^{15a}$ on the same carbon atom are not both selected from optionally substituted hydroxy and optionally substituted amino; or
    $R^{14a}$ and $R^{15a}$ together represent oxo;
    $R^{13a}$ is hydrogen; trifluoromethyl; $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl or $(C_{2-6})$ alkenyl and optionally further substituted by $(C_{1-6})$alkyl or $(C_{2-6})$alkenyl; or
    two $R^{14a}$ groups or an $R^{13a}$ and an $R^{14a}$ group on adjacent atoms together represent a bond and the remaining $R^{13a}$, $R^{14a}$ and $R^{15a}$ groups are as above defined; or
    two $R^{14a}$ groups and two $R^{15a}$ groups on adjacent atoms together represent bonds such that $X^{2a}$ and $X^{3a}$ is triple bonded;
  $X^{4a}$ is phenyl or C or N linked monocyclic aromatic 5- or 6-membered heterocycle containing up to four heteroatoms selected from O, S and N and: optionally C-substituted by up to three groups selected from $(C_{1-4})$alkylthio; halo; carboxy $(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; aryl, aryl$(C_{1-4})$alkyl or aryl $(C_{1-4})$alkoxy; and optionally N substituted by trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; aryl; aryl$(C_{1-4})$alkyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl;

n is 0 or 1 and AB is $NR^{11}CO$, $CONR^{11}$, $CO—CR^8R^9$, $CR^6R^7$-CO, $O—CR^8R^9$, $CR^6R^7$-O, $NHR^{11}—CR^8R^9$, $CR^6R^7$-$NHR^{11}$, $NR^{11}SO_2$, $CR^6R^7—SO_2$ or $CR^6R^7$-$CR^8R^9$, provided that when $R^v$ and $R^w$ are a bond and n=0, B is not $NR^{11}$, O or $SO_2$, or n is 0 and AB is NH—CO—NH or NH—CO—O and $R^v/R^w$ are not a bond;

or n is 0 and AB is $CR^6R^7SO_2NR^2$, $CR^6R^7CONR^2$ or $CR^6R^7CH_2NR^2$ and $R^v/R^w$ are not a bond;

provided that $R^6$ and $R^7$, and $R^8$ and $R^9$ are not both optionally substituted hydroxy or amino;

and wherein:

each of $R^6$, $R^7$, $R^8$ and $R^9$ is independently selected from: H; $(C_{1-6})$alkoxy; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl;

or $R^6$ and $R^8$ together represent a bond and $R^7$ and $R^9$ are as above defined;

and each $R^{11}$ is independently H; trifluoromethyl; $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl;

or where one of $R^3$ and $R^6$, $R^7$, $R^8$ or $R^9$ contains a carboxy group and the other contains a hydroxy or amino group they may together form a cyclic ester or amide linkage or where $R^3$ contains a carboxy group and A or B is NH they may be condensed to form a cyclic amide.

The invention also provides the use of a compound of formula (I) or a pharmaceutically acceptable derivative thereof in the manufacture of a medicament for use in the treatment of bacterial infections in mammals.

The invention also provides a pharmaceutical composition, in particular for use in the treatment of bacterial infections in mammals, comprising a compound of formula (I), or a pharmaceutically acceptable derivative thereof, and a pharmaceutically acceptable carrier.

The invention further provides a method of treatment of bacterial infections in mammals, particularly in man, which method comprises the administration to a mammal in need of such treatment of an effective amount of a a compound of formula (I), or a pharmaceutically acceptable derivative thereof.

Preferably $Z^2$ is three atoms long.

Preferably $Z^4$ and $Z^5$ are both carbon.

Preferably $Z^1$ is three atoms long with carbon joined to $Z^3$ and with $R^1$ on the carbon atom joined to $Z^3$.

In one preferred aspect, $R^4$ is aromatic and ring (y) is fused benzene. Preferably (x) is 6-membered containing one or two nitrogen atoms, the remainder being carbon. Most preferably $Z^3$ is nitrogen and the remainder are carbon or $Z^1$ is =CH—CH=N— (N attached to $Z^5$).

In another preferred aspect, ring (y) is fused pyridin-4-yl ($Z^2$ is three atoms long, the atom attached to $Z^5$ in $Z^2$ is nitrogen and the remainder and $Z^4$ and $Z^5$ are carbon), $Z^1$ is two or three atoms long and $Z^3$ is a heteroatom such as O or S.

Suitable examples of rings $R^4$ include optionally substituted isoquinolin-5-yl, quinolin-8-yl, thieno[3,2-b]pyridin-7-yl, 2,3-dihydro-[1,4]dioxino[2,3-b]pyridin-8-yl, quinoxalin-5-yl, isoquinolin-8-yl, [1,6]-naphthyridin-4-yl, 1,2,3,4-tetrahydroquinoxalin-5-yl and 1,2-dihydroisoquinoline-8-yl. Most preferably $R^4$ is optionally 2-substituted-quinolin-8-yl or optionally 3-substituted-quinoxalin-5-yl.

$R^{13}$ in rings (x) and (y) is preferably H or $(C_{1-6})$alkyl.

When $R^1$ or $R^{1a}$ is substituted alkoxy it is preferably $(C_{2-6})$alkoxy substitituted by optionally N-substituted amino, or $(C_{1-6})$alkoxy substituted by piperidyl. Suitable examples of $R^1$ alkoxy include methoxy, trifluoromethoxy, n-propyloxy, i-butyloxy, aminoethyloxy, aminopropyloxy, aminobutyloxy, aminopentyloxy, guanidinopropyloxy, piperidin-4-ylmethyloxy or 2-aminocarbonylprop-2-oxy.

Preferably $R^1$ and $R^{1a}$ are independently hydrogen, $(C_{1-4})$alkoxy, $(C_{1-4})$alkylthio, $(C_{1-4})$alkyl, amino$(C_{3-5})$alkyloxy, nitro, cyano, carboxy, hydroxymethyl or halogen; more preferably hydrogen, methoxy, methyl, cyano, halogen or amino$(C_{3-5})$alkyloxy.

Ring $R^A$ is preferably substituted by one group $R^1$. Most preferably $R^1$ is H, methoxy, methyl, cyano or halogen and $R^{1a}$ is H. Halogen is preferably chloro or fluoro.

$R^2$ is preferably hydrogen; $(C_{1-4})$alkyl substituted with carboxy, optionally substituted hydroxy, optionally substituted aminocarbonyl, optionally substituted amino or $(C_{1-4})$alkoxycarbonyl; or $(C_{2-4})$alkenyl substituted with $(C_{1-4})$alkoxycarbonyl or carboxy. More preferred groups for $R^2$ are hydrogen, carboxymethyl, hydroxyethyl, aminocarbonylmethyl, ethoxycarbonylmethyl, ethoxycarbonylallyl and carboxyallyl, most preferably hydrogen.

Preferred examples of $R^3$ include hydrogen; optionally substituted hydroxy; optionally substituted amino; halogen; $(C_{1-4})$ alkyl; ethenyl; optionally substituted 1-hydroxy-$(C_{1-4})$alkyl; optionally substituted aminocarbonyl; carboxy$(C_{1-4})$alkyl; optionally substituted aminocarbonyl$(C_{1-4})$alkyl; cyano$(C_{1-4})$alkyl; optionally substituted 2-oxo-oxazolidinyl and optionally substituted 2-oxo-oxazolidinyl$(C_{1-4}$alkyl). More preferred $R^3$ groups are hydrogen; $CONH_2$; 1-hydroxyalkyl e.g. $CH_2OH$, $CH(OH)CH_2CN$; $CH_2CO_2H$; $CH_2CONH_2$; —$CONHCH_2CONH_2$; 1,2-dihydroxyalkyl e.g. $CH(OH)CH_2OH$; $CH_2CN$; 2-oxo-oxazolidin-5-yl; 2-oxo-oxazolidin-5-yl$(C_{1-4}$alkyl); optionally substituted hydroxy; optionally substituted amino; and halogen, in particular fluoro. Most preferably $R^3$ is hydrogen, fluoro or hydroxy, and if fluoro or hydroxy, most preferably substituted in the 1-or 3-position. $R^3$ hydroxy in the 3-position preferably is trans to $NR^2R^4$ and has R stereochemistry or is cis to $NR^2R^4$ and has S stereochemistry.

When $R^3$ and $R^6$, $R^7$, $R^8$ or $R^9$ together form a cyclic ester or amide linkage, it is preferred that the resulting ring is 5-7 membered. It is further preferred that the group A or B which does not form the ester or amide linkage is $CH_2$.

When A is CH(OH) the R-stereochemistry is preferred.

Preferably A is NH, $NCH_3$, $CH_2$, CHOH, $CH(NH_2)$, C(Me)(OH) or CH(Me).

Preferably B is $CH_2$ or CO.

Preferably n=0.

Preferably, when $R^v$ and $R^w$ are not a bond and n=1 or $AB(CH_2)_n$ is NHCONH or NHCOO, $AB(CH_2)_n$ and $NR^2R^4$ are cis.

Preferably, when $R^v$ and $R^w$ are not a bond and n=0 and AB is not NHCONH or NHCOO, $AB(CH_2)_n$ and $NR^2R^4$ are trans.

More preferably:

n is 0 and either A and B are both $CH_2$, A is CHOH, $CH_2$ and B is $CH_2$ or A is NH and B is CO.

Most preferably AB is NHCO.

Preferably $R^{11}$ is hydrogen or $(C_{1-4})$alkyl e.g. methyl, more preferably hydrogen.

When $R^4$ is $CH_2R^5_1$, preferably $R^5_1$ is $(C_{6-8})$alkyl.

When $R^4$ is a group —$X^{1a}$—$X^{2a}$—$X^{3a}$—$X^{4a}$:

$X^{1a}$ is preferably $CH_2$.

$X^{2a}$ is preferably $CH_2$ or together with $X^{3a}$ forms a CH=CH or C≡C group.

$X^{3a}$ is preferably $CH_2$, O, S or NH, or together with $X^{2a}$ forms a CH=CH or C≡C group.

Preferred linker groups —$X^{1a}$—$X^{2a}$—$X^{3a}$— include —$(CH_2)_2$—O—, —$(CH_2)_2$—S—, —$CH_2$—CH=CH—, —$(CH_2)_3$—, —$(CH_2)_2$—NH— or —$CH_2$CONH—.

Monocyclic aromatic heterocyclic groups for $X^{4a}$ include pyridyl, pyrazinyl, pyrimidinyl, triazolyl, tetrazolyl, thienyl, isoimidazolyl, thiazolyl, furanyl and imidazolyl, 2H-pyridazone, 1H-pyrid-2-one. Preferred aromatic heterocyclic groups include pyrid-2-yl, pyrid-3-yl, thiazole-2-yl, pyrimidin-2-yl, pyrimidin-5-yl and fur-2-yl.

Preferred substituents on heterocyclic $X^{4a}$ include halo especially fluoro, trifluoromethyl and nitro.

Preferred substituents on phenyl $X^{4a}$ include halo, especially fluoro, nitro, cyano, trifluoromethyl, methyl, methoxycarbonyl and methylcarbonylamino.

Preferably $X^{4a}$ is 2-pyridyl, 3-fluorophenyl, 3,5-difluorophenyl or thiazol-2-yl.

Preferably $R^4$ is —U—$R^5_2$.

The group —U— is preferably —$CH_2$—.

Preferably $R^5_2$ is an aromatic heterocyclic ring (A) having 8-11 ring atoms including 2-4 heteroatoms of which at least one is N or $NR^{13}$ in which preferably $Y^2$ contains 2-3 heteroatoms, one of which is S and 1-2 are N, with one N bonded to $X^3$.

Alternatively and preferably the heterocyclic ring (A) has ring (a) aromatic selected from optionally substituted benzo and pyrido and ring (b) non-aromatic and $Y^2$ has 3-5 atoms, more preferably 4 atoms, including a heteroatom bonded to $X^5$ selected from O, S or $NR^{13}$, where $R^{13}$ is other than hydrogen, and NHCO bonded via N to $X^3$, or O bonded to $X^3$. The ring (a) preferably contains aromatic nitrogen, and more preferably ring (a) is pyridine. Examples of rings (A) include optionally substituted:

(a) and (b) Aromatic 1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl, benzimidazol-2-yl, benzo[1,2,3]-thiadiazol-5-yl, benzo[1,2,5]-oxadiazol-5-yl, benzofur-2-yl, benzothiazol-2-yl, benzo[b]thiophen-2-yl, benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, indan-2-yl, naphthalen-2-yl, 1,3-dioxo-isoindol-2yl, benzimidazol-2-yl, benzothiophen-2-yl, 1H-benzotriazol-5-yl, 1H-indol-5-yl, 3H-benzooxazol-2-one-6-yl, 3H-benzooxazol-2-thione-6-yl, 3H-benzothiazol-2-one-5-yl, 3H-quinazolin-4-one-2-yl, 3H-quinazolin-4-one-6-yl, 4-oxo-4H-pyrido[1,2-a]pyrimidin-3-yl, benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-a]pyridazin-2-yl, imidazo[1,2-b]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimdin-4-one-2-yl, pyrido[1,2-a]pyrimidin-4-one-3-yl, quinazolin-2-yl, quinoxalin-6-yl, thiazolo[3,2-a]pyrimidin-5-one-7-yl, thiazolo[5,4-b]pyridin-2-yl, thieno[3,2-b]pyridin-6-yl, thiazolo[5,4-b]pyridin-6-yl, 4-oxo-4H-pyrido[1,2-a]pyrimidin-2-yl, 1-oxo-1,2-dihydro-isoquinolin-3-yl, thiazolo[4,5-b]pyridin-5-yl, [1,2,3]thiadiazolo[5,4-b]pyridin-6-yl, 2H-isoquinolin-1-one-3-yl (a) is Non Aromatic (2S)-2,3-dihydro-1H-indol-2-yl, (2S)-2,3-dihydro-benzo[1,4]dioxine-2-yl, 3-(R,S)-3,4-dihydro-2H-benzo[1,4]thiazin-3-yl, 3-(R)-2,3-dihydro-[1,4]dioxino[2,3-b]pyridin-3-yl, 3-(S)-2,3-dihydro-[1,4]dioxino[2,3-b]pyridin-3-yl, 2,3-dihydro-benzo[1,4]dioxan-2-yl, 3-substituted-3H-quinazolin-4-one-2-yl, (b) is Non Aromatic 1,1,3-trioxo-1,2,3,4-tetrahydro-1 $1^6$-benzo[1,4]thiazin-6-yl, benzo[1,3]dioxol-5-yl, 4H-benzo[1,4]oxazin-3-one-6-yl, 2,3-dihydro-benzo[1,4]dioxin-6-yl, 2-oxo-2,3-dihydro-benzooxazol-6-yl, 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydro-benzo[b][1,4]thiazepine-7-yl, 5-oxo-2,3-dihydro-5H-thiazolo[3,2-a]pyrimidin-6-yl, benzo[1,3]dioxol-5-yl, 2-oxo-2,3-dihydro-1H-pyrido[2,3-b][1,4]thiazin-7-yl, 2-oxo-2,3-dihydro-1H-pyrido[3,4-b][1,4]thiazin-7-yl, 3-oxo-3,4-dihydro-2H-pyrido[3,2-b)][1,4]thiazin-6-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, 6,7-dihydro-[1,4]dioxino[2,3-d]pyrimidin-2-yl, 3-oxo-3,4-dihydro-2H-pyrido[3,2-b][1,4]oxazin-6-yl, 2-oxo-2,3-dihydro-1H-pyrido[3,4-b][1,4]oxazin-7-yl, 2-oxo-2,3-dihydro-1H-pyrido[2,3-b][1,4]oxazin-7-yl, 6-oxo-6,7-dihydro-5H-8-thia-1,2,5-triaza-naphthalen-3-yl, 3,4-dihydro-2H-benzo[1,4]oxazin-6-yl, 3,4-dihydro-2H-benzo[1,4]thiazin-6-yl, 3-substituted-3H-benzooxazol-2-one-6-yl, 3-substituted-3H-benzooxazole-2-thione-6-yl, 3-substituted-3H-benzothiazol-2-one-6-yl, 2,3-dihydro-1H-pyrido[2,3-b][1,4]thiazin-7-yl, 3,4-dihydro-2H-benzo[1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl, 2-oxo-3,4-dihydro-1H-[1,8]naphthyridin-6-yl, 3,4-dihydro-2H-pyrido[3,2-b][1,4]thiazin-6-yl.

$R^{13}$ is preferably H if in ring (a) or in addition $(C_{1-4})$alkyl such as methyl or isopropyl when in ring (b). More preferably, in ring (b) $R^{13}$ is H when $NR^{13}$ is bonded to $X^3$ and $(C_{1-4})$alkyl when $NR^{13}$ is bonded to $X^5$.

$R^{14}$ and $R^{15}$ are preferably independently selected from hydrogen, halo, hydroxy, $(C_{1-4})$ alkyl, $(C_{1-4})$alkoxy, trifluoromethoxy, nitro, cyano, aryl$(C_{1-4})$alkoxy and $(C_{1-4})$alkylsulphonyl.

More preferably $R^{15}$ is hydrogen.

More preferably each $R^{14}$ is selected from hydrogen, chloro, fluoro, hydroxy, methyl, methoxy, trifluoromethoxy, benzyloxy, nitro, cyano and methylsulphonyl. Most preferably $R^{14}$ is selected from hydrogen, hydroxy, fluorine or nitro. Preferably 0-3 groups $R^{14}$ are substituents other than hydrogen.

Most preferably $R^{14}$ and $R^{15}$ are each H.

Most preferred groups $R^5{}_2$ include:

[1,2,3]thiadiazolo[5,4-b]pyridin-6-yl
1H-Pyrrolo[2,3-b]pyridin-2-yl
2,3-Dihydro-[1,4]dioxino[2,3-b]pyridin-6-yl
2,3-Dihydro-[1,4]dioxino[2,3-b]pyridin-7-yl
2,3-Dihydro-[1,4]dioxino[2,3-c]pyridin-7-yl
2,3-dihydro-benzo[1,4]dioxin-6-yl
2-oxo-2,3-dihydro-1H-pyrido[2,3-b][1,4]oxazin-7-yl
2-oxo-2,3-dihydro-1H-pyrido[2,3-b][1,4]thiazin-7-yl
3,4-dihydro-2H-benzo[1,4]oxazin-6-yl
3-Methyl-2-oxo-2,3-dihydro-benzooxazol-6-yl
3-oxo-3,4-dihydro-2H-benzo[1,4]oxazin-6-yl
3-oxo-3,4-dihydro-2H-pyrido[3,2-b][1,4]oxazin-6-yl
3-oxo-3,4-dihydro-2H-benzo[1,4]thiazin-6-yl (4H-benzo[1,4]thiazin-3-one-6-yl)
4-oxo-4H-pyrido[1,2-a]pyrimidin-2-yl
6-nitro-benzo[1,3]dioxol-5-yl
7-fluoro-3-oxo-3,4-dihydro-2H-benzo[1,4]oxazin-6-yl
8-Hydroxy-1-oxo-1,2-dihydro-isoquinolin-3-yl
8-hydroxyquinolin-2-yl
benzo[1,2,3]thiadiazol-5-yl
benzo[1,2,5]thiadiazol-5-yl
benzothiazol-5-yl
thiazolo-[5,4-b]pyridin-6-yl
3-oxo-3,4-dihydro-2H-pyrido[3,2-b][1,4]thiazin-6-yl
7-chloro-3-oxo-3,4-dihydro-2H-pyrido[3,2-b][1,4]thiazin-6-yl
7-fluoro-3-oxo-3,4-dihydro-2H-pyrido[3,2-b][1,4]thiazin-6-yl
2-oxo-2,3-dihydro-1H-pyrido[3,4-b][1,4]thiazin-7-yl especially 3-oxo-3,4-dihydro-2H-pyrido[3,2-b][1,4]oxazin-6-yl
3-oxo-3,4-dihydro-2H-pyrido[3,2-b][1,4]thiazin-6-yl
7-chloro-3-oxo-3,4-dihydro-2H-pyrido[3,2-b][1,4]thiazin-6-yl
7-fluoro-3-oxo-3,4-dihydro-2H-pyrido[3,2-b][1,4]thiazin-6-yl
2,3-dihydro-[1,4]dioxino[2,3-c]pyridin-7-yl.

When used herein, the term "alkyl" includes groups having straight and branched chains, for instance, methyl, ethyl, n-propyl, iso-propyl, n-butyl, iso-butyl, sec-butyl, t-butyl, pentyl and hexyl. The term 'alkenyl' should be interpreted accordingly.

Halo or halogen includes fluoro, chloro, bromo and iodo.

Haloalkyl moieties include 1-3 halogen atoms.

Unless otherwise defined, the term 'heterocyclic' as used herein includes aromatic and non-aromatic, single and fused, rings suitably containing up to four hetero-atoms in each ring selected from oxygen, nitrogen and sulphur, which rings may be unsubstituted or C-substituted by, for example, up to three groups selected from $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; optionally substituted aryl, aryl $(C_{1-4})$alkyl or aryl$(C_{1-4})$alkoxy and oxo groups. Each heterocyclic ring suitably has from 4 to 7, preferably 5 or 6, ring atoms. A fused heterocyclic ring system may include carbocyclic rings and need include only one heterocyclic ring. Compounds within the invention containing a heterocyclyl group may occur in two or more tautomeric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; aryl; aryl $(C_{1-4})$alkyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl.

When used herein the term 'aryl', includes phenyl and naphthyl, each optionally substituted with up to five, preferably up to three, groups selected from $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl $(C_{1-4})$alkyl; hydroxy; hydroxy$(C_{1-4})$alkyl; mercapto$(C_{1-4})$ alkyl; $(C_{1-4})$alkoxy; nitro; cyano, carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; phenyl, phenyl$(C_{1-4})$alkyl or phenyl$(C_{1-4})$alkoxy.

The term 'acyl' includes $(C_{1-6})$alkoxycarbonyl, formyl or $(C_{1-6})$ alkylcarbonyl groups.

Most preferred compounds of formula (I) are:

(1R, 3S, 4R)-3-Hydroxy-4-[(3-oxo-3,4-dihydro-2H-pyrido[3,2-b][1,4]oxazin-6-ylmethyl)-amino]-cyclohexanecarboxylic acid (2-cyano-quinolin-8-yl)-amide t-4-[(2,3-Dihydro-[1,4]dioxino[2,3-c]pyridin-7-ylmethyl)-amino]-1-hydroxy-c-cyclohexanecarboxylic acid (2-methylquinolin-8-yl)-amide(1R,3S,4R)-4-[(2,3-Dihydro-[1,4]dioxino[2,3-c]pyridin-7-ylmethyl)-amino]-3-hydroxy-cyclohexanecarboxylic acid (2-cyano-quinolin-8-yl)-amide t-4-[(2,3-Dihydro-[1,4]dioxino[2,3-c]pyridin-7-ylmethyl)-amino]-1-hydroxy-r-cyclohexanecarboxylic acid (2-cyano-quinolin-8-yl)-amide t-[(2,3-Dihydro-[1,4]dioxino[2,3-c]pyridin-7-ylmethyl)-amino]-1-hydroxy-r-cyclohexanecarboxylic acid (3-methoxy-quinoxalin-5-yl)-amide or a pharmaceutically acceptable derivative thereof.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Pharmaceutically acceptable derivatives of the above-mentioned compounds of formula (I) include the free base form or their acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives.

Examples of suitable pharmaceutically acceptable in vivo hydrolysable ester-forming groups include those forming esters which break down readily in the human body to leave the parent acid or its salt. Suitable groups of this type include those of part formulae (i), (ii), (iii), (iv) and (v):

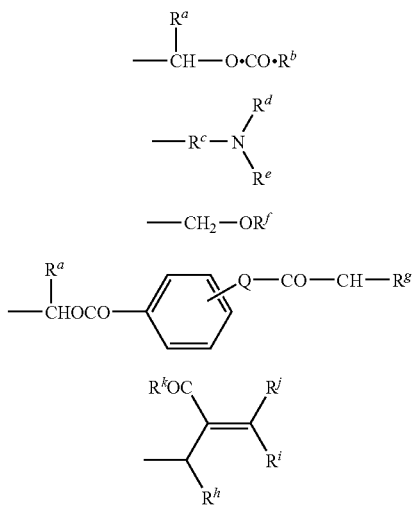

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$(C_{1-6}$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy;

Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; $(C_{1-6})$alkoxycarbonyloxy$(C_{1-6})$alkyl groups, such as ethoxycarbonyloxymethyl, α-ethoxycarbonyloxyethyl and propoxycarbonyloxyethyl; di$(C_{1-6})$alkylamino$(C_{1-6})$alkyl especially di$(C_{1-4})$alkylamino $(C_{1-4})$alkyl groups such as dimethylaminomethyl, dimethylaminoethyl, diethylaminomethyl or diethylaminoethyl; 2-(($C_{1-6})$alkoxycarbonyl)-2-($C_{2-6})$alkenyl groups such as 2-(isobutoxycarbonyl)pent-2-enyl and 2-(ethoxycarbonyl) but-2-enyl; lactone groups such as phthalidyl and dimethoxyphthalidyl.

A further suitable pharmaceutically acceptable in vivo hydrolysable ester-forming group is that of the formula:

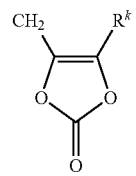

wherein $R^k$ is hydrogen, $C_{1-6}$ alkyl or phenyl.

R is preferably hydrogen.

Certain of the above-mentioned compounds of formula (I) may exist in the form of optical isomers, e.g. diastereoisomers and mixtures of isomers in all ratios, e.g. racemic mixtures. The invention includes all such forms, in particular the pure isomeric forms. For examples the invention includes compound in which an A-B group CH(OH)—CH$_2$ is in either isomeric configuration the R-isomer is preferred. The different isomeric forms may be separated or resolved one from the other by conventional methods, or any given isomer may be obtained by conventional synthetic methods or by stereospecific or asymmetric syntheses.

In a further aspect of the invention there is provided a process for preparing compounds of formula (I), or a pharmaceutically acceptable derivative thereof, which process comprises reacting a compound of formula (IV) with a compound of formula (V):

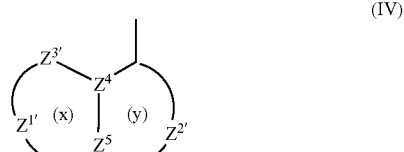

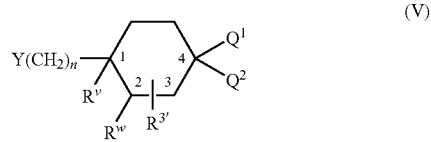

wherein n is as defined in formula (I); $Z^{1'}$, $Z^{2'}$, $Z^{3'}R^{1'}$ and $R^{3'}$ are $Z^1$, $Z^2$, $Z^3$, $R^1$ and $R^3$ as defined in formula (I) or groups convertible thereto; $Z^4$, $Z^5$, $R^v$ and $R^w$ are as defined in formula (I);

$Q^1$ is $NR^{2'}R^{4'}$ or a group convertible thereto wherein $R^{2'}$ and $R^{4'}$ are $R^2$ and $R^4$ as defined in formula (I) or groups convertible thereto and $Q^2$ is H or $R^{3'}$ or $Q^1$ and $Q^2$ together form an optionally protected oxo group;

and X and Y may be the following combinations:
(i) one of X and Y is $CO_2R^y$ and the other is $CH_2CO_2R^x$;
(ii) X is $CHR^6R^7$ and Y is $C(=O)R^9$;
(iii) X is $CR^7=PR^z_3$ and Y is $C(=O)R^9$;
(iv) X is $C(=O)R^7$ and Y is $CR^9=PR^z_3$;
(v) one of Y and X is COW and the other is $NHR^{11'}$, NCO or $NR11'COW$;
(vi) X is $NHR^{11'}$ and Y is $C(=O)R^8$ or X is $C(=O)R^6$ and Y is $NHR^{11'}$;
(vii) X is $NHR^{11'}$ and Y is $CR^8R^9W$;
(viii) X is W or OH and Y is $CH_2OH$;
(ix) X is $NHR^{11'}$ and Y is $SO_2W$;
(x) one of X and Y is $(CH_2)_p$—W and the other is $(CH_2)_q NHR^{11'}$, $(CH_2)_qOH$, $(CH_2)_qSH$ or $(CH_2)_qSCOR^x$ where p+q=1;
(xi) one of X and Y is OH and the other is —CH=$N_2$;
(xii) X is NCO and Y is OH or $NH_2$;
(xiii) X is $CR^6R^7SO_2W$, A'COW, $CR^6=CH_2$ or oxirane and Y is $NHR^{2'}$;
(xiv) X is W and Y is $CONHR^{11}$ or $OCONH_2$
(xv) X is W and Y is —C≡CH followed by hydrogenation of the intermediate —C≡C— group;

in which W is a leaving group, e.g. halo, methanesulphonyloxy, trifluoromethanesulphonyloxy or imidazolyl; $R^x$ and $R^y$ are $(C_{1-6})$alkyl; $R^z$ is aryl or $(C_{1-6})$alkyl; A' and $NR^{11'}$ are A and $NR^{11}$ as defined in formula (I), or groups convertible thereto; and oxirane is:

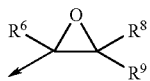

wherein $R^6$, $R^8$ and $R^9$ are as defined in formula (I);

and thereafter optionally or as necessary converting $Q^1$ and $Q^2$ to $NR^{2'}R^{4'}$; converting A', $Z^{1'}$, $Z^{2'}$, $Z^{3'}$, $R^{1'}$, $R^{2'}$, $R^{3'}$, $R^{4'}$ and $NR^{11'}$ to A, $Z^1$, $Z^2$, $Z^3$, $R^1$, $R^2$, $R^3$, $R^4$ and $NR^{11}$; converting A-B to other A-B, interconverting $R^v$, $R^w$, $R^1$, $R^2$, $R^3$ and/or $R^4$, and/or forming a pharmaceutically acceptable derivative thereof.

Process variant (i) initially produces compounds of formula (I) wherein A-B is CO—$CH_2$ or $CH_2$—CO.

Process variant (ii) initially produces compounds of formula (I) wherein A-B is $CR^6R^7$—$CR^9OH$.

Process variant (iii) and (iv) initially produce compounds of formula (I) wherein A-B is $CR^7=CR^9$.

Process variant (v) initially produces compounds of formula (I) where A-B is CO—$NR^{11}$ or $NR^{11}$—CO.

Process variant (vi) initially produces compounds of formula (I) wherein A-B is $NR^{11}$—$CHR^8$. or $CHR^6$—$NHR^{11}$.

Process variant (vii) initially produces compounds of formula (I) wherein A-B is $NR^{11'}$—$CR^8R^9$.

Process variant (viii) initially produces compounds of formula (I) wherein A-B is O—$CH_2$.

Process variant (ix) initially produces compounds where AB is $NR^{11}SO_2$.

Process variant (x) initially produces compounds of formula (I) wherein one of A and B is $CH_2$ and the other is $NHR^{11}$, O or S.

Process variant (xi) initially produces compounds of formula (I) wherein A-B is $OCH_2$ or $CH_2O$.

Process variant (xii) initially produces compounds where AB is NH—CO—NH or NH—CO—O.

Process variant (xiii) initially produces compounds where n is 0 and AB is $CR^6R^7SO_2NR^2$, A'-$CONR^2$ or $CR^6R^7CH_2NR^2$.

Process variant (xiv) produces compounds where AB is $NR^{11}CO$ or NH—CO—O.

Process variant (xv) produces compounds where AB is —$CH_2CH_2$— or CH=CH—.

In process variants (v) and (xiii) (second variant) the reaction is a standard amide or urea formation reaction involving e.g.:

1. Activation of a carboxylic acid (e.g. to an acid chloride, mixed anhydride, active ester, O-acyl-isourea or other species), and treatment with an amine (Ogliaruso, M. A.; Wolfe, J. F. in *The Chemistry of Functional Groups* (Ed. Patai, S.) Suppl. B: *The Chemistry of Acid Derivatives*, Pt. 1 (John Wiley and Sons, 1979), pp 442-8; Beckwith, A. L. J. in *The Chemistry of Functional Groups* (Ed. Patai, S) Suppl. B: *The Chemistry of Amides* (Ed. Zabricky, J) (John Wiley and Sons, 1970), p 73 ff. The acid and amine are preferably reacted in the presence of an activating agent such as 1-(dimethylaminopropyl)-3-ethylcarbodiimide hydrochloride (EDC) or 1-hydroxybenzotriazole (HOBT) or O-(7-azabenzotriazol-1-yl)-N,N,N',N'-tetramethyluronium hexafluorophosphate (HATU); or 2. The specific methods of:

a. in situ conversion of an acid into the amine component by a modified Curtius reaction procedure (Shioiri, T., Murata, M., Hamada, Y., *Chem. Pharm. Bull.* 1987, 35, 2698)

b. in situ conversion of the acid component into the acid chloride under neutral conditions (Villeneuve, G. B.; Chan, T. H., *Tetrahedron. Lett.* 1997, 38, 6489).

A' may be, for example. protected hydroxymethylene.

The process variant (xiii) (third variant) is a standard addition reaction using methods well known to those skilled in the art. The process is preferably carried out in a polar organic solvent e.g. acetonitrile in the presence of an organic base e.g. triethylamine.

In process variant (xiii) (fourth variant) the coupling may be effected in acetonitrile at room temperature in the presence of one equivalent of lithium perchlorate as catalyst (general method of J. E. Chateauneuf et al, *J. Org. Chem., X*, 5939-5942, 1991) or more preferably with ytterbium triflate in dichloromethane. In some cases an elevated temperature such as 40-70° C. may be beneficial. Alternatively, the compound of formula (V) may be treated with a base, such as one equivalent of butyl lithium, and the resulting salt reacted with the oxirane in an inert solvent such as tetrahydrofuran, preferably at an elevated temperature such as 80° C. Use of a chiral epoxide will afford single diastereomers. Alternatively, mixtures of diastereomers may be separated by preparative HPLC or by conventional resolution through crystallisation of salts formed from chiral acids.

The process variant (xii) is a standard urea or carbamate formation reaction from the reaction of an isocyanate with an amine or alcohol and is conducted by methods well known to those skilled in the art (for example see March, J; *Advanced Organic Chemistry, Edition* 3 (John Wiley and Sons, 1985), p802-3). The process is preferably carried out in a polar solvent such as N,N-dimethylformamide.

In process variant (i) the process is two step: firstly a condensation using a base, preferably sodium hydride or alkoxide, sodamide, alkyl lithium or lithium dialkylamide, preferably in an aprotic solvent e.g. ether, THF or benzene; secondly, hydrolysis using an inorganic acid, preferably HCl in aqueous organic solvent at 0-100° C. Analogous routes are described in DE330945, EP31753, EP53964 and H. Sargent, J. Am. Chem. Soc. 68, 2688-2692 (1946). Similar Claisen methodology is described in Soszko et. al., Pr. Kom. Mat. Przyr. Poznan. Tow. Przj. Nauk., (1962), 10, 15.

In process variant (ii) the reaction is carried out in the presence of a base, preferably organometallic or metal hydride e.g. NaH, lithium diisopropylamide or NaOEt, preferably in an aprotic solvent, preferably THF, ether or benzene at −78 to 25° C. (analogous process in Gutswiller et al. (1978) J. Am. Chem. Soc. 100, 576).

In process variants (iii) and (iv) if a base is used it is preferably NaH, KH, an alkyl lithium e.g. BuLi, a metal alkoxide e.g. NaOEt, sodamide or lithium dialkylamide e.g. di-isopropylamide. An analogous method is described in U.S. Pat. No. 3,989,691 and M. Gates et. al. (1970) J. Amer. Chem. Soc., 92, 205, as well as Taylor et al. (1972) JACS 94, 6218.

In process variant (vi) the reaction is a standard reductive alkylation using, e.g., sodium borohydride or sodium triacetoxyborohydride (Gribble, G. W. in *Encyclopedia of Reagents for Organic Synthesis* (Ed. Paquette, L. A.) (John Wiley and Sons, 1995), p 4649).

The process variant (vii) is a standard alkylation reaction well known to those skilled in the art, for example where an alcohol or amine is treated with an alkyl halide in the presence of a base (for example see March, J; *Advanced Organic Chemistry, Edition* 3 (John Wiley and Sons, 1985), p364-366 and p342-343). The process is preferably carried out in a polar solvent such as N,N-dimethylformamide In process variant (xiii) (first variant) the reaction is a standard sulphonamide formation reaction well known to those skilled in the art. This may be e.g. the reaction of a sulphonyl halide with an amine.

In process variant (viii) where X is W such as halogen, methanesulphonyloxy or trifluoromethanesulphonyloxy, the hydroxy group in Y is preferably converted to an OM group where M is an alkali metal by treatment of an alcohol with a base. The base is preferably inorganic such as NaH, lithium diisopropylamide or sodium. Where X is OH, the hydroxy group in Y is activated under Mitsunobu conditions (Fletcher et. al. J Chem Soc. (1995), 623). Alternatively the X=O and Y=CH$_2$OH groups can be reacted directly by activation with 1,3-dicyclohexylcarbodiimide (DCC) (Chem. Berichte 1962, 95, 2997 or Angewante Chemie 1963 75, 377).

In process variant (ix) the reaction is conducted in the presence of an organic base such as triethylamine or pyridine such as described by Fuhrman et. al., J. Amer. Chem. Soc.; 67, 1245, 1945. The X=NR$^{11}$'SO$_2$W or Y=SO$_2$W intermediates can be formed from the requisite amine e.g. by reaction with SO$_2$Cl$_2$ analogously to the procedure described by the same authors Fuhrman et. al., J. Amer. Chem. Soc.; 67, 1245, 1945.

In process variant (x) where one of X and Y contains NHR$^{11}$ the leaving group W is halogen and the reaction is a standard amine formation reaction such as direct alkylation described in (Malpass, J. R., in *Comprehensive Organic Chemistry*, Vol. 2 (Ed. Sutherland, I. O.), p 4 ff.) or aromatic nucleophilic displacement reactions (see references cited in *Comprehensive Organic Chemistry*, Vol. 6, p 946-947 (reaction index); Smith, D. M. in *Comprehensive Organic Chemistry*, Vol. 4 (Ed. Sammes, P. G.) p 20 ff.). This is analogous to the methods described in GB 1177849.

In process variant (x) where one of X and Y contains OH or SH, this is preferably converted to an OM or SM group where M is an alkali metal by treatment of an alcohol, thiol or thioacetate with a base. The base is preferably inorganic such as NaH, lithium diisopropylamide or sodium, or, for SH, metal alkoxide such as sodium methoxide. The X/Y group containing the thioacetate SCOR$^x$ is prepared by treatment of an alcohol or alkyl halide with thioacetic acid or a salt thereof under Mitsunobu conditions. The leaving group V is a halogen. The reaction may be carried out as described in Chapman et. al., J. Chem Soc., (1956), 1563, Gilligan et. al., J. Med. Chem., (1992), 35, 4344, Aloup et. al., J. Med. Chem. (1987), 30, 24, Gilman et al., J.A.C.S. (1949), 71, 3667 and Clinton et al., J.A.C.S. (1948), 70, 491, Barluenga et al., J. Org. Chem. (1987) 52, 5190. Alternatively where X is OH and Y is CH$_2$V, V is a hydroxy group activated under Mitsunobu conditions (Fletcher et. al. J Chem Soc. (1995), 623).

In process variant (xi) the reaction is as described in den Hertzog et. al., recl. Trav. Chim. Pays-Bas, (1950), 69, 700.

In process variant (xiv) the leaving group W is preferably chloro, bromo or trifluoromethylsulphonyl and the reaction is the palladium catalysed process known as the "Buchwald" reaction (J. Yin and S. L. Buchwald, Org. Lett., 2000, 2, 1101).

In process variant (xv) coupling of the acetylene compound (V) with the compound (IV) is accomplished using standard Pd-mediated chemistry, for example using Pd(Ph$_3$P)$_2$Cl$_2$ as the catalyst along with the addition of CuI in a mixture of triethylamine and dimethylformamide. Hydrogenation of the intermediate =C— group is carried out conventionally over a suitable catalyst eg Pd/C, either partially to —CH=CH— or fully to —CH$_2$—CH$_2$—

Reduction of a carbonyl group A or B to CHOH can be readily accomplished using reducing agents well known to those skilled in the art, e.g. sodium borohydride in aqueous ethanol or lithium aluminium hydride in ethereal solution. This is analogous to methods described in EP53964, U.S. Pat. No. 384,556 and J. Gutzwiller et al, *J. Amer. Chem. Soc.*, 1978, 100, 576.

The carbonyl group A or B may be reduced to CH$_2$ by treatment with a reducing agent such as hydrazine in ethylene glycol, at e.g. 130-160° C., in the presence of potassium hydroxide.

Reaction of a carbonyl group A or B with an organometallic reagent yields a group where R$^6$ or R$^8$ is OH and R$^7$ or R$^9$ is alkyl.

A hydroxy group on A or B may be oxidised to a carbonyl group by oxidants well known to those skilled in the art, for example, manganese dioxide, pyridinium chlorochromate or pyridinium dichromate.

A hydroxyalkyl A-B group CHR$^7$CR$^9$OH or CR$^7$(OH)CHR$^9$ may be dehydrated to give the group CR$^7$=CR$^9$ by treatment with an acid anhydride such as acetic anhydride.

Methods for conversion of CR$^7$=CR$^9$ by reduction to CHR$^7$CHR$^9$ are well known to those skilled in the art, for example using hydrogenation over palladium on carbon as catalyst. Methods for conversion of CR$^7$=CR$^9$ to give the A-B group CR$^7$(OH)CHR$^9$ or CHR$^7$CR$^9$OH are well known to those skilled in the art for example by epoxidation and subsequent reduction by metal hydrides, hydration, hydroboration or oxymercuration. Where R$^v$ and R$^w$ together represent a bond it will be appreciated that such conversions may be inappropriate.

An amide carbonyl group may be reduced to the corresponding amine using a reducing agent such as lithium aluminium hydride.

A hydroxy group in A or B may be converted to azido by activation and displacement e.g. under Mitsunobu conditions using hydrazoic acid or by treatment with diphenylphosphorylazide and base, and the azido group in turn may be reduced to amino by hydrogenation.

An example of a group $Q^1$ convertible to $NR^2R^4$ is $NR^{2'}R^{4'}$ or halogen. Halogen may be displaced by an amine $HNR^{2'}R^{4'}$ by a conventional alkylation.

When $Q^1 Q^2$ together form a protected oxo group this may be an acetal such as ethylenedioxy which can subsequently be removed by acid treatment to give a compound of formula (VI):

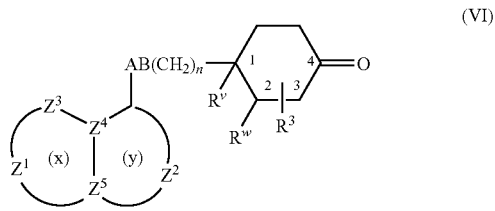

wherein the variables are as described for formula (I)

Intermediates of formula (VI) are novel and as such form part of the invention.

The ketone of formula (VI) is reacted with an amine $HNR^{2'}R^{4'}$ by conventional reductive alkylation as described above for process variant (x).

Other novel intermediates of the invention are compounds of formula (VI:

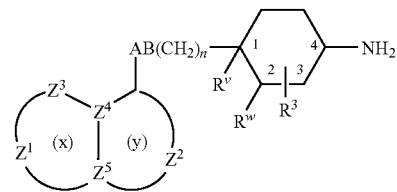

wherein the variables are as described for formula (I).

Examples of groups $Z^{1'}$, $Z^{2'}$ and $Z^{3'}$, are $CR^{1'}$ or $CR^{1'}R^{1a'}$ where $R^{1'}$ and $R^{1a'}$ are groups convertible to $R^1$ and $R^{1a}$. $Z^{1'}$, $Z^{2'}$ and $Z^{3'}$, are preferably $Z^1$, $Z^2$ and $Z^3$.

$R^{1a'}$, $R^{1'}$ and $R^{2'}$ are preferably $R^{1a}$, $R^1$ and $R^2$. $R^{2'}$ is preferably hydrogen. $R^{3'}$ is $R^3$ or more preferably hydrogen, vinyl, alkoxycarbonyl or carboxy. $R^{4'}$ is $R^4$ or more preferably H or an N-protecting group such as t-butoxycarbonyl, benzyloxycarbonyl or 9-fluorenylmethyloxycarbonyl.

Conversions of $R^{1a', R1'}$, $R^{2'}$, $R^{3'}$ and $R^{4'}$ and interconversions of $R^{1a}$, $R^1$, $R^2$, $R^3$ and $R^4$ are conventional. In compounds which contain an optionally substituted hydroxy group, suitable conventional hydroxy protecting groups which may be removed without disrupting the remainder of the molecule include acyl and alkylsilyl groups. N protecting groups are removed by conventional methods.

For example $R^{1'}$ methoxy is convertible to $R^{1'}$ hydroxy by treatment with lithium and diphenylphosphine (general method described in Ireland et. al. (1973) J. Amer. Chem. Soc., 7829) or HBr. Alkylation of the hydroxy group with a suitable alkyl derivative bearing a leaving group such as halide and a protected amino, piperidyl, amidino or guanidino group or group convertible thereto, yields, after conversion/deprotection, $R^1$ alkoxy substituted by optionally N-substituted amino, piperidyl, guanidino or amidino.

$R^3$ alkenyl is convertible to hydroxyalkyl by hydroboration using a suitable reagent such as 9-borabicyclo[3.3.1]nonane, epoxidation and reduction or oxymercuration.

$R^3$ 1,2-dihydroxy can be prepared from $R^{3'}$ alkenyl using osmium tetroxide or other reagents well known to those skilled in the art (see Advanced Organic Chemistry (Ed. March, J.) (John Wiley and Sons, 1985), p 732-737 and refs. cited therein) or epoxidation followed by hydrolysis (see Advanced Organic Chemistry (Ed. March, J.) (John Wiley and Sons, 1985), p 332,333 and refs. cited therein).

$R^3$ vinyl can be chain extended by standard homologation e.g by conversion to hydroxyethyl followed by oxidation to the aldehyde which is then subjected to a Wittig reaction.

Opening an epoxide $R^{3'}$ group with cyanide anion yields a $CH(OH)$—$CH_2CN$ group.

Opening an epoxide-containing $R^3$ group with azide anion yields an azide derivative which can be reduced to the amine. Conversion of the amine to a carbamate is followed by ring closure with base to give the 2-oxo-oxazolidinyl containing $R^3$ group.

Substituents on $R^3$ alkyl or alkenyl may be interconverted by conventional methods, for example hydroxy may be derivatised by esterification, acylation or etherification. Hydroxy groups may be converted to halogen, thiol, alkylthio, azido, alkylcarbonyl, amino, aminocarbonyl, oxo, alkylsulphonyl, alkenylsulphonyl or aminosulphonyl by conversion to a leaving group and substitution by the required group, hydrolysis or oxidation as appropriate or reaction with an activated acid, isocyanate or alkoxyisocyanate. Primary and secondary hydroxy groups can be oxidised to an aldehyde or ketone respectively and alkyated with a suitable agent such as an organometallic reagent to give a secondary or tertiary alcohol as appropriate. A carboxylate group may be converted to an hydroxymethyl group by reduction of an ester of this acid with a suitable reducing agent such as lithium aluminium hydride.

Substituted 2-oxo-oxazolidinyl containing $R^3$ groups may be prepared from the corresponding aldehyde by conventional reaction with a glycine anion equivalent, followed by cyclisation of the resulting amino alcohol (M Grauert et al, Ann Chem (1985) 1817, Rozenberg et al, Angew Chem Int Ed Engl (1994) 33(1) 91). The resulting 2-oxo-oxazolidinyl group contains a carboxy group which can be converted to other $R^{10}$ groups by standard procedures.

Carboxy groups within $R^3$ may be prepared by Jones' oxidation of the corresponding alcohols $CH_2OH$ using chromic acid and sulphuric acid in water/methanol (E. R. H. Jones et al, J.C.S. 1946, 39). Other oxidising agents may be used for this transformation such as sodium periodate catalysed by ruthenium trichloride (G. F. Tutwiler et al, J. Med. Chem., 1987, 30(6), 1094), chromium trioxide-pyridine (G. Just et al, Synth. Commun. 1979, 9(7), 613), potassium permanganate (D. E. Reedich et al, J. Org. Chem., 1985, 50(19), 3535, and pyridinium chlorochromate (D. Askin et al, Tetrahedron Letters, 1988, 29(3), 277.

The carboxy group may alternatively be formed in a two stage process, with an initial oxidation of the alcohol to the corresponding aldehyde using for instance dimethyl sulphoxide activated with oxalyl chloride (N. Cohen et al, J. Am. Chem. Soc., 1983, 105, 3661) or dicyclohexylcarbodiimide (R. M. Wengler, Angew. Chim. Int. Ed. Eng., 1985, 24(2), 77), or oxidation with tetrapropylammonium perruthenate (Ley et al, J. Chem. Soc. Chem Commun., 1987, 1625). The aldehyde may then be separately oxidised to the corresponding acid using oxidising agents such as silver (II) oxide (R. Grigg et al, J. Chem. Soc. Perkin 1, 1983, 1929), potassium permanganate (A. Zurcher, Helv. Chim. Acta., 1987, 70 (7), 1937), sodium periodate catalysed by ruthenium trichloride (T. Sakata et al, Bull. Chem. Soc. Jpn., 1988, 61(6), 2025), pyridinium chlorochromate (R. S. Reddy et al, Synth. Commun., 1988, 18(51), 545) or chromium trioxide (R. M. Coates et al, J. Am. Chem. Soc., 1982, 104, 2198).

An $R^3CO_2H$ group may also be prepared from oxidative cleavage of the corresponding diol, $CH(OH)CH_2OH$, using sodium periodate catalysed by ruthenium trichloride with an acetonitrile-carbontetrachloride-water solvent system (V. S. Martin et al, Tetrahedron Letters, 1988, 29(22), 2701).

$R^3$ groups containing a cyano or carboxy group may also be prepared by conversion of an alcohol to a suitable leaving group such as the corresponding tosylate by reaction with para-toluenesulphonyl chloride (M. R. Bell, J. Med. Chem., 1970, 13, 389), or the iodide using triphenylphosphine, iodine, and imidazole (G. Lange, Synth. Commun., 1990, 20, 1473). The second stage is the displacement of the leaving group with cyanide anion (L A. Paquette et al, J. Org. Chem., 1979, 44 (25), 4603; P. A. Grieco et al, J. Org. Chem., 1988, 53 (16), 3658). Finally acidic hydrolysis of the nitrile group gives the desired acids (H. Rosemeyer et al, Heterocycles, 1985, 23 (10), 2669). The hydrolysis may also be carried out with base e.g. potassium hydroxide (H. Rapoport, J. Org. Chem., 1958, 23, 248) or enzymatically (T. Beard et al, Tetrahedron Asymmetry, 1993, 4 (6), 1085).

Other functional groups in $R^3$ may be obtained by conventional conversions of carboxy or cyano groups.

Tetrazoles are conveniently prepared by reaction of sodium azide with the cyano group (e.g. F. Thomas et al, Bioorg. Med. Chem. Lett., 1996, 6 (6), 631; K. Kubo et al, J. Med. Chem., 1993, 36, 2182) or by reaction of azidotri-n-butyl stannane with the cyano group followed by acidic hydrolysis (P. L. Ornstein, J. Org. Chem., 1994, 59, 7682 and J. Med. Chem, 1996, 39 (11), 2219).

The 3-hydroxy-3-cyclobutene-1,2-dion-4-yl group (e.g. R. M. Soll, Bioorg. Med. Chem. Lett., 1993, 3 (4), 757 and W. A. Kinney, J. Med. Chem., 1992, 35 (25), 4720) can be prepared by the following sequence:—(1) a compound where $R^3$ is $(CH_2)_n$CHO (n=0, 1, 2) is treated with triethylamine, carbon tetrabromide/triphenylphosphine to give initially $(CH_2)_n$ CH=$CBr_2$; (2) dehydrobromination of this intermediate to give the corresponding bromoethyne derivative $(CH_2)_n$ C≡CBr (for this 2 stage sequence see D. Grandjean et al, Tetrahedron Letters, 1994, 35 (21), 3529); (3) palladium-catalysed coupling of the bromoethyne with 4-(1-methylethoxy)-3-(tri-n-butylstannyl)cyclobut-3-ene-1,2-dione (Liebeskind et al, J. Org. Chem., 1990, 55, 5359); (4) reduction of the ethyne moity to —CH2CH2— under standard conditions of hydrogen and palladium on charcoal catalysis (see Howard et al, Tetrahedron, 1980, 36, 171); and finally (4) acidic hydrolysis of the methylethoxyester to generate the corresponding 3-hydroxy-3-cyclobutene-1,2-dione group (R. M. Soll, Bioorg. Med. Chem. Lett., 1993, 3 (4), 757).

The tetrazol-5-ylaminocarbonyl group may be prepared from the corresponding carboxylic acid and 2-aminotetrazole by dehydration with standard peptide coupling agents such as 1,1'-carbonyldiimidazole (P. L. Ornstein et al, J. Med Chem, 1996, 39 (11), 2232).

The alkyl and alkenyl-sulphonylcarboxamides are similarly prepared from the corresponding carboxylic acid and the alkyl- or alkenyl-sulphonamide by dehydration with standard peptide coupling agents such as 1,1'-carbonyldiimidazole (P. L. Ornstein et al, J. Med. Chem., 1996, 39 (11), 2232).

The hydroxamic acid groups are prepared from the corresponding acids by standard amide coupling reactions eg N. R. Patel et al, Tetrahedron, 1987, 43 (22), 5375

2,4-thiazolidinedione groups may prepared from the aldehydes by condensation with 2,4-thiazolidinedione and subsequent removal of the olefinic double bond by hydrogenation.

The preparation of 5-oxo-1,2,4-oxadiazoles from nitrites is decribed by Y. Kohara et al, Bioorg. Med. Chem. Lett., 1995, 5(17), 1903.

1,2,4-triazol-5-yl groups may be prepared from the corresponding nitrile by reaction with an alcohol under acid conditions followed by reaction with hydrazine and then an $R^{10}$-substituted activated carboxylic acid (see J B Polya in 'Comprehensive Heterocyclic Chemistry' Edition 1 p762, Ed A R Katritzky and C W Rees, Pergamon Press, Oxford 1984 and J. J. Ares et al, J. Heterocyclic Chem., 1991, 28(5), 1197).

The cyclohexylamine or cyclohexenylamine $NH_2$ is converted to $NR^2R^4$ by conventional means such as amide or sulphonamide formation with an acyl derivative for compounds where U or $X^{1a}$ is CO or $SO_2$ or, where $R^4$ is —$H_2R^5$, or U or $X^{1a}$ is $CH_2$, by alkylation with an alkyl halide or other alkyl derivative $R^4$—W in the presence of base, acylation/reduction or reductive alkylation with an aldehyde.

Where one of $R^3$ and $R^6$, $R^7$, $R^8$ or $R^9$ contains a carboxy group and the other contains a hydroxy or amino group they may together form a cyclic ester or amide linkage. This linkage may form spontaneously during coupling of the compounds of formulae (IV) and (V) or in the presence of standard peptide coupling agents.

It will be appreciated that under certain circumstances interconvertions may interfere, for example, hydroxy groups in A or B and the cyclohexyl- or cyclohexenylamine will require protection e.g. as a carboxy- or silyl-ester group for hydroxy and as an acyl derivative for nitrogen, during conversion of $R^{1a'}$, $R^{1'}$, $R^{2'}$, $R^{3'}$ or $R^{4'}$, or during the coupling of the compounds of formulae (IV) and (V).

Compounds of formulae (IV) and (V) are known compounds, (see for example Smith et al, J. Amer. Chem. Soc., 1946, 68, 1301) or prepared analogously, see for example the references cited above.

Compounds of formula (IV) where X is $CR^6R^7SO_2W$ may be prepared by a route analogous to that of Ahmed El Hadri et al, J. Heterocyclic Chem., 1993, 30(3), 631. Thus compounds of formula (IV) where X is $CH_2SO_2OH$ may be prepared by reacting the corresponding 4-methyl compound with N-bromosuccinimide, followed by treatment with sodium sulfite. The leaving group W may be converted to another leaving group W, e.g. a halogen group, by conventional methods.

The isocyanate of formula (IV) may be prepared conventionally from a 4-amino derivative such as 4-amino-quinoline, and phosgene, or phosgene equivalent (eg triphosgene) or it may be prepared more conveniently from a 4-carboxylic acid by a "one-pot" Curtius Reaction with diphenyl phosphoryl azide (DPPA) [see T. Shiori et al. Chem. Pharm. Bull. 35, 2698-2704 (1987)].

The 4-amino derivatives are commercially available or may be prepared by conventional procedures from a corresponding 4-chloro derivative by treatment with ammonia (O. G. Backeberg et. al., J. Chem Soc., 381, 1942) or propylamine hydrochloride (R. Radinov et. al., Synthesis, 886, 1986).

4-Alkenyl compounds of formula (IV) may be prepared by conventional procedures from a corresponding 4-halogeno-derivative by e.g. a Heck synthesis as described in e.g. Organic Reactions, 1982, 27, 345.

4-Halogeno derivatives of compounds of formula (IV) are commercially available, or may be prepared by methods known to those skilled in the art. A 4-chloroquinoline is prepared from the corresponding quinolin-4-one by reaction with phosphorus oxychloride (POCl$_3$) or phosphorus pentachloride, PCl$_5$. A-4-bromo-substituent may be prepared from the quinolin- or naphthyridin-4-one by reaction with phosphorus tribromide (PBr3) in DMF. A 4-chloroquinazoline is prepared from the corresponding quinazolin-4-one by reaction with phosphorus oxychloride POCl$_3$) or phosphorus pentachloride, PCl$_5$. A quinazolinone and quinazolines may be prepared by standard routes as described by T. A. Williamson in *Heterocyclic Compounds*, 6, 324 (1957) Ed. R. C. Elderfield.

Activated carboxy derivatives X=A'COW of formula (IV) may be prepared from X=A'CO$_2$H derivatives in turn prepared from CO$_2$H derivatives by conventional methods such as homologation.

4-Carboxy derivatives of compounds of formula (IV) are commercially available or may be prepared by conventional procedures for preparation of carboxy heteroaromatics well known to those skilled in the art. For example, quinazolines may be prepared by standard routes as described by T. A. Williamson in *Heterocyclic Compounds*, 6, 324 (1957) Ed. R. C. Elderfield. These 4-carboxy derivatives may be activated by conventional means, e.g. by conversion to an acyl halide or anhydride.

4-Carboxy derivatives such as esters may be reduced to hydroxymethyl derivatives with for example lithium aluminium hydride. Reaction with mesyl chloride and triethylamine would give the mesylate derivative. A diazo compound (X is —CH═N$_2$) may be prepared from the 4-carboxaldehyde via the tosyl hydrazone. The 4-carboxaldehyde may be obtained from from the acid by standard procedures well known to those skilled in the art.

A 4-oxirane derivative of compounds of formula (IV) is conveniently prepared from the 4-carboxylic acid by first conversion to the acid chloride with oxalyl chloride and then reaction with trimethylsilyldiazomethane to give the diazoketone derivative. Subsequent reaction with 5M hydrochloric acid gives the chloromethylketone. Reduction with sodium borohydride in aqueous methanol gives the chlorohydrin which undergoes ring closure to afford the epoxide on treatment with base, e.g. potassium hydroxide in ethanol-tetrahydrofuran.

Alternatively and preferably, 4-oxirane derivatives can be prepared from bromomethyl ketones which can be obtained from 4-hydroxy compounds by other routes well known to those skilled in the art. For example, hydroxy compounds can be converted to the corresponding 4-trifluoromethanesulphonates by reaction with trifluoromethanesulphonic anhydride under standard conditions (see K. Ritter, Synthesis, 1993, 735). Conversion into the corresponding butyloxyvinyl ethers can be achieved by a Heck reaction with butyl vinyl ether under palladium catalysis according to the procedure of W. Cabri et al, J. Org. Chem, 1992, 57 (5), 1481. (Alternatively, the equivalent intermediates can be attained by Stille coupling of the trifluoromethanesulphonates or the analaogous chloro derivatives with (1-ethoxyvinyl)tributyl tin, (T. R. Kelly, J. Org. Chem., 1996, 61, 4623).) The alkyloxyvinyl ethers are then converted into the corresponding bromomethylketones by treatment with N-bromosuccinimide in aqueous tetrahydrofuran in a similar manner to the procedures of J. F. W. Keana, J. Org. Chem., 1983, 48, 3621 and T. R. Kelly, J. Org. Chem., 1996, 61, 4623.

The 4-hydroxyderivatives can be prepared from an aminoaromatic by reaction with methylpropiolate and subsequent cyclisation, analogous to the method described in N. E. Heindel et al, J. Het. Chem., 1969, 6, 77. For example, 5-amino-2-methoxy pyridine can be converted to 4-hydroxy-6-methoxy-[1,5]naphthyridine using this method.

If a chiral reducing agent such as (+) or (−)-B-chlorodiisopinocamphenylborane ['DIP-chloride'] is substituted for sodium borohydride, the prochiral chloromethylketone is converted into the chiral chlorohydrin with ee values generally 85-95% [see C. Bolm et al, *Chem. Ber.* 125, 1169-1190, (1992)]. Recrystallisation of the chiral epoxide gives material in the mother liquor with enhanced optical purity (typically ee 95%).

The (R)-epoxide, when reacted with an amine derivative gives ethanolamine compounds as single diastereomers with (R)-stereochemistry at the benzylic position.

Alternatively, the epoxide may be prepared from the 4-carboxaldehyde by a Wittig approach using trimethylsulfonium iodide [see G. A. Epling and K-Y Lin, *J. Het. Chem.*, 1987, 24, 853-857], or by epoxidation of a 4-vinyl derivative.

Pyridazines may be prepared by routes analogous to those described in Comprehensive Heterocyclic Chemistry, Volume 3, Ed A. J. Boulton and A. McKillop and napthyridines may be prepared by routes analogous to those described in Comprehensive Heterocyclic Chemistry, Volume 2, Ed A. J. Boulton and A. McKillop.

4-Hydroxy-1,5-naphthyridines can be prepared from 3-aminopyridine derivatives by reaction with diethyl ethoxymethylene malonate to produce the 4-hydroxy-3-carboxylic acid ester derivative with subsequent hydrolysis to the acid, followed by thermal decarboxylation in quinoline (as for example described for 4-Hydroxy-[1,5]naphthyridine-3-carboxylic acid, J. T. Adams et al., *J. Amer. Chem. Soc.*, 1946, 68, 1317). A 4-hydroxy-[1,5]naphthyridine can be converted to the 4-chloro derivative by heating in phosphorus oxychloride, or to the 4-methanesulphonyloxy or 4-trifluoromethanesulphonyloxy derivative by reaction with methanesulphonyl chloride or trifluoromethanesulphonic anhydride, respectively, in the presence of an organic base. A 4-amino 1,5-naphthyridine can be obtained from the 4-chloro, 4-methanesulphonyloxy or 4-trifluoromethanesulphonyloxy derivative by reaction with n-propylamine in pyridine.

Similarly, 6-methoxy-1,5-naphthyridine derivatives can be prepared from 3-amino-6-methoxypyridine.

1,5-Naphthyridines may be prepared by other methods well known to those skilled in the art (for examples see P. A. Lowe in "Comprehensive Heterocyclic Chemistry" Volume 2, p 581-6$^2$7, Ed A. R. Katritzky and C. W. Rees, Pergamon Press, Oxford, 1984).

The 4-hydroxy and 4-amino-cinnolines may be prepared following methods well known to those skilled in the art [see A. R. Osborn and K. Schofield, *J. Chem. Soc.* 2100 (1955)]. For example, a 2-aminoacetophenone is diazotised with sodium nitrite and acid to produce the 4-hydroxycinnoline with conversion to chloro and amino derivatives as described for 1,5-naphthyridines.

R$^A$ groups where the ring (y) is 4-pyridyl are available by the sequence described below, starting from an aromatic or heterocyclic amine (1), with at least one free CH position adjacent to the amine. Reaction with Meldrum's acid and trimethyl orthoformate in ethanol at reflux affords the corresponding 2,2-dimethyl-5-phenylaminomethylene-[1,3]dioxane-4,6-dione derivatives (2). These can be cyclised at elevated temperatures (180-220° C.) in inert solvents such as Dowtherm to give the corresponding 1H-quinolin-4-one (3) or heterocyclic analogues eg 1H-[1,6]naphthyridin-4-one. These processes are well-established and are described by Walz and Sundberg (J. Org. Chem., 2000, 65 (23), 8001) and by Todter and Lackner (Synthesis, 1997 (5) 576).

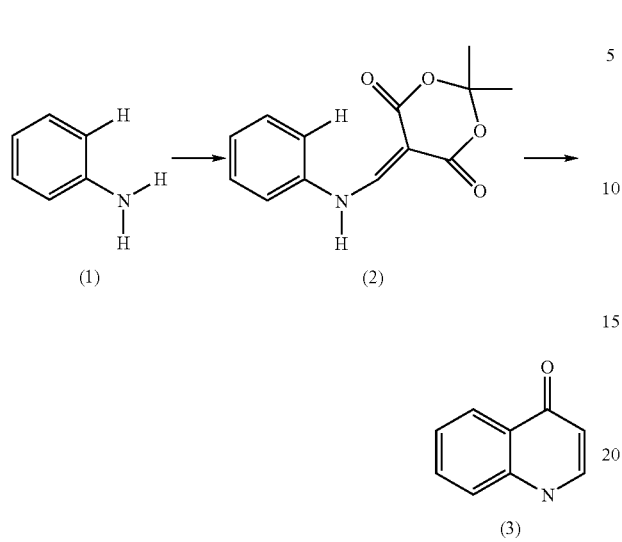

Activation of the quinolone species related to (3) into the corresponding 4-quinolyl bromides (4) can be accomplished with phosphorous oxybromide or more preferably phosphorous tribromide in N,N-dimethylformamide (see M. Schmittel et at, Synlett, 1997, (9), 1096 and K. Gould et al, J. Med., Chem., 1988, 31 (7), 1445). The corresponding chlorides (5) are available by using phosphoryl oxychloride (for instance C. W. Wright et al, J. Med., Chem., 2001, 44 (19), 3187).

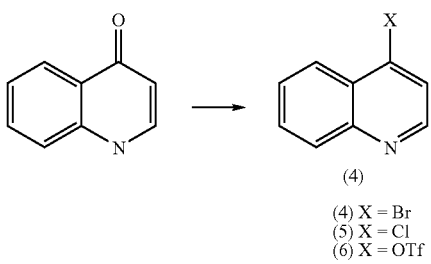

(4) X = Br
(5) X = Cl
(6) X = OTf

Alternatively, the quinolone species may be activated to the corresponding 1,1,1-trifluoro-methanesulfonic acid quinolin-4-yl esters (6) by the action of agents such as triflic anhydride or more preferably N-trifluoromethanesulphonimide (see for example M. Alvarez et al, Tet 2000, 56 (23) 3703; M. Alvarez et al, Eur. I. Org., Chem., 2000, (5), 849; J. Joule et al, Tet, 1998, 54 (17), 4405; J. K. Stille et al, J.A.C.S., 1988, 110 (12), 4051).

Activated species such as (4), (5), and (6) can then be subjected to a variety of metal-catalysed coupling reactions, such as amidation with primary carboxamides to give compounds such as (7) following the procedures of S. L. Buchwald et al (J.A.C.S., 2001, 123, 4051 and 7727; Org. Lett., 1999, 1, 35) or Sonogashira coupling with acetylenes to give compounds such as (8) (see A. Droz et al, Helv. Chim. Acta., 2001, 84 (8), 2243; M. Belly et al, Synlett, 2001 (2), 222; M. Pirrung et al, J.A.C.S., 2001, 123 (16), 3638).

$R^A$ thieno[3,2-b]pyridin-7-yl, 2,3-dihydro-[1,4]dioxino[2,3-b]pyridin-8-yl, quinolin-8-yl and isoquinolin-5-yl derivatives are commercially available or prepared by conventional methods from commercially available or literature derivatives, for example 4H-thieno[3,2-b]pyridin-4-one, 2,3-dihydro-[1,4]dioxino[2,3-b]pyridine (prepared by the method of H. Neunhoffer et al, Chem., Ber., 1990, 123), 2-methoxy-quinolin-8-ylamine (prepared by the method of K. Mislow et al J.A.C.S. 68, 1353 (1946)), 2,8-quinolinediol or trifluoromethane sulphonic acid-isoquinolin-5-yl ester (prepared as in D. Ortwine et al, J. Med. Chem., 1992, 35 (8), 1345).

$R^A$ quinoxalin-5-yl derivatives may be obtained from 2- or 3-methylquinoxalin-5-ol prepared as described by Y. Abe et al, J. Med. Chem., 1998, 41 (21), 4062 or from suitable substituted derivatives prepared by analogous methods. $R^A$ 3-methoxyquinoxaline-5-yl derivatives may be obtained from 3-oxoquinoxalin-5-yl prepared by the general methods of F. J. Wolf et al., J.A.C.S. 1949, 71, 6, using a suitable methylating agent such as trimethylsilyl(diazomethane). The corresponding 1,2,3,4-tetrahydro-quinoxalin-5-yl may be prepared by reduction with a suitable reducing agent such as sodium cyanoborohydride in the presence of an acid such as acetic acid.

The isoquinolin-8-yl system can be prepared from the appropriately substituted benzylamine by cyclocondensation with diethoxy-acetaldehyde (see, for example, K. Kido and Y. Watanabe, Chemical & Pharmaceutical Bulletin, 35(12), 4964-6; 1987). Alternatively 8-bromo-isoquinoline (prepared by the method of F. T. Tyson, J.A.C.S., 1939, 61, N. Briet et al., Tetrahedron (2002), 58(29), 5761-5766 or W. D. Brown, et al., Synthesis (2002), (1), 83-86. 183 can be subjected to N-oxidation and rearrangement to give 8-bromo-2H-isoquinolin-1-one. This can be N-methylated to give 8-bromo-2-methyl-2H-isoquinolin-1-one, an appropriate intermediate for the 2-methyl-1-oxo-1,2-dihydroisoquinolin-8-yl system.

The 1-methoxy-isoquinolin-8-yl system can also be obtained from the 8-bromoisoquinoline-N-oxide above by rearrangement with methyl chloroformate to give 8-bromo-1-methoxy-isoquinoline, an appropriate intermediate for the 1-methoxy-isoquinolin-8-yl system The compounds of formula (V) are either commercially available or may be prepared by conventional methods.

For compounds of formula (V), where Y is $NHR^{11'}$ suitable amines may be prepared from the corresponding 4-substituted cyclohexyl- or cyclohexenyl acid or alcohol. In a first instance, an N-protected cyclohexyl- or cyclohexenyl amine containing an acid bearing substituent, can undergo a Curtius rearrangement and the intermediate isocyanate can be converted to a carbamate by reaction with an alcohol. Conversion to the amine may be achieved by standard methods well known to those skilled in the art used for amine protecting group removal. For example, an acid substituted N-protected cyclohexyl- or cyclohexenyl amine can undergo a Curtius rearrangement e.g. on treatment with diphenylphosphoryl azide and heating, and the intermediate isocyanate reacts in the presence of 2-trimethylsilylethanol to give the trimethylsilylethylcarbamate (T. L. Capson & C. D. Poulter, *Tetrahedron Lett.*, 1984, 25, 3515). This undergoes cleavage on treatment with tetrabutylammonium fluoride to give the 4-amine substituted N-protected compound of formula (V). Alternatively, an acid group $(CH_2)_{n-1}CO_2H$ may be converted to $(CH_2)_n NHR^{11}$ by reaction with an activating agent such as isobutyl chloroformate followed by an amine $R^{11'}NH_2$ and the resulting amide reduced with a reducing agent such as $LiAlH_4$.

In a second instance, an N-protected cyclohexyl- or cyclohexenyl amine containing an alcohol bearing substituent undergoes a Mitsunobu reaction (for example as reviewed in Mitsunobu, *Synthesis*, (1981), 1), for example with succinimide in the presence of diethyl azodicarboxylate and triphenylphosphine to give the phthalimidoethylcyclohexyl- or cyclohexenyl amine. Removal of the phthaloyl group, for example by treatment with methylhydrazine, gives the amine of formula (V).

Compounds of formula (V) where n=1 may be prepared from the compound where n=0 by homologation eg starting from a compound of formula (V) where $Y=CO_2H$.

Compounds of formula (V) with a —C≡CH group may be prepared from the ketone treated with trimethylsilylacetylene and n-butyl lithium in dimethylformamide at low temperature followed by removal of the trimethylsilyl group with potassium carbonate in methanol or a fluoride source such as KF or tetrabutylammonium fluoride.

Compounds of formula (V) with a —CONHR$^{11}$ group may be prepared from the corresponding nitrile by partial hydrolysis with with concentrated mineral acid at ambient temperature, such as concentrated hydrochloric acid (M. Brown et al, J. Med. Chem., 1999, 42, (9), 1537) or with concentrated sulphuric acid (F. Macias et al Tetrahedron, 2000, 56, (21), 3409).

Compounds of formula (V) with a —OCONH$_2$ group may be prepared from the corresponding alcohol by reaction with phosgene followed by ammonia.

Compounds of formula (V) substituted by $R^3$ at the 1- or 4-position may be prepared from a 1-keto derivative via a cyanohydrin reaction with sodium cyanide/hydrochloric acid in an ether/water two phase system (J. Marco et al Tetrahedron, 1999, 55, (24), 7625), or using trimethylsilylcyanide and zinc iodide catalysis in dichloromethane (A. Abad et al, J. Chem. Soc., Perkin 1, 1996, 17, 2193), followed by hydrolysis by heating in concentrated hydrochloric acid to give the α-hydroxy acid (Compound (V), $Y=CO_2H$, n=0, $R^{3'}=OH$ and $Q^1$ is $NR^2R^{4'}$) or partial hydrolysis to the carboxamide —CONH$_2$ as described above. In examples where there is trimethylsilyl protection of the alcohol, this is removed under the acidic conditions of cyanide hydrolysis. It will be appreciated that the amine protecting group eg N-carboxylic acid tert-butyl ester is concomitantly removed during the acid hydrolysis step, necessitating a standard reprotection with di-tert-butyl dicarbonate, giving key intermediates (V) such as (4-carbamoyl-4-hydroxy-cyclohexyl)-carbamic acid tert-butyl ester. It is noteworthy that during the cyanohydrin formation there is little or no stereoselectivity with regard to relative stereochemistry, and the (4-carbamoyl-4-hydroxy-cyclohexyl)-carbamic acid tert-butyl ester produced in this process is a mixture of cis and trans stereoisomers. These isomers can be separated by careful chromatography.

The same 1-keto-derivative could undergo a Wittig reaction with $Ph_3PCH=CO_2Me$ to give the α,β-unsaturated carboxylic ester $MeO_2C—CH=C<Ring$, which could be epoxidised (eg meta-chloroperbenzoic acid) to give the α,β-epoxyester. Alternatively this could be formed directly from the keto-derivative via a glycidic ester condensation with an α-halogeno-ester. Base hydrolysis would afford the α,β-epoxy-carboxylic acid, which on reduction (eg lithium triethylborohydride—see J. Miklefield et al J. Amer. Chem. Soc. 117, 1153-1154 (1995) or hydrogenation over platinum oxide (see Artamonow Zh. Obshch. Khim. 28 1355-1359 (1958)) would afford the β-hydroxy acid (Compound (V) $Y=CO_2H$, n=1, $R^3=OH$). Alternatively a Reformatsky reaction with the keto-derivative and an α-bromocarboxylic acid ester and zinc, followed by acid hydrolysis would afford the β-hydroxycarboxylic acid directly. The 1-keto-derivative could also undergo a Strecker type synthesis via a Bucherer-Bergs procedure (potassium cyanide/ammonium carbonate) [see T. Scott Yokum et al. Tetrahedron Letters, 38, 4013-4016 (1997)] to give the α-amino-carboxylic acid (Compound (V) $Y=CO_2H$, n=0, $R^{3'}=NH_2$).

An alternative route to 1-substituted compounds (V) involves a Diels Alder reaction between butyl acrylate and acetoxy butadiene to give (1). Elimination of acetic acid and hetero Diels Alder reaction with an in-situ generated acyl nitroso compound gives the bicyclic hydroxylamine product (3). The ester is transformed to an amide in two steps, and catalytic hydrogenation is used to reduce the double bond, remove the nitrogen protection and cleave the NO bond. After reprotection of the amino group, the cyclohexane amide with the required stereochemistry is obtained.

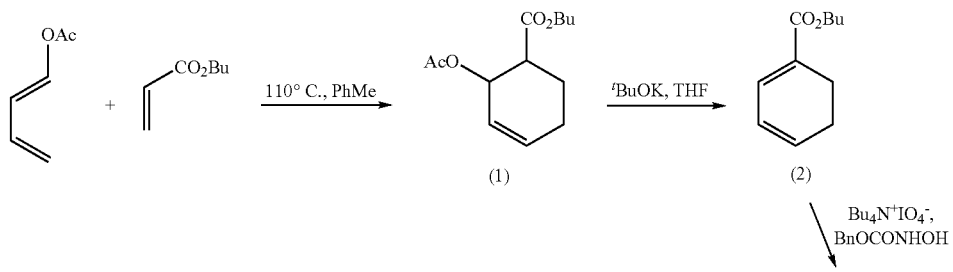

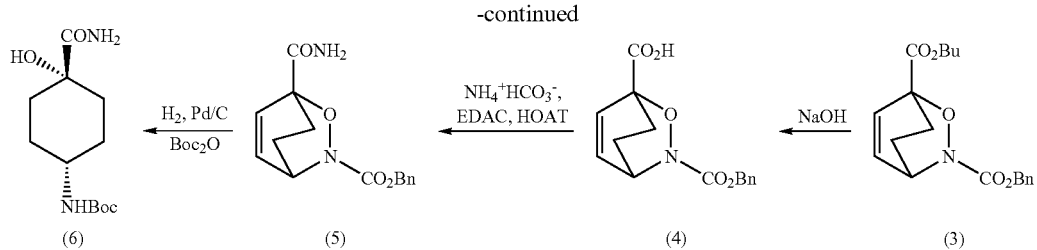

Two steps can be avoided by starting with acrylamide:

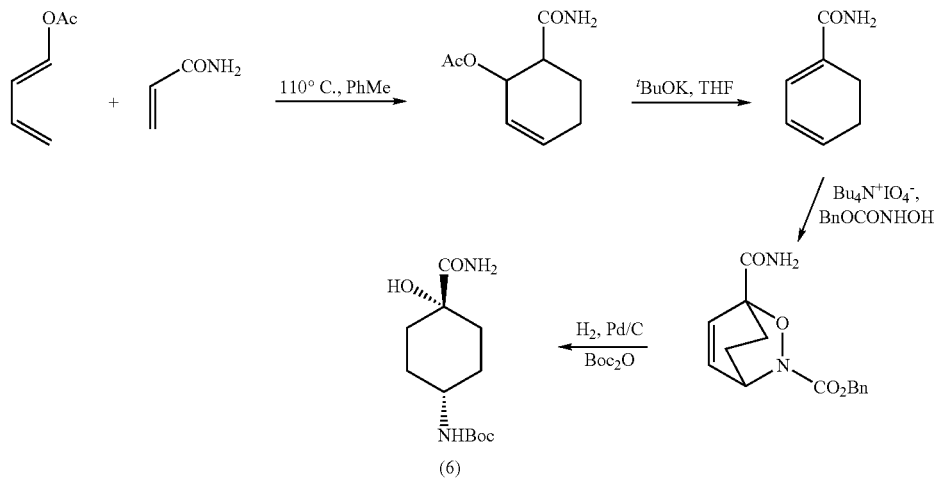

Compounds of formula (V) substituted by $R^3$ at the 2- or 3-position may be prepared from the corresponding substituted phenyl derivative $1\text{-}Y(CH_2)_nPh(\text{---}R3)\text{-}4\text{-}NR^2$ (eg where Y=carboxylic acid) by hydrogenation at elevated temperature and pressure using a Pt or $R^u$ catalyst.

Compounds of formula (V) with a 3-hydroxyl group may be prepared from a 3,4 oxirane-cyclohexane carboxylic acid by reaction with an amine $NHR^2R^4$ or azide (followed by conversion of the azide to amino). [See for example K. Krajewski et al. Tetrahedron Asymmetry 10, 4591-4598 (1999)].

The ester group may be epimerised by heating in strong base, hydrolysed to the carboxylic acid and cyclised to the lactone using a conventional coupling reagent (EDC). Other conventional reagents eg DCC, $Im_2CO$, HATU etc. may also be used. The lactone is readily purified by chromatography. The lactone is readily opened with aqueous ammonia in tetrahydrofuran to give the required (racemic)amide.

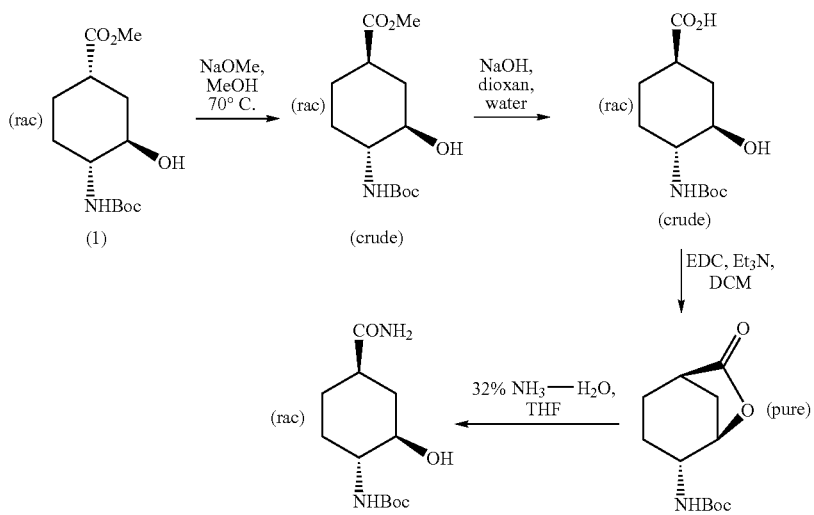

An improved procedure starting from 3-cyclohexene carboxylic acid may be used to prepare single enantiomers. 3-Cyclohexene carboxylic acid (2) is resolved via α-Me benzylamine salt (Schwartz et al, J. Am. Chem. Soc., 100, 5199, (1978)). A higher yield of lactone (3) can be achieved using a larger excess of reagents. Lactone opening with ammonia gives (4), which is treated with azide to give (5) which has the required trans relative stereochemistry between the amide and N-substituent. Finally, azide reduction and Boc protection gives (1) a compound of formula (V).

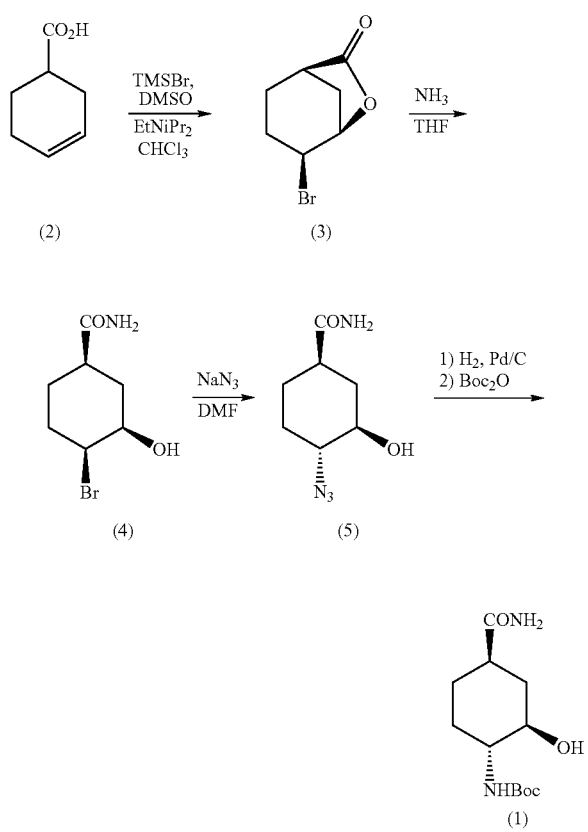

R³ halogen can be introduced onto a cyclohexane ring via treatment of a silyl enol ether with an electrophilic halogenating, such as a fluorinating, agent. For example, ethyl-4-oxo cyclohexanecarboxylate is converted to its TMS enol ether (S-W Lin, Bioorg. Med. Chem. Lett, 10; 11; 1297-1298, 2000). This conversion may be carried out using an optically active base to give enantiomerically enriched material [K W Henderson et al, JCS Chem Comm, 479-480, (2000); N S Simplins et al, Tet. Lett, 30, 51, 7241-7244, (1989); K Koga et al, J. Am. Chem. Soc., 108, 543-545, (1986); P Knochel, Ang. Chem. Int. Ed., 37, (21), 3014-3016 (1998); V K Aggarwal, J. Chem. Soc. Perkin Trans. 1, 2883 (1999)]. Treatment with an electrophilic fluorinating agent, for example Selectfluor, yields the chiral α-fluoroketones which may be separated by silica gel chromatography. Reductive amination with an amine, for example benzylamine or a chiral benzylamine for example α-methyl benzylamine using sodium cyanoborohydride or sodium triacetoxyborohydride yields the amino ester with predominantly the cis relationship between the amino and fluoro substituents. This may be converted to the amino amide. Diastereoisomers may be separated by an appropriate combination of silica gel chromatography, HPLC and crystallisation of the free base or a suitable salt.

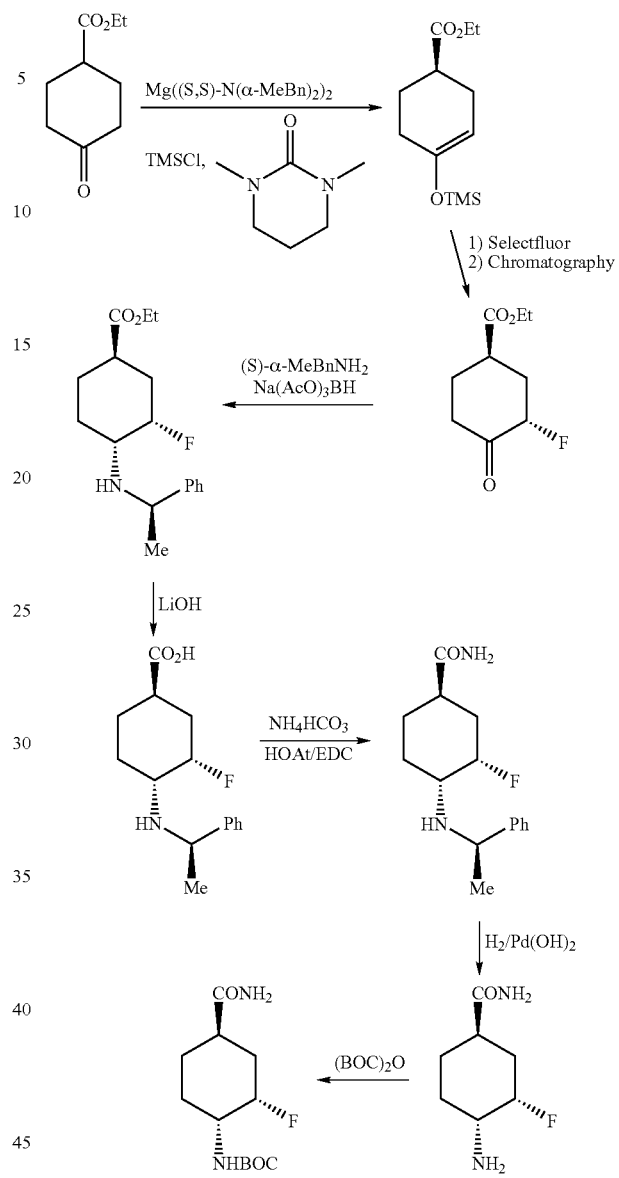

Selectfluor™: 1-chloromethyl-4-fluoro-1,4-diazoniabicyclo[2.2.2]octane bis(tetrafluoroborate α-MeBnNH₂: α-methylbenzylamine (BOC)₂O: di-tert-butyldicarbonate BOC: tert-butyloxycarbonyl HOAt: 1-hydroxy-7-azabenzotriazole EDC: 1-ethyl-3-(3-dimethylaminopropyl)carbodiimide hydrochloride.

R⁴-halides and R⁴—W derivatives, acyl derivatives or aldehydes are commercially available or are prepared conventionally. The aldehydes may be prepared by partial reduction of the corresponding ester with lithium aluminium hydride or di-isobutylaluminium hydride or more preferably by reduction to the alcohol, with lithium aluminium hydride or sodium borohydride (see *Reductions by the Alumino- and Borohydrides in Organic Synthesis,* 2nd ed., Wiley, N.Y., 1997; *JOC*, 3197, 1984; *Org. Synth. Coll.*, 102, 1990; 136, 1998; *JOC*, 4260, 1990; *TL*, 995, 1988; *JOC*, 1721, 1999; *Liebigs Ann./Recl.*, 2385, 1997; *JOC*, 5486, 1987), followed by oxidation to the aldehyde with manganese (II) dioxide, or by a 'Swern' procedure (oxalyl chloride/DMSO), or by using potassium dichromate (PDC). The aldehydes may also be prepared from carboxylic acids in two stages by conversion to a mixed anhydride for example by reaction with isobutyl chloroformate followed by reduction with sodium borohydride (R. J. Alabaster et al., Synthesis, 598, 1989) to give the hydroxymethyl substituted heteroaromatic or aromatic and then oxidation with a standard oxidising agent such as pyridinium dichromate or manganese (II) dioxide. Acyl derivatives may be prepared by activation of the corresponding ester. $R^4$-halides such as bromides may be prepared from the alcohol $R^4OH$ by reaction with phosphorus tribromide in dichloromethane/triethylamine. Where $X^{2a}$ is CO and $X^{3a}$ is $NR^{13a}$ the $R^4$-halide may be prepared by coupling an $X^{4a}$—$NH_2$ amine and bromoacetyl bromide. $R^4$—W derivatives such as methanesulphonyl derivatives may be prepared from the alcohol $R^4OH$ by reaction with methane sulphonyl chloride. The leaving group W may be converted to another leaving group W, e.g. a halogen group, by conventional methods. Alternatively the aldehyde $R^5_2CHO$ and sulphonic acid derivative $R^5_2SO_2W$ may be generated by treatment of the $R^5_2H$ heterocycle with suitable reagents. For example benzoxazinones, or more preferably their N-methylated derivatives can be formylated with hexamine in either trifluoroacetic acid or methanesulfonic acid, in a modified Duff procedure [O. I. Petrov et al. *Collect. Czech. Chem. Commun.* 62, 494-497 (1997)]. 4-Methyl-4H-benzo[1,4]oxazin-3-one may also be formylated using dichloromethyl methyl ether and aluminium chloride giving exclusively the 6-formyl derivative.

Reaction of a $R^5_2H$ heterocycle with chlorosulphonic acid gives the sulphonic acid derivative (by methods analogous to Techer et. al., C. R. Hebd. *Seances Acad. Sci. Ser. C;* 270, 1601, 1970).

The aldehyde $R^5_2CHO$ may be generated by conversion of an $R^5_2$ halogen or $R^5_2$trifluoromethane sulphonyloxy derivative into an olefin with subsequent oxidative cleavage by standard methods. For example, reaction of a bromo derivative under palladium catalysis with trans-2-phenylboronic acid under palladium catalysis affords a styrene derivative which upon ozonolysis affords the required $R^5_2CHO$ (Stephenson, G. R., Adv. Asymmetric Synth. (1996), 275-298. Publisher: Chapman & Hall, London).

Where $R^5_2$ is an optionally substituted benzoimidazol-2-yl group, the compound of formula (V) where $R^4$ is $R^4$ may be obtained by converting a $R^{4'}$ cyanomethyl group with partial hydrolysis to give the 2-ethoxycarbonimidoylethyl group which can then be condensed with an appropriately substituted 1,2-diaminobenzene to give the required benzoimidazol-2-yl group.

$R^5_2H$ heterocycles are commercially available or may be prepared by conventional methods. For example where a benzoxazinone is required, a nitrophenol may be alkylated with for example ethyl bromoacetate and the resulting nitro ester reduced with Fe in acetic acid (alternatively Zn/AcOH/HCl or $H_2$/Pd/C or $H_2$/Raney Ni). The resulting amine may undergo spontaneous cyclisation to the required benzoxazinone, or cyclisation may be induced by heating in acetic acid. Alternatively a nitrophenol may be reduced to the aminophenol, which is reacted with chloroacetyl chloride [method of X. Huang and C. Chan, *Synthesis* 851 (1994)] or ethyl bromoacetate in DMSO [method of Z. Moussavi et al. *Eur. J. Med. Chim. Ther.* 24, 55-60 (1989)]. The same general routes can be applied to prepare benzothiazinones [See for example F. Eiden and F. Meinel, Arch. Pharm. 312, 302-312 (1979), H. Fenner and R Grauert *Liebigs. Ann. Chem.* 193-313 (1978)]]. A variety of routes are available to prepare aza analogues of benzothiazinones via the key corresponding aldehydes. For instance, 2-oxo-2,3-dihydro-1H-pyrido[3,4-b][1,4]thiazine-7-carbaldehyde may be accessed from 5-fluoro-2-picoline (E. J. Blanz, F. A. French, J. R. DoAmaral and D. A. French, J. Med. Chem. 1970, 13, 1124-1130) by constructing the thiazinone ring onto the pyridyl ring then functionalising the methyl substituent. The dioxin analogue of this aza substitution patern, 2,3-dihydro-[1,4]dioxino[2,3-c]pyridine-7-carbaldehyde is accessible from Kojic acid by aminolysis from pyrone to pyridone then annelating the dioxin ring. Other aza substitution patterns with pyridothiazin-3-one, pyridooxazin-3-one, and pyridodioxin ring systems are also accessible. Ortho-aminothiophenols may be conveniently prepared and reacted as their zinc complexes [see for example V. Taneja et al *Chem. Ind.* 187 (1984)]. Benzoxazolones may be prepared from the corresponding aminophenol by reaction with carbonyl diimidazole, phosgene or triphosgene. Reaction of benzoxazolones with diphosporus pentasulfide affords the corresponding 2-thione. Thiazines and oxazines can be prepared by reduction of the corresponding thiazinone or oxazinone with a reducing agent such as lithium aluminium hydride.

The amines $R^2R^{4'}NH$ are available commercially or prepared conventionally. For example amines may be prepared from a bromo derivative by reaction with sodium azide in dimethylformamide (DMF), followed by hydrogenation of the azidomethyl derivative over palladium-carbon. An alternative method is to use potassium phthalimide/DMF to give the phthalimidomethyl derivative, followed by reaction with hydrazine in DCM to liberate the primary amine.

Amines where $X^{2a}$ is CO and $X^{3a}$ is $NR^{13a}$ may be prepared by reacting an N-protected glycine derivative $HO_2C$—$X^{1a}$—$NH_2$ with $X^{4a}$—$NH_2$ by conventional coupling using eg EDC.

Conversions of $R^{1a'}$, $R^{1'}$, $R^{2'}$, $R^{3'}$ and $R^{4'}$ may be carried out on the intermediates of formulae (IV) and (V) prior to their reaction to produce compounds of formula (I) in the same way as described above for conversions after their reaction.

The pharmaceutical compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable salt or in vivo hydrolysable ester thereof is administered in the above-mentioned dosage range.

The compound of formula (I) may be the sole therapeutic agent in the compositions of the invention or a combination with other antibiotics or with a β-lactamase inhibitor may be employed.

Compounds of formula (I) are active against a wide range of organisms including both Gram-negative and Gram-positive organisms.

The following examples illustrate the preparation of certain compounds of formula (I) and the activity of certain compounds of formula (I) against various bacterial organisms.

EXAMPLES

Example 1

1-Hydroxy-t-4-[(3-oxo-3,4-dihydro-2H-pyrido[3,2-b][1,4]thiazin-6-ylmethyl)-amino]-r-cyclohexanecarboxylic acid thieno[3,2-b]pyridin-7-ylamide dihydrochloride (cis-1-hydroxy-4-{[(3-oxo-3,4-dihydro-2H-pyrido[3.2-b][1,4]thiazin-6-yl)methyl[amino}-N-thieno[3,2-b]pyridin-7-ylcyclohexanecarboxamide hydrochloride)

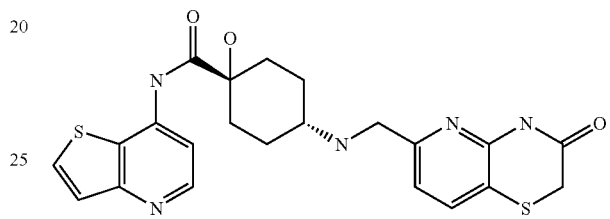

(a) 2-Acetoxycyclohex-3-enecarboxylic acid butyl ester

1-Acetoxy-1,3-butadiene (30.1 g, 0.268 mol) was dissolved in toluene (20 ml). To this was added butyl acrylate (37.9 ml, 0.265 mol) and hydroquinone (0.14 g). The colourless solution was heated at 120° C. for 26 hours under argon. More 1-acetoxy-1,3-butadiene (10.6 g, 0.095 mol) in toluene (2 ml) was then added, and heating continued for a further 68 hours. The solution was cooled then evaporated in vacuo to give a viscous yellow oil (69 g), which was used without further purification.

δH (CDCl$_3$) 0.91-0.95 (3H, m), 1.3-2.2 (11H, m), 2.6-2.72 (1H, m), 4.01-4.16 (2H, m), and 5.48-6.07 (3H, m).

(b) Cyclohexa-1,3-dienecarboxylic acid butyl ester

Crude butyl ester (a) (55.25 g, max 0.207 mol) was dissolved in dry tetrahydrofuran (320 ml) and cooled in an ice/salt bath. To this was added slowly, over 1 hour, potassium t-butoxide in tetrahydrofuran (1 M, 220 ml, 0.22 mol). After 0.5 hour water and petroleum ether were added and the mixture filtered quickly through kieselguhr. The phases were separated and the aqueous extracted with more petroleum ether (×2). The combined organic extracts were washed with brine, dried and evaporated to give a mobile orange oil (31.85 g, 86%), which was used immediately without further purification.

δH (CDCl$_3$) 0.93-0.99 (3H, m), 1.3-1.7 (4H, m), 2.2-2.5 (4H, m), 4.1-4.2 (2H, m), 6.0-6.2 (2H, m), and 6.95-7.02 (1H, m).

(c) 2-Oxa-3-aza-bicyclo[2.2.2]oct-5-ene-1,3-dicarboxylic acid 3-benzyl ester 1-butyl ester Crude butyl ester (b) (31.84 g, max 0.176 mol) was dissolved in dichloromethane (300 ml). To this was added N-hydroxy carbamic acid benzyl ester (30.9 g, 0.185 mol). This solution was cooled in an ice/salt bath then a solution of tetrabutylammonium periodate (80.1 g, 0.185 mol) in dichloromethane (100 ml) was added dropwise over 1 hour. After stirring for a further 1 hour, with cooling, the mixture was reduced to a small volume in vacuo then stirred vigorously while adding diethyl ether (1 liter). The mixture was filtered washing well with diethyl ether. The filtrate was then washed with aqueous sodium bisulphite (×2), and brine, dried and evaporated to give a brown oil. This residue was purified by chromatography on silica gel, eluting with 25-28% diethyl ether in petroleum ether, to give a viscous pale orange oil (42.41 g, 69%) (contaminated with a little benzyl alcohol).

δH (CDCl$_3$) 0.94 (3H, t), 1.35-1.75 (6H, m), 2.15-2.4 (2H, m), 4.2-4.35 (2H, m), 4.84-4.89 (1H, m), 5.12-5.20 (2H, m), 6.59-6.71 (2H, m), and 7.28-7.39 (5H, m).

(d) 2-Oxa-3-aza-bicyclo[2.2.2]oct-5-ene-1,3-dicarboxylic acid 3-benzyl ester

To a solution of di-ester (c) (42.13 g, 0.122 mol) in 1,4-dioxane (250 ml) was added aqueous sodium hydroxide solution (0.5 M, 250 ml, 0.125 mol). The mixture was stirred for 1 hour then washed with diethyl ether (×3). The aqueous phase was adjusted to pH2 with 5 M hydrochloric acid, and extracted with ethyl acetate (×3). The combined organic extracts were washed with brine, dried and evaporated to give a cream solid (29.53 g, 84%).

δH (CDCl$_3$/CD$_3$OD) 1.53-1.79 (2H, m), 2.13-2.39 (2H, m), 4.82-4.89 (1H, m), 5.11-5.23 (2H, m), 6.57-6.69 (2H, m), and 7.3-7.4 (5H, m).

(e) 1-Carbamoyl-2-oxa-3-aza-bicyclo[2.2.2]oct-5-ene-3-carboxylic acid benzyl ester The benzyl ester (d) (12.0 g, 41.5 mmol) and 1-hydroxy-7-azabenzotriazole (6.26 g, 46 mmol) were dissolved in DMF (100 ml) then l-ethyl-3-(3-dimethylaminopropyl)carbodiimide hydrochloride (8.79 g, 46 mmol) added. After stirring for 5 minutes ammonium hydrogen carbonate (8.22 g, 104 mmol) was added. Four further small portions of ammonium hydrogen carbonate were added over the next 7 hours. The mixture was then stirred overnight, diluted with water and extracted with ethyl acetate (×4). The combined organic extracts were washed with 5% aqueous citric acid then brine, dried and evaporated to give an off-white solid (9.9 g, 83%).

MS (+ve ion electrospray) m/e 289 (MH+).

(f) (4-Carbamoyl-r-4-hydroxy-c-cyclohexyl)-carbamic acid tert butyl ester

The benzyl ester (e) (9.75 g, 33.8 mmol) was dissolved in 1,4-dioxane (150 ml) and water (60 ml) and hydrogenated over 10% palladium on carbon (50% aqueous paste, 3.3 g) at 40° C. and 55 psi for 68 hours. More catalyst (2 g) was added after 4 hours. The mixture was then filtered through kieselguhr, washing well with 1,4-dioxane and water. To this solution was added 2 N sodium hydroxide (25 ml, 50 mmol) followed by a solution of di-tert-butyl dicarbonate (11.12 g, 51 mmol) in 1,4-dioxane (10 ml). The reaction mixture was stirred for 5 hours then reduced in volume in vacuo, before extracting with ethyl acetate (×5). The combined organic extracts were dried and evaporated to give a white solid (5.96 g), which was chromatographed on silica (400 g). Elution with 0-7% methanol in dichloromethane gave a white powder (5.52 g, 63%)

δH (d$_6$-DMSO) 1.3-1.76 (17H, m), 3.17 (1H, br s), 4.95 (1H, s), 6.71 (1H, d), 7.0 (1H, s), and 7.14 (1H, s).

(g) Methyl 3-oxo-3,4-dihydro-2H-pyrido[3,2-b][1,4]thiazine-6-carboxylate

A solution of ethyl 2-mercaptoacetate (1.473 ml) in DMF (48 ml) was ice-cooled and treated with sodium hydride (540 mg of a 60% dispersion in oil). After 1 hour methyl 6-amino-5-bromopyridine-2-carboxylate (3 g) (T. R. Kelly and F. Lang, J. Org. Chem. 61, 1996, 4623-4633) was added and the mixture stirred for 16 hours at room temperature. The solution was diluted with EtOAc (1 liter), washed with water (3×300 ml), dried and evaporated to about 10 ml. The white solid was filtered off and washed with a little EtOAc to the ester (0.95 g).

MS (APCI⁻) m/z 223 ([M−H]⁻, 100%)

(h) 3-Oxo-3,4-dihydro-2H-pyrido[3,2-b][1,4]thiazine-6-carboxylic acid

A solution of ester (g) (788 mg) in dioxan (120 ml)/water (30 ml) was treated dropwise over 2 hours with 0.5M NaOH solution (8 ml) and stirred overnight. After evaporation to approx. 3 ml, water (5 ml) was added and 2N HCl to pH4. The precipitated solid was filtered off, washed with a small volume of water and dried under vacuum to give a solid (636 mg).

MS (APCI⁻) m/z 209 ([M−H]⁻, 5%), 165([M−COOH]⁻, 100%)

(i) 6-Hydroxymethyl-3-oxo-3,4-dihydro-2H-pyrido[3,2-b][1,4]thiazine

A solution of the carboxylic acid (h) (500 mg) in THF (24 ml) with triethylamine (0.396 ml) was cooled to −10° C. and isobutyl chloroformate (0.339 ml) added. After 20 minutes the suspension was filtered through kieselguhr into an ice-cooled solution of sodium borohydride (272 mg) in water (8 ml), the mixture stirred 30 minutes and the pH reduced to 7 with dilute HCl. The solvent was evaporated and the residue triturated under water. The product was filtered and dried under vacuum to give a white solid (346 mg).

MS (APCI⁻) m/z 195 ([M−H]⁻, 50%), 165(100%)

(j) 3-Oxo-3,4-dihydro-2H-pyrido[3,2-b][1,4]thiazine-6-carboxaldehyde

A solution of the alcohol (i) (330 mg) in dichloromethane (30 ml)/THF (30 ml) was treated with manganese dioxide (730 mg) and stirred at room temperature. Further manganese dioxide was added after 1 hour (730 mg) and 16 hours (300 mg). After a total of 20 hours the mixture was filtered through kieselguhr and the filtrate evaporated. The product was triturated with EtOAc/hexane (1:1) and collected to give a solid (180 mg).

(k) 7-Bromo-thieno[3,2-b]pyridine

A suspension of 4H-thieno[3,2-b]pyridin-4-one (5 g, 33.1 mmol) in DMF (35 ml) was treated at 0° C. with phosphorous tribromide (3.1 ml, 39.7 mmol). After 1 hour the mixture was added to a mixture of ice/saturated aqueous sodium hydrogen carbonate solution. Filtration and drying in vacuo afforded a pale yellow solid (5.9 g, 83%).

(l) [4-Hydroxy-4-(thieno[3,2-b]pyridin-7-ylcarbamoyl)-cyclohexyl]-carbamic acid tert-butyl ester A mixture of the amide (f) (387 mg, 1.5 mmol), cesium carbonate (0.61 g), tris(dibenzylideneacetone)dipalladium (0) (27 mg), and rac-2,2'-bis(diphenylphosphino)-1,1'-binaphthyl (56 mg) in dry dioxan (12 ml) under argon was sonicated for 10 minutes. Bromide (k) (321 mg, 1.5 mmol) was added, and the mixture was stirred and heated at 100° C. for 24 hours under argon. The mixture was cooled, centrifuged, then the supernatant evaporated and chromatographed on silica gel, eluting with dichloromethane, then 0-10% methanol in ethyl acetate affording a solid (495 mg, 840%).

MS (+ve ion electrospray) m/z 392 (MH+).

(m) 4-Amino-1-hydroxy-cyclohexanecarboxylic acid thieno[3,2-b]pyridin-7-ylamide

A solution of carbamate (1) (490 mg, 1.25 mmol) in dichloromethane (7.5 ml) was treated with trifluoroacetic acid (7.5 ml). After 2 hours the mixture was evaporated, azeotroping with toluene. The residue was partitioned between ethyl acetate and saturated aqueous sodium hydrogen carbonate solution. The organic extract was dried and evaporated affording a yellow solid (167 mg, 45%).

MS (+ve ion electrospray) m/z 292 (MH+).

(n) Title Compound

A mixture of amine (m) (167 mg, 0.57 mmol) and aldehyde (6) (111 mg, 0.57 mmol) in methanol/DMF/acetic acid (7 ml/7 ml/0.7 ml) was treated with 3 A molecular sieves and heated at 80° C. for 1.5 hours. The mixture was allowed to cool to room temperature then sodium cyanoborohydride (72 mg, 1.15 mmol) was addded. The mixture was stirred at room temperature overnight, acidified briefly with 5M hydrochloric acid (0.5 ml) then partitioned between ethyl acetate and saturated aqueous sodium hydrogen carbonate solution. The organic extract was dried and evaporated affording a yellow solid. The residue was chromatographed on silica eluting with a 0-20% methanol in ethyl acetate gradient affording the free base of the title compound as a white solid (171 mg, 71%).

$^1$H NMR δ(CD$_3$OD) 8.55 (1H, d), 7.96 (2H, m), 7.70 (1H, d), 7.50 (1H, d), 7.05 (1H, d), 3.90 (2H, s), 3.50 (2H, s), 2.70 (1H, m), 2.10-1.60 (8H, m)

MS (+ve ion electrospray) m/z 470 (MH+).

This material was dissolved in chloroform/methanol (3 ml/3 ml) and treated with 1M HCl in ether (2 ml) with vigorous shaking. The resulting white solid was isolated by centrifugation and dried under vacuum to provide the title compound (119 mg).

Example 2

1-Hydroxy-t-4-[(3-oxo-3,4-dihydro-2H-pyrido[3,2-b][1,4]thiazin-6-ylmethyl)-amino]-r-cyclohexanecarboxylic acid (2,3-dihydro-[1,4]dioxino[2,3-b]pyridin-8-yl)-amide dihydrochloride (cis-N-(2,3-dihydrol[1,4]dixoxino[2,3-b]pyridin-8-yl)-1-hydroxy-4-{[(3-oxo-3,4-dihydro-2H-pyrido[3,2-b][1,4]thiazin-6-yl)methyl]amino}cyclohexanecarboxamide hydrochloride)

(a) 8-Bromo-2,3-dihydro-[1,4]dioxino[2,3-b]pyridine

A solution of 2,3-dihydro-[1,4]dioxino[2,3-b]pyridine (prepared by the method of H. Neunhoffer et al, Chem., Ber., 1990, 123 (12), 2453) (1.37 g, 10 mmol) in tetrahydrofuran (20 ml) under argon at −78° C. was treated over 15 minutes with a solution of n-butyl lithium (20 mmol) in tetrahydrofuran (8 ml). After 30 minutes a solution of 1,2-dibromo-1,1,2,2-tetrafluoro-ethane (2.6 g, 10 mmol) in tetrahydrofuran (10 ml) was added dropwise over 5 minutes. After a further 30 minutes the cooling bath was removed and saturated aqueous ammonium chloride (20 ml) and ether (20 ml) were added. The mixture was allowed to warm to room temperature then partitioned between ether/water. The organic extract was washed with half-saturated brine, dried and evaporated. The residue was chromatographed on silica eluting with a 0-30% gradient of ethyl acetate in dichloromethane affording a yellow solid (1.1 g, 51%).

MS (+ve ion electrospray) m/z 217 (MH+).

(b) [4-(2,3-Dihydro-[1,4]dioxino[2,3-b]pyridin-8-ylcarbamoyl)-4-hydroxy-cyclohexyl]-carbamic acid tert-butyl ester This was prepared from bromide (a) (432 mg) and amide (1f) (516 mg) by the procedure of Example (11) affording a yellow solid after chromatography (105 mg, 13%).

MS (+ve ion electrospray) m/z 394 (MH+).

(c) 4-Amino-1-hydroxy-cyclohexanecarboxylic acid (2,3-dihydro-[1,4]dioxino[2,3-b]pyridin-8-yl)-amide This was prepared from carbamate (b) (105 mg) by the procedure of Example (1m) with the exception that the crude material was subjected to chromatography on silica eluting with a 0-30% methanol in ethyl acetate gradient affording an oil (25 mg, 32%).

MS (+ve ion electrospray) m/z 394 (MH+).

(d) Title Compound

This was prepared from amine (c) (25 mg) and aldehyde (1j) (16 mg) according to the procedure of Example (1n) affording the free base of the title compound as a white solid (4 mg, 10%).

$^1$H NMR δ(CD$_3$OD) 7.95 (1H, d), 7.75 (1H, d), 7.65 (1H, d), 7.07 (1H, d), 4.45 (2H, m), 4.38 (2H, m), 4.10 (2H, s), 3.52 (2H, s), 2.80 (1H, m), 2.10-1.60 (8H, m)

MS (+ve ion electrospray) m/z 472 (MH+).

The free base was converted into the dihydrochloride salt by the procedure of Example 1 affording a white solid (5 mg).

Example 3 trans-4-[(3-Oxo-3,4-dihydro-2H-pyrido[3,2-b][1,4]thiazin-6-ylmethyl)-amino]-cyclohexanecarboxylic acid quinolin-4-ylamide dihydrochloride (trans-4-{[(3,4-dihydro-2H-pyrdro[3,2-b][1,4]thiazin-6-yl)methyl]amino}-N-4-quinolinylincyclohexeanecarboxamide Hydrochloride)

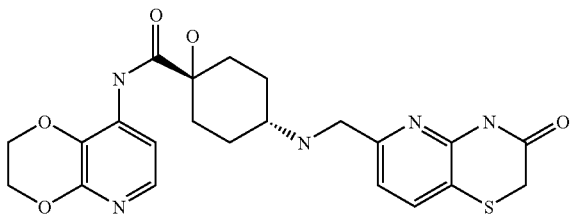

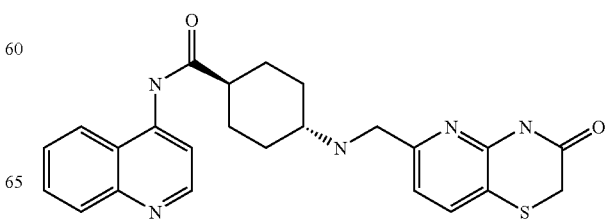

(a) trans-(4-Carbamoyl-cyclohexyl)-carbamic acid tert-butyl ester

A solution of trans-4-tert-butoxycarbonylamino-cyclohexanecarboxylic acid (15 g, 61.7 mmol) and 1-hydroxysuccinimide (76 g, 61.7 mmol) in ethyl acetate (200 ml) was treated with a solution of dicyclohexylcarbodiimide (12.7 g, 61.7 mmol) in ethyl acetate (50 ml). After stirring overnight the mixture was filtered and evaporated affording a yellow solid. This was redissolved in tetrahydrofuran (300 ml) and treated gaseous ammonia was bubbled through the solution for 15 minutes. Filtration afforded a white solid which was stirred in water (200 ml) for 1 hour. Filtration and drying afforded a white solid (11.3 g, 76%).

MS (+ve ion electrospray) m/z 243 (MH$^+$).

(b) trans-[4-(Quinolin-4-ylcarbamoyl)-cyclohexyl]-carbamic acid tert-butyl ester This was prepared from 4-chloroquinoline (0.49 g) and amide (a) (0.73 g) according to the procedure of Example (1I) affording a white solid (0.66 g, 60%).

MS (+ve ion electrospray) m/z 370 (MH$^+$).

(c) trans-4-Amino-cyclohexanecarboxylic acid quinolin-4-ylamide

This was prepared from carbamate (b) (0.65 g) according to the procedure of Example (1m) affording a white solid (280 mg, 58%).

MS (+ve ion electrospray) m/z 270 (MH+).

(d) Title Compound

This was prepared from amine (c) (220 mg) and aldehyde (1j) (160 mg) according to the procedure of Example (1n) affording the free base of the title compound as a white foam (104 mg, 27%).

$^1$H NMR δ(CDCl$_3$) 9.30 (1H, bs), 9.00 (1H, bs), 8.80 (1H, d), 8.20 (1H, d), 8.15 (1H, d), 8.05 (1H, d), 7.70 (1H, t), 7.60-7.50 (2H, m), 6.95 (1H, d), 3.90 (2H, s), 3.45 (2H, s), 2.70 (1H, m), 2.20-2.00 (4H, m), 1.80-1.70 (2H, m), 1.40-1.30 (2H, m)

MS (+ve ion electrospray) m/z 448 (MH+).

The free base was converted into the dihydrochloride salt by the procedure of Example 1 affording a white solid (110 mg).

Example 4 trans-4-[(3-Oxo-3,4-dihydro-2H-benzo[1,4]thiazin-6-ylmethyl)-amino]-cyclohexanecarboxylic acid isoquinolin-5-ylamide (N-5-isoquinolinyl-4-{[(3-oxo-3,4dihydro-2H-1,4-benzothiazin-6-yl)methyl]amino}cyclohexanecarboxamide)

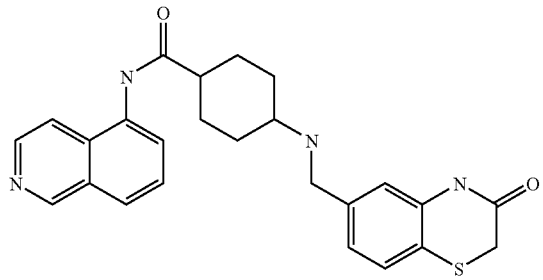

(a) 3-Oxo-3,4-dihydro-2H-benzo[1,4]thiazine-6-carboxylic acid

3-Oxo-3,4-dihydro-2H-benzo[1,4]thiazine-6-carboxylic acid methyl ester (6.74 g) was suspended in tetrahydrofuran (100 ml) and 2M sodium hydroxide (30 ml) was added followed by water (20 ml). The solution was stirred for 2.5 hours, evaporated to half volume and acidified with 2M hydrochloric acid. The product was collected, washed with water and dried in vacuo, to give a white solid (6.2 g).

MS (−ve ion electrospray) m/z 208 (M−H)$^-$

(b) 6-Hydroxymethyl-4H-benzo[1,4]thiazin-3-one

The acid (a) in tetrahydrofuran (50 ml) and triethylamine (4.7 ml) was cooled to 0° C. and isobutylchloroformate (4.02 ml) was added dropwise and the solution was stirred at 0° C. for 2 hours, when it was filtered into a stirred solution of sodium borohydride (3.14 g) in ice/water (50 ml). The mixture was stirred at 0° C. for 1 hour and allowed to warm to room temperature. It was acidified with 2M hydrochloric acid, evaporated to half volume, and the resulting product was collected, washed with water and dried in vacuo, to give a white solid (4.5 g).

MS (−ve ion electrospray) m/z 194 (M−H)$^-$

(c) 3-Oxo-3,4-dihydro-2H-benzo[1,4]thiazine-6-carboxaldehyde

A stirred solution of the alcohol (b) (3.5 g) in chloroform (150 ml) and tetrahydrofuran (300 ml) was treated with manganese dioxide (7.8 g) for 18 hours and was filtered and evaporated to give a white solid (2.5 g).

MS (−ve ion electrospray) m/z 194 (M−H)$^-$

(d) Title Compound

This was prepared from trifluoromethane sulphonic acid-isoquinolin-5-yl ester (prepared as in D. Ortwine et al, J. Med. Chem., 1992, 35 (8), 1345) and amide 3(a) by the same methodology as in Example 3, with the exception that aldehyde (c) was used in the final reductive alkylation step.

LC/MS: (ES) m/z 447 (M+H)$^+$.

Example 5

1-Hydroxy-t-4-[(3-oxo-3,4-dihydro-2H-pyrido[3,2-b][1,4]thiazin-6-ylmethyl)-amino]-r-cyclohexanecarboxylic acid (2-methoxy-quinolin-8-yl)-amide (cis-1-hydroxy-N-[2-(methyloxy)-8-quinolinyl]-4-{[3-oxo-3,4-dihydro-2H-pyrido[3,2-b]n [1,4]thiazin-6-yl)methyl]amino}cyclohexanecarboxamide)

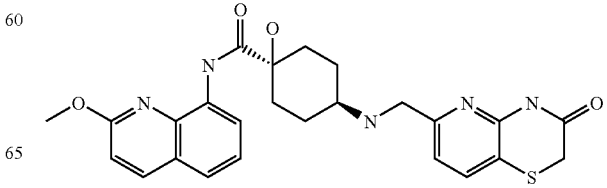

(a) 8-Benzyloxyquinolin-2-ol

This was prepared by a slight modification of the procedure of Guo et al, Tet Lett, 1999, 40, 6999. To a stirred solution of 2,8-quinolinediol (4.97 g, 30.84 mmol) and 1,8-diazabicylo[5.4.0]undec-7-ene (DBU) (40.2 mmol, 6 mL) in isopropyl alcohol (60 mL) was added benzyl bromide (3.7 mL, 30.84 mmol). The solution was heated at reflux overnight. The reaction mixture was allowed to cool and then concentrated in vacuo. The resulting residue was diluted with $CH_2Cl_2$ and washed with 0.5 N NaOH, 10% HCl and water and dried over $Na_2SO_4$. Concentration provided 6 g (77%) of a tan solid, which was used without further purification.

LC/MS: (ES) m/z 252 (M+H)$^+$.

(b) 8-Benzyloxy-2-methoxyquinoline

8-Benzyloxyquinolin-2-ol (a) (6 g, 23.9 mmol) was added to $POCl_3$ (45 mL) and heated with stirring at 80° C. for 10 hours. The reaction was allowed to cool to room temperature and the excess $POCl_3$ was decomposed by slowly pouring the mixture into water at 30° C. The product was then extracted into toluene and the combined organic layers were washed with saturated aqueous $NaHCO_3$ and dried over $MgSO_4$. Concentration provided 6.9 g of a colorless oil which was dissolved in toluene (10 mL) and added to a stirred 25 wt % solution of NaOMe in MeOH (50 mL). The reaction solution was heated overnight at 70° C. After cooling to room temperature, the reaction solution was poured onto ice and extracted with toluene. The combined organic extracts were dried ($MgSO_4$) and concentrated in vacuo to give a colorless oil (6.14 g, 92%).

LC/MS: (ES) m/z 266 (M+H)$^+$.

(c) 1,1,1-Trifluoromethanesulfonic acid 2-methoxyquinolin-8-yl ester

8-Benzyloxy-2-methoxyquinoline (b) (6.14 g, 23 mmol) was dissolved in EtOH (50 mL) and treated with 10% Pd/C (600 mg). The reaction mixture was hydrogenated under an $H_2$ atmosphere (20 psi) in a Parr shaker apparatus for 3.5 hours. The reaction was filtered and concentrated to give 3.8 g (96%) of a colorless oil. This was dissolved in DMF (40 mL) and treated with triethylamine (3.6 mL, 25.8 mmol) and N-phenyltrifluoromethanesulfonimide (8.54 g, 23.9 mmol). The reaction mixture was heated with stirring at 40° C. for 8 hours. Upon cooling to room temperature, aqueous $K_2CO_3$ solution was added and the product was extracted into $CH_2Cl_2$. The combined organic extracts were washed with water (5×75 mL), dried ($Na_2SO_4$) and concentrated to give 6.8 g (100%) of a light tan crystalline solid.

LC/MS: (ES) m/z 308 (M+H)$^+$.

(d) [r-4-Hydroxy-4-(2-methoxyquinolin-8-ylcarbamoyl)-c-cyclohexyl]carbamic acid tert-butyl ester A flask containing amide (1f) (847 mg, 3.28 mmol), rac-2,2'-bis(diphenylphosphino)-1,1'-binaphthyl (133 mg, 0.21 mmol) and $Cs_2CO_3$ (1.33 g, 4.1 mmol) in dioxane (30 mL) was flushed with $N_2$. To this was added $Pd_2(dba)_3$ (63 mg, 0.07 mmol) and the reaction solution was sonicated for 10 min as the color changed from purple to brown. A solution of 1,1,1-trifluoromethanesulfonic acid 2-methoxyquinolin-8-yl ester (c) (1.09 g, 3.54 mmol) in dioxane (15 mL) was then added. The reaction mixture was heated with stirring at 100° C. for 18 hours. Upon cooling to room temperature, the reaction mixture was filtered through celite® and concentrated. The product was purified on an ISCO Combiflash® automated column chromatography unit (silica, 0% to 10% MeOH/EtOAc) to provide 846 mg (65%) of the desired product as a pale yellow solid.

LC/MS: (ES) m/z 416 (M+H)$^+$.

(e) t-4-Amino-1-hydroxy-r-cyclohexanecarboxylic acid (2-methoxyquinolin-8-yl)amide dihydrochloride A solution of (d) (134 mg, 0.32 mmol) in $CH_2Cl_2$ (10 mL) was cooled to 0° C. To this was added 4M HCl/dioxane (1.57 mL, 6.28 mmol) in one portion and the reaction solution was stirred at room temperature for 5 hours. The reaction solution was filtered and the solids washed with ether and dried under vacuum to provide a pale yellow solid (65 mg).

LC/MS: (ES) m/z 316 (M+H)$^+$.

(f) Title Compound

The dihydrochloride salt (e) (55 mg, 0.14 mmol), aldehyde (1j) (50 mg, 0.25 mmol), triethylamine (0.10 mL, 0.72 mmol), DMF (0.5 mL), HOAc (0.5 mL) and MeOH (7 mL) were combined together and stirred in the presence of 3A molecular sieves for 3 hours at 80° C. and then at room temperature overnight. $NaCNBH_3$ (54 mg, 0.86 mmol) was added and the reaction mixture was stirred at room temperature for 24 hours. The reaction mixture was diluted with 10% MeOH/$CHCl_3$ and aq $Na_2CO_3$ was added. The aqueous layer was extracted with 10% MeOH/$CHCl_3$ (4×) and the combined organic extracts were dried ($Na_2SO_4$). The product was purified on an ISCO Combiflash® automated column chromatography unit (silica, 0% to 10% MeOH/$CHCl_3$) to provide 31 mg (45%) of the title compound as a white solid.

$^1$H NMR (400 MHz) δ 1.80-2.10 (m, 8H), 3.10 (m, 1H), 3.51 (s, 2H), 4.09 (s, 3H), 4.18 (s, 2H), 6.95-6.98 (d, 1H), 7.04-7.07 (d, 1H), 7.30-7.35 (t, 1H), 7.48-7.50 (d, 1H), 7.73-7.75 (d, 1H), 8.09-8.11 (d, 1H), 8.56-8.58 (d, 1H).

LC/MS: (ES) m/z 494 (M+H)$^+$.

Example 6

4-[(3,4-Dihydro-2H-pyrido[3,2-b][1,4]thiazin-6-ylmethyl)-amino]-1-hydroxy-cyclohexanecarboxylic acid (2-methoxy-quinolin-8-yl)-amide (cis-4-[(3,4-dihydro-2H-pyrido[3,2-b][1,4]thiazin-6-ylmethyl) amino]-1-hydroxy-N-[2-methyloxy)-8-quinolinyl] cyclohexanecarboxamide)

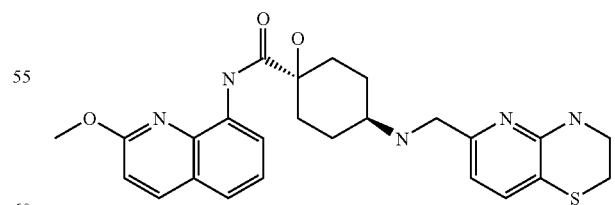

(a) (3,4-Dihydro-2H-pyrido[3,2-b][1,4]thiazine-6-yl)-methanol

A solution of methyl 3-oxo-3,4-dihydro-2H-pyrido[3,2-b][1,4]thiazine-6-carboxylate (1 g) (1.0 g) in dry tetrahydrofuran (170 ml) was treated with a 1M solution of lithium aluminium hydride in ether (14 ml) and the mixture was heated under reflux for 18 hours. It was cooled and a slight excess of 2N sodium hydroxide was added followed by chloroform and anhydrous sodium sulphate and the mixture was stirred for 30 minutes and filtered. The solution was evaporated to dryness to give a semi-solid (0.482 g).

MS (APCI$^+$) m/z 183 (MH$^+$).

(b) 3,4-Dihydro-2H-pyrido[3,2-b][1,4]thiazine-6-carboxaldehyde

The alcohol (a) (0.482 g) in dry dichloromethane (50 ml) was stirred with manganese dioxide (1.2 g) for 18 hours and the mixture was filtered. The filtrate was evaporated and chomatographed on silica gel, eluting with methanol-dichloromethane (1:50) to afford a yellow solid (0.24 g).

MS (APCI$^+$) m/z 181 (MH$^+$)

(c) Title Compound

Dihydrochloride salt (5e) (65 mg, 0.16 mmol), aldehyde (b) (75 mg, 0.42 mmol), triethylamine (0.15 mL, 1.08 mmol), DMF (0.5 mL), HOAc (0.5 mL) and MeOH (7 mL) were combined together and stirred in the presence of 3 A molecular sieves for 3 hours at 80° C. and then at room temperature overnight. NaCNBH$_3$ (47 mg, 0.75 mmol) was added and the reaction mixture was stirred at room temperature for 24 hours. The reaction mixture was diluted with 10% MeOH/CHCl$_3$ and aq Na$_2$CO$_3$ was added. The aqueous layer was extracted with 10% MeOH/CHCl$_3$ (4×) and the combined organic extracts were dried (Na$_2$SO$_4$). The product was purified on an ISCO Combiflasht® automated column chromatography unit (silica, 0% to 10% MeOH/CHCl$_3$) to provide 70 mg (92%) of the title compound as a pale yellow solid.

$^1$H NMR (400 MHz) δ 1.77-2.08 (m, 8H), 2.71 (m, 1H), 2.89-2.91 (m, 2H), 3.66-3.67 (m, 2H), 3.76 (s, 2H), 4.00 (s, 3H), 5.38 (br s, 1H), 6.40-6.42 (d, 1H), 6.81-6.83 (d, 1H), 7.08-7.10 (d, 1H), 7.24-7.28 (t, 1H), 7.33-7.35 (d, 1H), 7.87-7.89 (d, 1H), 8.61-8.63 (d, 1H) 10.92 (s, 1H).

LC/MS: (ES) m/z 480 (M+H)$^+$.

Example 7

6-({4-Hydroxy-4-[2-(2-methoxy-quinolin-8-yl)-ethyl]-cyclohexylamino}-methyl)-4H-pyrido[3,2-b][1,4]oxazin-3-one (6-{[(cis-4hydroxyl-4-{2-[2-(methyloxy)-8-quinolinyl]ethyl}cyclohexyl)amino]methyl}-2H-pyrido[3,2-b][1,4]oxazin-3(4H)-one)

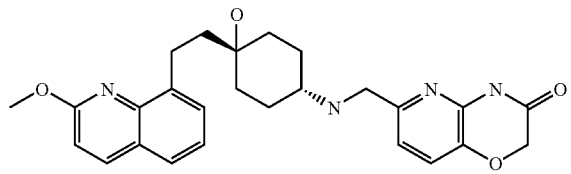

(a) (r-4-Hydroxy-4-trimethylsilanyl-c-cyclohexyl)carbamic acid tert-butyl ester

A stirred solution of trimethylsilyl acetylene at −78° C. (4.14 g, 0.042 mol) in THF (60 mL) was treated with n-butyl lithium (29 mL, 0.042 mol; 1.6 M solution in THF). The resulting mixture was stirred at −78° C. for 15 min. A solution of N-4-Boc-aminocyclohexanone (3 g, 0.014 mol) in THF (120 mL) was added dropwise over a period of 30 min. The resulting mixture was stirred at −78° C. for 1 hour and then allowed to slowly warm to room temperature over 1 hour. The reaction was quenched with a saturated aqueous solution of ammonium chloride, diluted with EtOAc and washed with saturated aqueous NaHCO$_3$ solution, H$_2$O, and saturated aqueous NaCl solution. The organic extract was dried over MgSO$_4$ and concentrated to yield the title compound as an off-white foam (4.38 g, 100%).

MS (ES) m/z 312 (M+H)$^+$.

(b) (t-4-Ethynyl-4-hydroxy-r-cyclohexyl)carbamic acid tert-butyl ester

A solution of (a) (4.38 g, 0.014 mol) in MeOH (50 mL) was treated with K$_2$CO$_3$ (5.83 g, 0.42 mol) and stirred at room temperature for 3 hours. The solvent was removed in vacuo and the residue was partitioned between EtOAc and aqueous NaCl, and the organic layer was dried (MgSO$_4$) and concentrated to yield an oil (2.7 g, 89%).

MS (ES) m/z 240 (M+H)$^+$.

(c) [r-4-Hydroxy-4-(2-methoxyquinoline-8-ylethynyl)-c-cyclohexyl]carbamic acid tert-butyl ester A solution of (b) (500 mg, 2.09 mmol) and triflate (5c) (656 mg, 2.13 mmol) in a 1:1 mixture of triethylamine and DMF (10 mL total volume) was treated with (Ph$_3$P)$_2$PdCl$_2$ (60 mg; 4% mol) and CuI (32 mg, 8% mol). The resulting mixture was heated with stirring at 70° C. for 24 hours. The solvent was removed under reduced pressure and the residue was partitioned between CH$_2$Cl$_2$ and aqueous NaCl, and the organic layer was dried (MgSO$_4$), and concentrated in vacuo. The resulting oil was purified by flash column chromatography on silica gel (gradient: 20-50% EtOAc/hexane) to afford a yellow foam (635 mg, 82%). LC/MS: MS (ES) m/z 397 (M+H)$^+$.

(d) {r-4-Hydroxy-4-[2-(2-methoxyquinolin-8-yl)ethyl]-c-cyclohexyl}carbamic acid tert-butyl ester A solution of (c) (635 mg, 1.6 mmol) in MeOH (10 mL) was treated with 10% Pd/C (65 mg) and hydrogenated in a Parr bottle for 6 h at 40 psi. The solution was filtered through a plug of celite®, and the filter pad was washed with MeOH. The filtrate was concentrated to yield the title compound (608 mg, 95%) as a light yellow foam.

LC/MS: (ES) m/z 401 (M+H)$^+$.

(e) t-4-Amino-r-1-[2-(2-methoxyquinolin-8-yl)ethyl]cyclohexanol trifluoroacetate A stirred solution of (d) (600 mg, 1.5 mmol) in CH$_2$Cl$_2$ (5 mL) was treated with trifluoroacetic acid (1.16 mL, 15 mmol). The solution was allowed to stir for 1 hour at room temperature and then concentrated under reduced pressure. MeOH was added and the solution was again concentrated to afford a solid (1.06 g)

LC/MS: (ES) m/z 301 (M+H)$^+$.

(f) 2-Bromo-5-hydroxy-6-nitropyridine

3-Hydroxy-2-nitropyridine (20 g, 0.143 mole) was dissolved in methanol (400 mL) and a solution of 25% sodium methoxide in methanol (33 mL, 0.13 mole) was added at room temperature. The mixture was stirred for 30 min, then was cooled to 0° C., and bromine (7.2 mL, 0.14 mole) was added slowly. The reaction was then stirred at 0° C. for 30 min, then was quenched with glacial AcOH (2.5 mL). The solvent was removed in vacuo to afford material (30 g, 96%), which was used without further purification.

MS (ES) m/z 219.0 (M+H)+.

(g) Ethyl (6-bromo-2-nitro-pyridin-3-yloxy)acetate

The hydroxypyridine (f) (30 g, 0.14 mole) was suspended in acetone (200 mL), and potassium carbonate (39 g, 0.28 mole) was added, followed by ethyl bromoacetate (15.7 mL, 0.14 mmole). The reaction was heated at reflux for 10 hr, then was cooled to room temperature and diluted with $Et_2O$. The precipitate was removed by suction filtration, and the filtrate was concentrated in vacuo to afford material (38 g, 89%), which was used without further purification.

MS (ES) m/z 305.0 (M+H)+.

(h) 6-Bromo-4H-pyrido[3,2-b][1,4]oxazin-3-one

The nitropyridine (g) (38 g, 0.125 mole) was dissolved in glacial AcOH (150 mL), and iron powder (20 g, 0.36 mole) was added. The mixture was mechanically stirred and heated at 90° C. for 5 hr, then was cooled to room temperature and diluted with EtOAc (300 mL). The mixture was filtered through a pad of silica gel and the filtrate was concentrated in vacuo and the residue recrystallized from MeOH (15 g, 52%).

MS (ES) m/z 229.0 (M+H)+.

(i) 6-((E)-Styryl)-4H-pyrido[3,2-b][1,4]oxazin-3-one

The bromopyridine (h) (6.0 g, 26.3 mmole) and trans-2-phenylvinylboronic acid (3.9 g, 26.3 mmole) were dissolved in 1,4-dioxane (150 mL) and the solution was degassed with argon. $(Ph_3P)_4Pd$ (230 mg, 0.2 mmole) was added, followed by a solution of potassium carbonate (6.9 g, 50 mmole) in $H_2O$ (20 mL). The reaction was heated at reflux under argon overnight, then was cooled to room temperature and diluted with EtOAc (200 mL). The solution was washed sequentially with $H_2O$ and brine, dried ($Na_2SO_4$), and concentrated in vacuo. The solid residue was purified by flash chromatography on silica gel (5-10% EtOAc/$CHCl_3$) to afford a solid (2.5 g, 38%).

MS (ES) m/z 253.0 (M+H)+.

(j) 3-Oxo-3,4-dihydro-2H-pyrido[3,2-b][1,4]oxazine-6-carboxaldehyde

The pyridine (i) (1.2 g, 4.8 mmole) was dissolved in $CH_2Cl_2$ (200 mL) and the solution was cooled to −78° C. Ozone was bubbled through the solution with stirring until a pale blue color appeared, then the excess ozone was removed by bubbling oxygen through the solution for 15 min. Dimethylsulfide (1.76 mL, 24 mmole) was added to the solution, and the reaction was stirred at −78° C. for 3 hr, then at room temperature overnight. The solvent was removed in vacuo, and the residue was triturated with $Et_2O$ (50 mL). The collected solid was washed with additional $Et_2O$ and dried to afford a solid (700 mg, 82%).

MS (ES) m/z 179.0 (M+H)+.

(k) Title Compound

Amine trifluoroacetate (e) (270 mg, 0.51 mmol) was added to a stirred solution of aldehyde 0) (100 mg, 0.561 mmol) dissolved in DMF (3 mL) and MeOH (2 mL). $NaHCO_3$ (214 mg, 2.55 mmol) was added to the reaction mixture and the solution was allowed to stir at 80° C. for 16 hours. The solution was cooled to 0° C. and sodium borohydride (0.042 g, 1.12 mmol) was added. The reaction was stirred at ambient temperature for 4 hours. The reaction mixture was partitioned between ethyl acetate and water. The organic layer was washed with water (2x) and brine, dried ($Na_2SO_4$) and concentrated. Purification using flash column chromatography on silica gel (90:10:1 $CHCl_3$/MeOH/$NH_4OH$) provided the title compound (92 mg, 39%) as a light yellow foam.

$^1$H NMR (400 MHz, $CDCl_3$) δ 7.95 (d, 1H); 7.55 (d, 1H); 7.48 (d, 1H); 7.29 (t, 1H); 7.18 (d, 1H); 6.93 (d, 1H); 6.88 (d, 1H); 4.61 (s, 2H); 4.06 (s, 3H); 3.86 (s, 2H); 3.25 (m, 2H); 2.52 (m, 1H); 1.89 (m, 2H); 1.79 (m, 2H); 1.76 (m, 2H); 1.59 (m, 2H); 1.43 (m, 2H).

LC/MS: (ES) m/z 465 (M+H)+

Example 8

6-({4-Hydroxy-4-[2-(2-methoxy-quinolin-8-yl)-ethyl]-cyclohexylamino}-methyl)-4H-pyrido[3,2-b][1,4]thiazin-3-one (6-{[(cis-4-hydroxy-4-{2-[2-(methloxy)-8-quinolinyl]ethyl}cyclohexyl)amino]methyl}-2H-pyrido[3,2-b][1,4]thiazin-3(4H)-one)

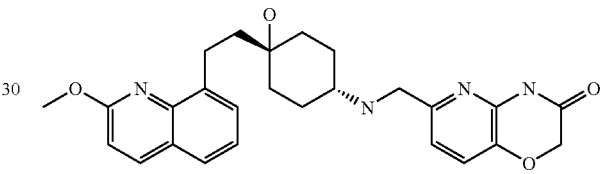

The title compound was prepared in 57% purified yield according to the method described for (7k) above, substituting the carboxaldehyde with 3-oxo-3,4-dihydro-2H-pyrido[3,2-b][1,4]thiazine-6-carboxaldehyde (1j) affording a light yellow foam.

$^1$H NMR (400 MHz, $CDCl_3$) δ 7.95 (d, 1H); 7.55 (d, 1H); 7.48 (d, 1H); 7.29 (t, 1H); 7.18 (d, 1H); 6.93 (d, 1H); 6.88 (d, 1H); 4.61 (s, 2H); 4.06 (s, 3H); 3.86 (s, 2H); 3.25 (m, 2H); 2.52 (m, 1H); 1.89 (m, 2H); 1.79 (m, 2H); 1.76 (m, 2H); 1.59 (m, 2H); 1.43 (m, 2H).

LC/MS: (ES) m/z 479 (M+H)+

Example 9

(1R,3S,4R)-3-Hydroxy-4-[(3-oxo-3,4-dihydro-2H-pyrido[3,2-b][1,4]oxazin-6-ylmethyl)-amino]-cyclohexanecarboxylic acid (2-cyano-quinolin-8-yl)-amide hydrochloride ((1R,S,4R)-N-(2-cyano-8quinolinyl)-3-hydroxy-4-{[(3-oxo-3,4-dihydro-2H-pytido[3,2-b][1,4]oxazin-6-yl)methyl] amino}cyclohexanecarboxamide hydrochloride)

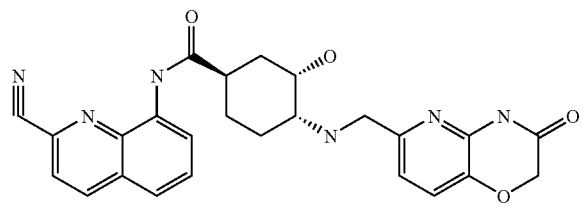

(a) (1R,4S,5R)-4-Bromo-6-oxabicyclo[3.2.1]octan-7-one (R)-Cyclohex-3-enecarboxylic acid, 98.2% e.e, (2.30 g, 18.2 mmol) [Schwartz et al, J. Am. Chem. Soc., 100, 5199, (1978)] was reacted with trimethylsilyl bromide (3.01 mL, 22.8 mmol), DMSO (1.62 mL) and N,N-diisopropylethylamine (3.97 mL, 22.8 mmol) [by the method of Iwata et al, Heterocycles., 31, 987 (1990)] to give a white solid, (2.13 g, 57%).

$\delta_H$ (CDCl$_3$) 1.68 (1H, m), 1.86 (1H, d), 1.98-2.02 (1H, m), 2.20 (1H, m), 2.42 (1H, m), 2.50-2.56 (1H, m), 2.73 (1H, br s), 4.15 (1H, dd), 4.91 (1H, d).

(b) (1R,3R,4S)-4-Bromo-3-hydroxy-cyclohexanecarboxylic acid amide (1R,4S,5R)-4-Bromo-6-oxabicyclo[3.2.1]octan-7-one (a) (2.13 g, 10.4 mmol) was taken up in THF (20 mL) and treated with 0.88 ammonia (5.3 mL) at 20° C. for 24 hours with stirring. The solvent was then removed in vacuo to give a white solid (2.31 g).

$\delta_H$ (CD$_3$OD) 1.63 (1H, dd), 1.73-1.80 (1H, m), 1.85-2.03 (3H, m), 2.16-2.21 (1H, m), 2.36 (1H, tt), 3.54 (1H, dt), 4.55 (1H, bs)

(c) (1R,3R,4R)-4-Azido-3-hydroxy-cyclohexanecarboxylic acid amide (1R,3R,4S)-4-Bromo-3-hydroxy-cyclohexanecarboxylic amide (b) (2.31 g, 10.4 mmol) was treated with sodium azide (1.35 g, 20.8 mmol) in DMF (100 mL) at 60° C. for 15.5 hours. The solvent was removed in vacuo and the residue purified by flash column chromatography (Silica gel, DCM:MeOH 0-10%) to give a white solid (1.09 g, 5.93 mmol, 57%).

$\delta_H$ (CD$_3$OD) 1.30 (1H, dq), 1.42-1.56 (2H, m), 1.83 (1H, dt), 1.99-2.08 (2H, m), 2.30 (1H, tt), 3.16 (1H, m), 3.41 (1H, m)

(d) (1R,3R,4R)-4-Amino-3-hydroxy-cyclohexanecarboxylic acid amide, acetate salt To (1R,3R,4R)-4-azido-3-hydroxy-cyclohexanecarboxylic acid amide (c) (765 mg, 4.15 mmol) in MeOH/AcOH (9:1, 30 mL) was added Pd/C (10%, 300 mg), and the mixture stirred under hydrogen at atmospheric pressure for 22 hours. The mixture was filtered through Celite®, the residue washed with MeOH, and the combined organic extracts concentrated in vacuo to give a white solid (905 mg, 100%).

$\delta_H$ (CD$_3$OD) 1.42-1.59 (3H, m), 1.87-1.92 (1H, m), 1.92 (3H, s), 2.07-2.14 (2H, m), 2.37 (1H, m), 2.84 (1H, dt), 3.50 (1H, dt).

(e) (1R,3R,4R)-3-Hydroxy-4-tert-butoxycarbonylamino-cyclohexanecarboxylic acid amide (1R,3R,4R)-4-Amino-3-hydroxy-cyclohexanecarboxylic acid amide, acetate salt (d) (905 mg, 4.15 mmol) was treated with N,N-diisopropylethylamine (868 µL, 4.98 mmol) and di-tert-butyl-dicarbonate (1.08 g, 4.98 mmol) in dioxane (30 mL) and MeOH (50 mL) for 16 hours. The solvent was then removed in vacuo and the residue purified by flash column chromatography (silica gel, DCM:MeOH 0-10%) to give a white solid (804 mg, 3.11 mmol, 75%).

$\delta_H$ (CD$_3$OD) 1.18-1.32 (1H, m), 1.44 (9H, s), 1.43-1.55 (2H, m), 1.81 (1H, d), 1.98 (1H, bd), 2.09 (1H, d), 2.29 (1H, m), 3.22 (1H, dt), 3.33 (1H, dt).

(f) 4-Nitrobenzoic acid (1S,2R,5R)-2-tert-butoxycarbonylamino-5-carbamoyl-cyclohexyl ester To (1R,3R,4R)-3-hydroxy-4-tert-butoxycarbonylamino-cyclohexanecarboxylic acid amide (e) (2.78 g, 10.8 mmol), para-nitrobenzoic acid (2.16 g, 12.9 mmol) and triphenylphosphine (3.38 g, 12.9 mmol) in dry THF (200 mL) and DMF (25 mL) under argon was added dropwise diisopropyl azodicarboxylate (2.5 mL, 12.9 mmol) at 0° C. After 5 min at 0° C. and 17 hours at room temperature, the mixture was concentrated in vacuo and the residue purified by flash column chromatography (silica gel, DCM/MeOH, 0-4%) to give a white solid (2.36 g, 5.8 mmol, 54%).

$\delta_H$ (CD$_3$OD/CDCl$_3$) 1.41 (9H, s), 1.62-1.74 (1H, m), 1.80-1.92 (3H, m), 1.98-2.03 (1H, m), 2.18-2.22 (1H, m), 2.58-2.66 (1H, m), 3.64-3.73 (1H, m), 5.55 (1H, br s), 8.31 (2H, d), 8.35 (2H, d)

m/z (ES$^+$) 430 (MNa$^+$).

(g) (1R,3S,4R)-3-Hydroxy-4-tert-butoxycarbonylamino-cyclohexanecarboxylic acid amide 4-Nitrobenzoic acid (1S,2R,5R)-2-tert-butoxycarbonylamino-5-carbamoyl-cyclohexyl ester (i) (3.62 g, 8.9 mmol) in dry MeOH (250 mL) was treated with potassium carbonate (1.84 g, 13.3 mmol). After 2 hours at room temperature, the mixture was concentrated and the residue purified by flash column chromatography (silica gel, DCM/MeOH, 5-15%) to give a white solid (1.62 g, 6.3 mmol, 71%).

$\delta_H$ (CD$_3$OD) 1.44 (9H, s), 1.45-1.55 (1H, m), 1.62-1.72 (3H, m), 1.82-1.88 (1H, m), 1.89-1.94 (1H, m), 2.53-2.62 (1H, m), 3.37-3.43 (1H, m), 3.97-3.99 (1H, m)

m/z (ES$^+$) 281 (MNa$^+$).

(h) 1,1,1-Trifluoro-methanesulfonic acid 2-cyano-quinolin-8-yl ester

A solution of 8-hydroxy-quinoline-2-carbonitrile (5 g, 29.4 mmol) in dichloromethane (50 mL) was treated with triethylamine (4.5 mL) then N-phenyltrifluoromethanesulfonimide (11.5 g, 32.3 mmol). After 18 h the mixture was washed with water, saturated aqueous sodium chloride solution, dried and evaporated. Chromatography on silica eluting with an ethyl acetate/petrol gradient afforded a white solid (8.0 g, 90%).

MS (+ve ion electrospray) m/z 303 (MH$^+$).

(i) [(1R,2S,4R)-4-(2-Cyano-quinolin-8-ylcarbamoyl)-2-hydroxy-cyclohexyl]-carbamic acid tert-butyl ester This was prepared from amide (g) (1.7 g) and triflate (h) (2.0 g) by the method of Example (11). Chromatography on silica eluting with 0-5% methanol in dichloromethane afforded a white solid (2.4 g, 89%).

MS (+ve ion electrospray) m/z 411 (MH$^+$).

(j) (1R,3S,4R)-4-Amino-3-hydroxy-cyclohexanecarboxylic acid (2-cyano-quinolin-8-yl)-amide A solution of carbamate (i) (2.4 g, 6 mmol) in dichloromethane (50 mL) was treated with trifluoroacetic acid (10 mL). After 18 hours the mixture was evaporated and partitioned between saturated aqueous sodium bicarbonate solution and 20% methanol/dichloromethane. The aqueous phase was twice more extracted and the combined extracts dried and evaporated giving a solid. This was triturated with ether/ethyl acetate (1/1) and filtered, washing with ether, to afford a light brown solid (1.25 g, 61%).

MS (+ve ion electrospray) m/z 311 (MH+).

(k) Title Compound

Amine (j) (0.59 g, 1.9 mmol) and aldehyde (7j) (0.36 g, 2 mmol) were reacted together with sodium cyanoborohydride (0.16 g, 2.5 mmol) according to the procedure of Example (1n) affording, after workup and chromatography, the free base of the title compound as a white solid (0.48 g, 54%).

$^1$H NMR δ(CDCl$_3$) 9.95 (1H, bs), 8.85 (1H, d), 8.28 (1H, d), 7.75 (1H, d), 7.65 (1H, d), 7.52 (1H, d), 7.25 (1H, d), 6.92 (1H, d), 4.65 (2H, s), 4.30 (1H, bs), 4.00 (2H, m), 3.05 (1H, m), 2.90 (1H, m), 2.35 (1H, m), 2.10 (1H, m), 1.90-1.80 (3H, m), 1.70 (1H, m)

MS (+ve ion electrospray) m/z 473 (MH+).

This material was converted into the hydrochloride salt by the method of Example (1) affording the title compound as a white solid (0.38 g).

Example 10

1-Hydroxy-t-4-[(3-oxo-3,4-dihydro-2H-pyrido[3,2-b][1,4]thiazin-6-ylmethyl)-amino]-r-cyclohexanecarboxylic acid (2-cyano-quinolin-8-yl)-amide dihydrochloride (cis-N-(2-cyano-8-quinolinyl)-1-hydroxy-4-} [(3-oxo-3,4-dihydro-2H-pyrido[3,2-b][1,4] thiazan-6yl)methyl [amino═cyclohexanecarboxamide hydrochloride)

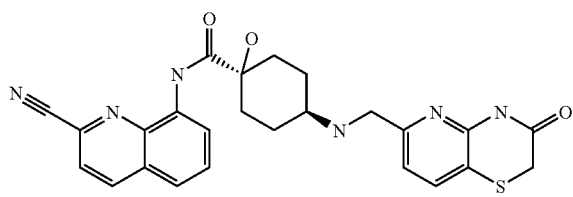

(a) [4-(2-Cyano-quinolin-8-ylcarbamoyl)-4-r-hydroxy-c-cyclohexyl]-carbamic acid tert-butyl ester This was prepared from amide (1f) and triflate (9h) according to the procedure for Example (11) affording a solid.

MS (+ve ion electrospray) m/z 411 (MH+).

(b) t-4-Amino-1-hydroxy-r-cyclohexanecarboxylic acid (2-cyano-quinolin-8-yl)-amide This was prepared from carbamate (a) by the procedure of Example (1m).

MS (+ve ion electrospray) m/z 311 (MH+).

(c) Title Compound

Amine (b) (0.1 g, 0.32 mmol) and aldehyde (1j) (0.06 g, 0.32 mmol) were reacted together with sodium cyanoborohydride (0.1 g) according to the procedure of Example (1n) affording, after workup and chromatography, the free base of the title compound as a white solid (0.09 g, 56%).

$^1$H NMR δ(CDCl$_3$) 11.00 (1H, bs), 8.90 (1H, d), 8.28 (1H, d), 7.72 (1H, d), 7.66 (1H, t), 7.55 (2H, m), 6.95 (1H, d), 3.93 (2H, s), 3.50 (2H, s), 2.70 (1H, m), 2.30-1.90 (6H, m), 1.70 (2H, m)

MS (+ve ion electrospray) m/z 489 (MH+).

This material was converted into the dihydrochloride salt by the method of Example (1) affording the title compound as a white solid (0.09 g).

Example 11

1-Hydroxy-t-4-[(3-oxo-3,4-dihydro-2H-pyrido[3,2-b][1,4]oxazin-6-ylmethyl)-amino]-r-cyclohexanecarboxylic acid (2-cyano-quinolin-8-yl)-amide hydrochloride cis-N-(2-cyano-8-quinolinyl)-1-hydroxy-4-} [(3-oxo-3,4-dihydro-2H-pyrido[3,2-b][1,4]thiazan-6yl)methyl[amino═cyclohexanecarboxamide hydrochloride)

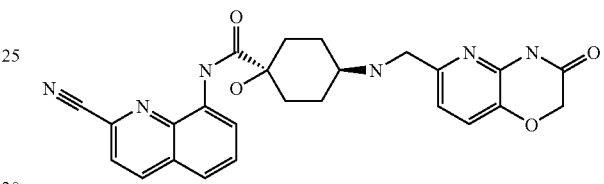

This was prepared from amine (10b) (0.62 g) and aldehyde (7j) (0.36 g) according to the reductive alkylation procedure of Example (1n) affording, after workup and chromatography, the free base of the title compound as a white solid (0.28 g, 30%).

$^1$H NMR δ(CDCl$_3$) 11.00 (1H, bs), 8.85 (1H, d), 8.25 (1H, d), 7.70 (1H, d), 7.60 (1H, t), 7.50 (1H, d), 7.20 (1H, d), 6.95 (1H, d), 4.65 (2H, s), 3.95 (2H, s), 2.75 (1H, m), 2.20-1.90 (6H, m), 1.80 (2H, m)

MS (+ve ion electrospray) m/z 473 (MH+).

This material was converted into the hydrochloride salt by the method of Example (1) affording the title compound as a white solid (0.23 g).

Example 12

(1S,3R,4S)-3-Hydroxy-4-[(3-oxo-3,4-dihydro-2H-pyrido[3,2-b][1,4]thiazin-6-ylmethyl)-amino]-cyclohexanecarboxylic acid (2-cyano-quinolin-8-yl)-amide hydrochloride ((1S,3R,4S)-N-(2-cyano-8-quinolinyl)-3-hydroxy-4-{[(3-oxo-3,4-dihydro-2H-pyrido[3,2-b][1,4]thiazin-6-yI)methyl]amino}cyclohexanecarboxamide hydrochloride)

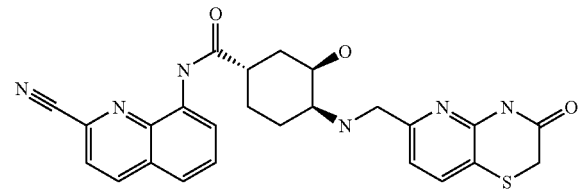

(a) (1S,3R,4S)-4-Amino-3-hydroxy-cyclohexanecarboxylic acid 2-cyano-quinolin-8-yl)-amide This was prepared from (S)-cyclohex-3-enecarboxylic acid [Schwartz et al, J. Am. Chem. Soc., 100, 5199, (1978)] by the analogous chemistry used to prepare amine (9j).

MS (+ve ion electrospray) m/z 311 (MH+).

(b) Title Compound

This was prepared from amine (a) (310 mg) and aldehyde (1j) (194 mg) by the reductive alkylation procedure of Example (1n) affording, after workup and chromatography, the free base of the title compound as a white solid (247 mg).

¹H NMR δ(CD₃OD) 8.70 (1H, d), 8.47 (1H, d), 7.85 (1H, d), 7.75-7.65 (3H, m), 7.05 (1H, d), 4.30 (1H, bs), 4.15 (1H, d), 4.05 (1H, d), 3.52 (2H, s), 3.10 (1H, m), 2.97 (1H, m), 2.25 (1H, m), 2.15 (1H, m), 2.00-1.80 (3H, m), 1.70 (1H, m)

MS (+ve ion electrospray) m/z 489 (MH+).

This material was converted into the hydrochloride salt by the method of Example (1) affording the title compound as a white solid (0.25 g).

Example 13

(1S,3R,4S)-3-Hydroxy-4-[(3-oxo-3,4-dihydro-2H-pyrido[3,2-b][1,4]oxazin-6-ylmethyl)-amino]-cyclohexanecarboxylic acid (2-cyano-quinolin-8-yl)-amide hydrochloride ((1S3R4S)-N-(2-cyano-8-quinolinyl)-3-hydroxy-4-{[(3-oxo-3,4-dihydro-2H-pyrido[3,2-b][1,4]oxazin-6-yl)methyl]amino}cyclohexanecarboxamide hydrochloride)

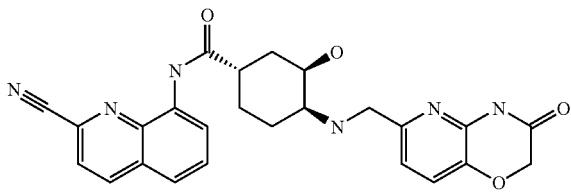

This was prepared from amine (12a) (310 mg) and aldehyde (7j) (180 mg) by the reductive alkylation procedure of Example (1n) affording, after workup and chromatography, the free base of the title compound as a white solid (241 mg).

¹H NMR δ(CD₃OD) 8.75 (1H, d), 8.52 (1H, d), 7.92 (1H, d), 7.72 (2H, m), 7.30 (1H, m), 7.05 (1H, d), 4.65 (2H, s), 4.30 (1H, m), 4.00 (1H, d), 3.95 (1H, d), 3.15 (1H, m), 2.95 (1H, m), 2.00-1.80 (3H, m), 1.70 (2H, m)

MS (+ve ion electrospray) m/z 473 (MH+).

This material was converted into the hydrochloride salt by the method of Example (1) affording the title compound as a white solid (0.17 g).

Example 14

(1R,3R,4R)-3-Hydroxy-4-[(3-oxo-3,4-dihydro-2H-pyrido[3,2-b][1,4]thiazin-6-ylmethyl)-amino]-cyclohexanecarboxylic acid (2-cyano-quinolin-8-yl)-amide hydrochloride ((1R,3R4R)-N-(2-cyano-8-quinolinyl)-3-hydroxy-4-{[(3-oxo-3,4-dihydro-2H-pyrido[3,2-b][1,4thiazin-6-yl)methyl]amino}cyclohexanecarboxamide hydrochloride)

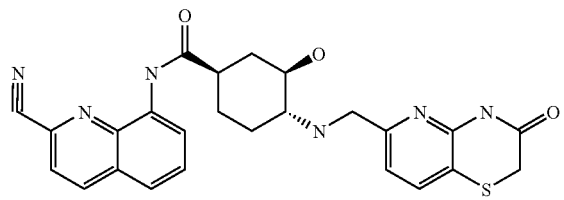

(a) [(1R,2R,4R)-4-(2-Cyano-quinolin-8-ylcarbamoyl)-2-hydroxy-cyclohexyl]-carbamic acid tert-butyl ester This was prepared from amide (9e) (1.7 g) and triflate (9h) (2.0 g) by the method of Example (11). Chromatography on silica eluting with 2-5% methanol in dichloromethane afforded a white solid (2.0 g, 74%).

MS (+ve ion electrospray) m/z 411 (MH+).

(b) (1R,3R,4R)-4-Amino-3-hydroxy-cyclohexanecarboxylic acid 2-cyano-quinolin-8-yl)-amide A solution of carbamate (a) (2.0 g, 6 mmol) in dichloromethane (50 mL) was treated with trifluoroacetic acid (10 mL). After 18 hours the mixture was evaporated and partitioned between saturated aqueous sodium bicarbonate solution and 20% methanol/dichloromethane. The aqueous phase was twice more extracted and the combined extracts dried and evaporated giving a brown solid. This was chromatographed on silica eluting with 0-30% methanol in dichloromethane affording a white solid (1.3 g, 84%).

MS (+ve ion electrospray) m/z 311 (MH+).

(c) Title Compound

This was prepared from amine (b) (630 mg) and aldehyde (1j) (388 mg) by the reductive alkylation procedure of Example (1n) affording, after workup and chromatography, the free base of the title compound as a white solid (636 mg, 65%).

¹H NMR δ(CDCl₃) 9.52 (1H, bs), 8.85 (1H, d), 8.28 (1H, d), 7.70 (1H, d), 7.65-7.55 (2H, m), 7.50 (1H, d), 6.95 (1H, d), 4.25 (1H, d), 4.00 (1H, d), 3.85 (1H, m), 3.40 (1H, q), 2.85 (1H, m), 2.70 (1H, m), 2.40 (1H, m), 2.28 (1H, m), 2.15 (1H, m), 1.85-1.50 (3H, m)

MS (+ve ion electrospray) m/z 489 (MH+).

This material was converted into the hydrochloride salt by the method of Example (1) affording the title compound as a white solid (0.51 g).

Example 15

(1R,3R,4R)-3-Hydroxy-4-[(3-oxo-3,4-dihydro-2H-pyrido[3,2-b][1,4]thiazin-6-ylmethyl)-amino]-cyclohexanecarboxylic acid (2-cyano-quinolin-8-yl)-amide hydrochloride ((1R,3R,4R)-N-(2-cyano-8-quinolinyl)-3-hydroxy-4-{[(3-oxo-3-dihydro-2H-pyrido[3,2-b][1,4oxazin-6-yI)methyI]amino}cyclohexanecarboxamide hydrochloride)

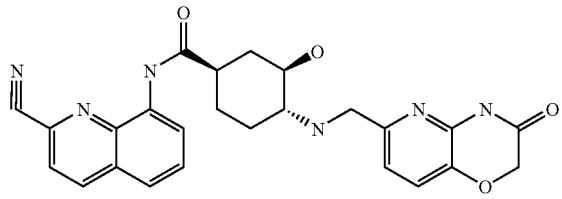

This was prepared from amine (14b) (630 mg) and aldehyde (7j) (360 mg) by the reductive alkylation procedure of Example (1n) affording, after workup and chromatography, the free base of the title compound as a white solid (575 mg, 61%).

$^1$H NMR δ(CDCl$_3$) 9.55 (1H, bs), 8.85 (1H, d), 8.28 (1H, d), 7.72 (1H, d), 7.65 (1H, t), 7.52 (1H, d), 7.20 (1H, d), 6.90 (1H, d), 4.60 (2H, s), 4.18 (1H, d), 3.95 (1H, d), 3.75 (1H, m), 2.75 (2H, m), 2.40 (1H, m), 2.27 (1H, m), 2.15 (1H, m), 1.85-1.65 (2H, m), 1.55 (1H, m).

MS (+ve ion electrospray) m/z 473 (MH+).

This material was converted into the hydrochloride salt by the method of Example (1) affording the title compound as a white solid (0.43 g).

Example 16

(1R,3S,4R)-3-Hydroxy-4-[(3-oxo-3,4-dihydro-2H-pyrido[3,2-b][1,4]thiazin-6-ylmethyl)-amino]-cyclohexanecarboxylic acid (2-cyano-quinolin-8-yl)-amide hydrochloride((1R,3S,4R)-N-(2-cyano-8-quinolinyl)-3-hydroxy-4-{[(3-oxo-3,4-dihydro-2H-pyrido[3,2-b][1,4]thiazin-6-yI)methyI]amino}cycIohexanecarboxamide hydrochloride)

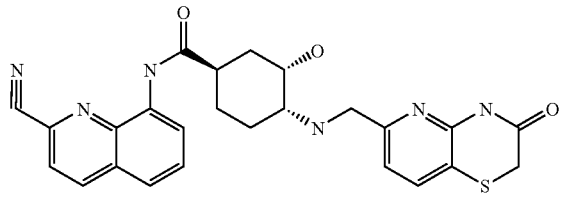

This was prepared from amine (9j) (590 mg) and aldehyde (1j) (388 mg) by the reductive alkylation procedure of Example (1n) affording, after workup and chromatography, the free base of the title compound as a white solid (488 mg, 52%).

$^1$H NMR (CDCl$_3$) 9.60 (1H, bs), 8.90 (1H, d), 8.30 (1H, d), 7.75 (1H, d), 7.68 (1H, t), 7.58 (1H, d), 7.52 (1H, d), 6.92 (1H, d), 4.15 (1H, m), 3.95 (1H, d), 3.85 (1H, d), 3.50 (2H, s), 3.00 (1H, m), 2.75 (1H, m), 2.35 (1H, m), 2.10 (2H, m), 1.90-1.70 (3H, m).

MS (+ve ion electrospray) m/z 489 (MH+).

This material was converted into the hydrochloride salt by the method of Example (1) affording the title compound as a white solid (0.40 g).

Example 17

1-Hydroxy-t-4-[(3-oxo-3,4-dihydro-2H-pyrido[3,2-b][1,4]oxazin-6 ylmethyl)-amino]-r-cyclohexanecarboxylic acid (2-methoxy-quinolin-8-yl)-amide(cis-1-hydroxy-N-[2-(methyloxy)-8-quinolinyl]-4-{[(3-oxo-3,4-dihydro-2 H-pyrido[3,2-b][1,4]oxazin-6-yI)methyl]amino}cyclohexanecarboxamide)

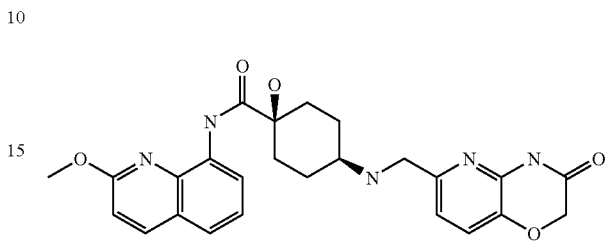

This was prepared from amine dihydrochloride (5e) (140 mg) and aldehyde (7j) (80 mg) by the reductive alkylation procedure of Example (5f) affording, after workup and chromatography, the title compound as a white solid (92 mg).

$^1$H NMR δ (CD$_3$OD) 8.60 (1H, d), 8.10 (1H, d), 7.50 (1H, d), 7.35 (1H, t), 7.20 (1H, d), 6.90 (2H, m), 4.65 (2H, s), 4.10 (3H, s), 3.95 (2H, s), 2.75 (1H, m), 2.20-1.90 (6H, m), 1.80 (2H, m)

LC/MS: (ES) m/z 478 (M+H)$^+$.

Example 18

1-Hydroxy-t-4-[(3-oxo-3,4-dihydro-2H-pyrido[3,2-b][1,4]oxazin-6-ylmethyl)-amino]-r-cyclohexanecarboxylic acid (2-methyl-quinolin-8-yl)-amide dihydrochloride (cis-1-hydroxy-N-(2-methyl-8-quinoIinyI)-4-{[(3-oxo-3,4-dihydro-2H-pyrido[3,2-b][1,4]oxazin-6-yI)methyl]amino}cycIohexanecarboxamide hydrochloride)

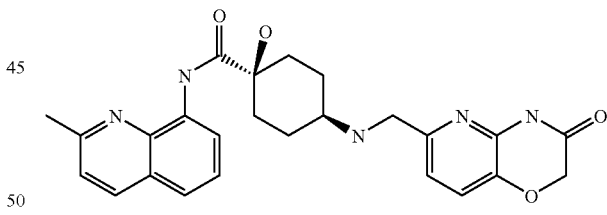

(a) 1,1,1-Trifluoro-methanesulfonic acid 2-methyl-quinolin-8-yl ester

This was prepared from 2-methyl-quinolin-8-ol (7.1 g) by the procedure of Example (9h) affording a clear oil (13.4 g, 100%).

MS (+ve ion electrospray) m/z 292 (MH+).

(b) {r-4-Hydroxy-4-[2-methylquinolin-8-ylcarbamoyl]-c-cyclohexyl}carbamic acid tert-butyl ester This was prepared from triflate (a) (1.0 g) and amide (1f) (0.9 g) according to the procedure for Example (1l) with the difference that 9,9-dimethyl-4,5bis(diphenylphosphino)xanthene (XANTPHOS) was used in place of BINAP, affording, after workup and chromatography, a white solid (1.1 g, 79%).

MS (+ve ion electrospray) m/z 400 (MH+).

(c) t-4-Amino-1-hydroxy-r-cyclohexanecarboxylic acid (2-methylquinolin-8-yl)amide This was prepared from carbamate (b) (1.1 g) by the same procedure as for Example (1m) affording a pale yellow solid (0.74 g, 91%).

MS (+ve ion electrospray) m/z 300 (MH+).

(d) Title Compound

This was prepared from amine (c) (100 mg) and aldehyde (7j) (54 mg) by the reductive alkylation procedure of Example (1n) affording, after workup and chromatography, the free base of the title compound as a white solid (34 mg, 25%).

$^1$H NMR δ(CDCl$_3$) 11.20 (1H, bs), 8.72 (1H, d), 7.95 (1H, d), 7.30 (2H, m), 7.25-7.15 (2H, m), 6.95 (1H, d), 4.65 (2H, s), 3.95 (2H, s), 2.75 (1H, m), 2.65 (3H, s), 2.20-1.85 (8H, m).

MS (+ve ion electrospray) m/z 462 (MH+).

This material was converted into the dihydrochloride salt by the method of Example (1) affording the title compound as a white solid (44 mg).

Example 19

1-Hydroxy-t-4-[(3-oxo-3,4-dihydro-2H-pyrido[3,2-b][1,4]thiazin-6-ylmethyl)-amino]-r-cyclohexanecarboxylic acid (2-methyl-quinolin-8-yl)-amide dihydrochloride (cis-1-hydroxy-N-(2-methyl-8-quinolinyl)-4-{[(3-oxo-3,4-dihydro-2H-pyrido[3,2-b][1,4]thiazin-6-yl)methyl]amino}cyclohexanecarboxamide hydrochloride)

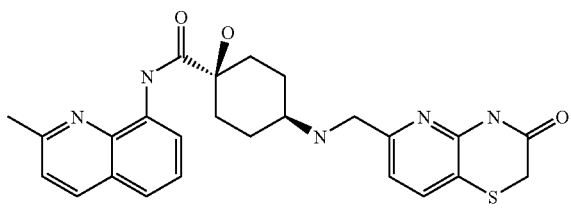

This was prepared from amine (18c) (100 mg) and aldehyde (1j) (64 mg) by the reductive alkylation procedure of Example (1n) affording, after workup and chromatography, the free base of the title compound as a white solid (88 mg, 56%).

$^1$H NMR δ(CDCl$_3$) 11.20 (1H, bs), 8.75 (1H, d), 8.00 (1H, d), 7.58 (1H, d), 7.40 (2H, m), 7.30 (1H, m), 6.98 (1H, d), 3.95 (2H, s), 3.50 (2H, s), 2.75 (1H, m), 2.70 (3H, s), 2.20-1.85 (8H, m).

MS (+ve ion electrospray) m/z 478 (MH+).

This material was converted into the dihydrochloride salt by the method of Example (1) affording the title compound as a white solid (96 mg).

Example 20

(1R,3R,4R)-3-Hydroxy-4-[(3-oxo-3,4-dihydro-2H-pyrido[3,2-b][1,4]thiazin-6-ylmethyl)-amino]-cyclohexanecarboxylic acid (2-methoxy-quinolin-8-yl)-amide dihydrochloride ((1R,3R,4R)-3-hydroxy-N-[2-(methyloxy)-8-quinolinyl]-4-{[(3-oxo-3,4-dihydro-2H-pyrido[3,2-b][1,4]thiazin-6-yl)methyl]amino}cyclohexanecarboxamide hydrochloride)

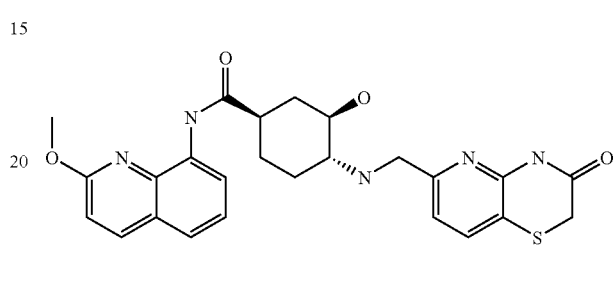

(a) [(1R,2R,4R)-2-Hydroxy-4-(2-methoxy-quinolin-8-ylcarbamoyl)-cyclohexyl]-carbamic acid tert-butyl ester This was prepared from triflate (5c) (700 mg) and amide (9e) (620 mg) according to the procedure of Example (5d) affording the product as a solid (550 mg, 58%).

MS (+ve ion electrospray) m/z 416 (MH+).

(b) (1R,3R,4R)-4-Amino-3-hydroxy-cyclohexanecarboxylic acid (2-methoxy-quinolin-8-yl)-amide This was prepared from carbamate (a) (550 mg) according to the procedure of Example (9j) affording a white solid (253 mg).

MS (+ve ion electrospray) m/z 316 (MH+).

(c) Title Compound

This was prepared from amine (b) (76 mg) and aldehyde (1j) (47 mg) by the reductive alkylation procedure of Example (1n) affording, after workup and chromatography, the free base of the title compound as a white solid (50 mg).

$^1$H NMR δ(CDCl$_3$) 9.55 (1H, bs), 8.68 (1H, d), 8.00 (1H, d), 7.55 (1H, d), 7.45-7.35 (2H, m), 6.92 (2H, m), 4.10 (3H, s), 4.05 (1H, d), 3.85 (1H, d), 3.50 (1H, m), 3.40 (2H, s), 2.50-2.35 (3H, m), 2.20 (2H, m), 1.80-1.55 (2H, m), 1.30 (1H, m)

MS (+ve ion electrospray) m/z 494 (MH+).

This material was converted into the dihydrochloride salt by the method of Example (1) affording the title compound as a pale yellow solid (57 mg).

Example 21

7-({r-4-Hydroxy-4-[2-(2-methoxy-quinolin-8-yl)-ethyl]-c-cyclohexylamino}-methyl)-1H-pyrido[2,3-b][1,4]thiazin-2-one (7-{[(cis-4-hydroxy-4-{2-[2-(methyloxy)-8-quinolinyl]ethyl}cyclohexyl)amino]methyl}-1H-pyrido[2,3-b][1[thiazin-2(3H)-one)

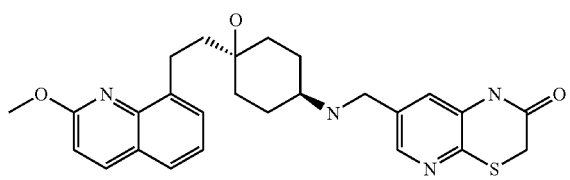

(a) 6-Methoxycarbonylmethylsulfanyl-5-nitro-nicotinic acid methyl ester

A solution of 6-chloro-5-nitro-nicotinic acid methyl ester (1.0 g) [prepared as described by A. H. Berrie et al. *J. Chem. Soc.* 2590-2594 (1951)] in dichloromethane (10 mL) containing triethylamine (0.76 mL) was treated with mercapto-acetic acid methyl ester (0.44 mL) and the solution was stirred at room temperature for 1 hour and evaporated to dryness. Sodium bicarbonate solution was added and the mixture was extracted with dichloromethane, dried (anhydrous sodium sulfate) and evaporated to afford a solid (11.0 g).

MS (+ve ion electrospray) m/z 287 (MH+).

(b) 2-Oxo-2,3-dihydro-1H-pyrido[2,3-b][1,4]thiazine-7-carboxylic acid methyl ester The ester (a) (1.0 g) in acetic acid (50 mL) was treated with iron powder (10 g) and the mixture was stirred and heated at 60° C. for 1 hour, cooled and filtered. The filtrate was evaporated, treated with sodium bicarbonate solution and extracted with warm chloroform. It was dried (anhydrous sodium sulfate) and evaporated to give a white solid (0.85 g).

MS (+ve ion electrospray) m/z 225 (MH+).

(c) 2-Oxo-2,3-dihydro-1H-pyrido[2,3-b][1,4]thiazine-7-carboxylic acid

The ester (b) (2.8 g) was hydrolysed with aqueous sodium hydroxide then acidified with 2M HCl and filtered to afford a solid (2.5 g) by the method of Example (1 h).

MS (−ve ion electrospray) m/z 209 (M−H⁻).

(d) 7-Hydroxymethyl-1H-pyrido[2,3-b][1,4]thiazin-2-one

The carboxylic acid (c) (2.48 g) was reacted with isobutylchloroformate and sodium borohydride by the method of Example (1i) to afford a solid (1.3 g), after recrystallisation from chloroform-methanol (9:1).

MS (+ve ion electrospray) m/z 197 (MH+).

(e) 2-Oxo-2,3-dihydro-1H-pyrido[2,3-b][1,4]thiazine-7-carboxaldehyde

The alcohol (d) (1.22 g) was oxidised with manganese dioxide by the method of Example (1j) to afford a solid (0.7 g).

MS (−ve ion electrospray) m/z 193 (M−H⁻).

(f) Title Compound

This was prepared from amine trifluoroacetate (7e) (0.68 g) and aldehyde (e) (0.25 g) by the reductive alkylation procedure of Example (7k) affording, after workup and chromatography, the title compound as a white solid (0.31 g).

MS (+ve ion electrospray) m/z 479 (MH+).

$^1$H NMR δ (CDCl$_3$) 8.10 (1H, s), 7.95 (1H, d), 7.53 (1H, d), 7.45 (1H, m), 7.35 (1H, t), 7.20 (1H, s), 6.90 (1H, d), 4.15 (3H, s), 3.85 (2H, s), 3.55 (2H, s), 3.25 (m, 2H); 2.52 (m, 1H); 1.80 (m, 2H), 1.70-1.40 (m, 8H).

Example 22

1-Hydroxy-t-4-[(2-oxo-2,3-dihydro-1H-pyrido[3,4-b][1,4]oxazin-7-ylmethyl)-amino]-r-cyclohexanecarboxylic acid (2-methyl-quinolin-8-yl)-amide dihydrochloride (cis-1-hydroxy-N-(2-methyl-8-quinolinyl)-4-{[(2-oxo-2,3-dihydro-1H-pyrido[3,4-b][1,4oxazin-7-yl)methyl [amino}cyclohexanecarboxamide hydrochloride)

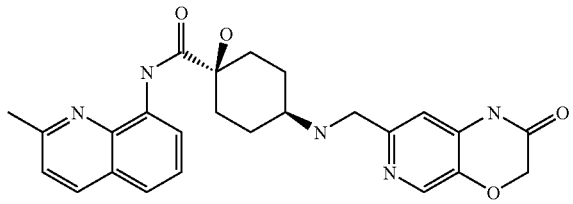

(a) 5-Hydroxy-2-methylpyridine N-oxide

5-Hydroxy-2-methylpyridine (25 g) was suspended in chloroform (500 ml) and treated with m-chloroperbenzoic acid (57 g of material described by the manufacturer as 57-86% pure). After stirring for 1 hour the solution was dried with MgSO$_4$ and poured onto a silica column. Elution with EtOAc to remove byproducts and then with 20-50% EtOH in EtOAc gave a solid (27.7 g).

MS (APCI⁺) m/z 126 (MH⁺).

(b) 5-Methoxycarbonylmethoxy-2-methylpyridine N-oxide

A solution of the pyridine N-oxide (a) (21.12 g) in DMF (450 ml) was treated with potassium carbonate (26.2 g) then, after 30 minutes, with methyl bromoacetate (16 ml), and stirred overnight. Solvent was evaporated, saturated brine (500 ml) added and the mixture extracted with chloroform (6×200 ml). The combined organic solution was dried and evaporated and the residue chromatographed (20% EtOH in EtOAc) to give a solid (18.5 g).

MS (APCI+) m/z 198 (H+).

(c) 5-Carboxymethoxy-2-methyl-4-nitropyridine N-oxide

The pyridine N-oxide (b) (18.5 g) was dissolved in a cold mixture of fuming nitric acid (90 ml) and concentrated sulfuric acid (90 ml) and heated to 40° C. for 1 hour, then 65° C. overnight. The mixture was cooled, poured onto ice and EtOAc (250 ml) added. When the ice had melted, the mixture was shaken and solid filtered off The EtOAc was dried and evaporated, the residue triturated with ether and filtered affording a solid (8.4 g).

MS (+ve ion electrospray) m/z 229 (MH+).

(d) 5-Methoxycarbonylmethoxy-2-methyl-4-nitropyridine N-oxide

The carboxylic acid (c) (8.4 g) in DMF (100 ml) was treated with potassium carbonate (7.6 g) and iodomethane (2.8 ml) and stirred for 3 days. After evaporation of solvent, water (200 ml) was added and the solid filtered off and dried under vacuum to give the product (5.32 g).

MS (+ve ion electrospray) m/z 243 (MH$^+$).

(e) 5-Methoxycarbonylmethoxy-4-nitro-2-trifluoro-acetoxymethylpyridine

The pyridine N-oxide (d) (3.8 g) in trifluoroacetic anhydride (120 ml) was refluxed under argon for 24 hours, the solvent evaporated and the residue partitioned between chloroform and aqueous NaHCO$_3$ (50 ml each). The aqueous fraction was re-extracted with chloroform (3×50 ml) and the combined organic solution dried and evaporated to give the product (1.8 g).

MS (+ve ion electrospray) m/z 339 (MH$^+$)

(f) Mixture of 5-methoxycarbonylmethoxy-4-nitro-2-trifluoroacetoxymethylpyridine and 2-hydroxymethyl-5-methoxycarbonylmethoxy-4-nitropyridine When material (e) was chromatographed on silica gel, partial loss of trifluoroacetyl group occurred to give the product mixture.

(g) 7-Acetoxymethyl-2-oxo-2,3-dihydro-1H-pyrido[3,4-b][1,4]oxazine

The mixture of nitropyridines (f) (7.37 mmole) in acetic acid (55 ml) was treated with iron powder (4.2 g) and stirred at 60° C. for 1 hour, cooled and filtered through kieselguhr. The filtrate was heated to 110° C. overnight, evaporated to dryness and partitioned between chloroform and aqueous NaHCO$_3$ (100 ml each). After filtration to remove iron salts and separation of the layers, the aqueous fraction was re-extracted with chloroform (10×50 ml) and the combined organic solution dried and evaporated to give product (1.17 g).

MS (−ve ion electrospray) m/z 221 ([M−H]$^-$).

(h) 7-Hydroxymethyl-2-oxo-2,3-dihydro-1H-pyrido[3,4-b][1,4]oxazine

A solution of acetate (g) (1.17 g) in dioxan (75 ml)/water (15 ml) was treated dropwise with 2M NaOH solution (3 ml) and left overnight. The mixture was acifiied to pH6 with dilute HCl and the solvent evaporated. Water (5 ml) was added and the solid filtered off and dried under vacuum to give product (877 mg).

MS (−ve ion electrospray) m/z 179 ([M−H]$^-$).

(i) 2-Oxo-2,3-dihydro-1H-pyrido[3,4-b][1,4]oxazine-7-carboxaldehyde

A mixture of the hydroxymethyloxazinone (h) (584 mg), manganese dioxide (2.3 g), THF (50 ml) and 1,2-dichloroethane (50 ml) was heated at 60° C. under argon for 20 hours. Filtration through kieselguhr and evaporation of solvent gave a solid which was triturated under EtOAc/hexane 1:3, filtered off and dried (383 mg).

MS (−ve ion electrospray) m/z 177 ([M−H]$^-$).

(j) Title Compound

This was prepared from amine (18c) (100 mg) and aldehyde (i) (54 mg) by the method of Example (1n) affording, after workup and chromatography the free base of the title compound as a white solid (62 mg, 45%). This material was converted into the dihydrochloride salt by the method of Example (1) affording the title compound as a white solid (60 mg).

MS (+ve ion electrospray) m/z 462 (MH+).

$^1$H NMR (dihydrochloride salt) δ (d6-DMSO) 11.35 (1H, bs), 11.25 (1H, bs), 9.05 (2H, bs), 8.70 (1H, d), 8.30 (1H, d), 8.22 (1H, s), 7.62 (1H, d), 7.50 (2H, m), 6.98 (1H, s), 6.20 (1H, bs), 4.75 (2H, s), 4.25 (2H, s), 3.20 (1H, m), 2.75 (3H, s), 2.05-1.80 (8H, m).

Example 23 t-4-[(7-Fluoro-3-oxo-3,4-dihydro-2H-pyrido[3,2-b][1,4]thiazin-6-ylmethyl)-amino]-1-hydroxy-r-cyclohexanecarboxylic acid (2-methoxy-quinolin-8-yl)-amide dihydrochloride (cis-4-{[(7-fluoro-3-oxo-3,4-dihydro-2H-pyrido[3,2-b][1,4]thiazin-6-yI)methyl]amino}-1-hydroxy-N-[2-(methyloxy)-8-quinolinyl[cyclohexanecarboxamide hydrochloride)

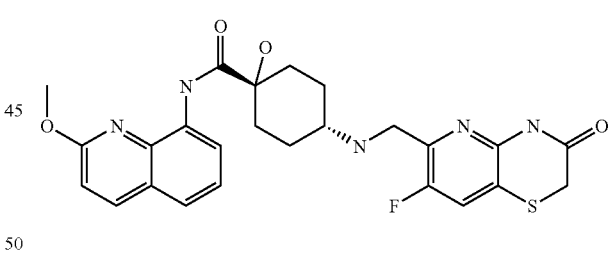

(a) 6-Amino-5-bromo-3-fluoro-pyridine-2-carboxylic acid methyl ester

A mixture of 6-amino-5-bromo-pyridine-2-carboxylic acid methyl ester (19.8 g) (T. R. Kelly and F. Lang, *J. Org. Chem.* 61, 1996, 4623-4633) and 1-chloromethyl-4-fluoro-1,4-diazoniabicyclo[2.2.2]octane bis(tetrafluoroborate) (Selectfluor™), (34.3 g) in acetonitrile (340 ml) under argon was heated to 40° C. for 1 hour, 60° C. for 1 hour and then 80° C. overnight. After partitioning between EtOAc and water (500 ml each) the aqueous fraction was re-extracted with EtOAc (300 ml) and the combined organic solution dried with MgSO$_4$ and evaporated. Chromatography (20% then 30% EtOAc in hexane) afforded the product (2.09 g).

MS (+ve ion electrospray) m/z 249 and 251 (MH$^+$).

(b) 6-Amino-5-ethoxycarbonylmethylthio-3-fluoro-pyridine-2-carboxylic acid methyl ester A solution of ethyl mercaptoacetate (1.15 ml) in DMF (40 ml) was ice-cooled under argon, treated with sodium hydride (420 mg of a 60% dispersion in oil) and stirred until all was in solution (about 1 hour). The ester (a) (2.48 g) was added, the mixture allowed to warm to room temp. and stirred overnight. EtOAc (150 ml) was added, the solution washed with water (3×150 ml), dried and evaporated. Chromatography of the residue (40% EtOAc in hexane) gave an oil (1.7 g).

MS (+ve ion electrospray) m/z 289 (MH+)

(c) Methyl 7-fluoro-3-oxo-3,4-dihydro-2H-pyrido[3,2-b][1,4]thiazine-6-carboxylate A solution of the fluoropyridine (b) (1.7 g) in acetic acid (100 ml) was heated at 110° C. overnight, evaporated and dried under vacuum to give the product as a white solid (1.5 g).

MS (+ve ion electrospray) m/z 243 (MH$^+$).

(d) 7-Fluoro-3-oxo-3,4-dihydro-2H-pyrido[3,2-b][1,4]thiazine-6-carboxylic acid This compound was prepared from the ester (c) by the method of Example (1 h) (86%).

(e) 7-Fluoro-6-hydroxymethyl-3-oxo-3,4-dihydro-2H-pyrido[3,2-b][1,4]thiazine This compound was prepared from carboxylic acid (d) by the method of Example (1i) (73%).

MS (−ve ion electrospray) m/z 213 ([M−H]$^-$)

(f) 7-Fluoro-3-oxo-3,4-dihydro-2H-pyrido[3,2-b][1,4]thiazine-6-carboxaldehyde A mixture of the alcohol (e) (971 mg), manganese dioxide (3.72 g), THF (70 ml) and 1,2-dichloroethane (70 ml) was heated at 60° C. under argon for 20 hours. Filtration through kieselguhr and evaporation of solvent gave a solid which was triturated with EtOAc/hexane 1:3 and collected by filtration (608 mg).

MS (+ve ion electrospray) m/z 213 (MH$^+$)

(g) Title Compound

This was prepared from amine dihydrochloride (5e) (100 mg) and aldehyde (f) (60 mg) by the method of Example (5f) affording, after workup and chromatography, the free base of the title compound as a white solid (70 mg).

$^1$H NMR δ (CD$_3$OD) 8.65 (1H, d), 8.05 (1H, d), 7.55-7.45 (2H, m), 7.35 (1H, t), 6.95 (1H, d), 4.15 (3H, s), 3.95 (2H, s), 3.50 (2H, s), 2.60 (1H, m), 2.10 (2H, m), 2.00-1.80 (4H, m), 1.65 (2H, m).

MS (+ve ion electrospray) m/z 512 (MH+).

This material was converted into the dihydrochloride by the method of Example (1) affording a white solid (78 mg).

Example 24 t-4-[(7-Chloro-3-oxo-3,4-dihydro-2H-pyrido[3,2-b][1,4]thiazin-6-ylmethyl)-amino]-1-hydroxy-r-cyclohexanecarboxylic acid (2-methoxy-quinolin-8-yl)-amide dihydrochloride(cis-4-{[(7-chloro-3-oxo-3,4-dihydro-2H-pyrido[3,2-b][1,4]thiazin-6-yl)methyl]amino}-1-hydroxy-N-[2-(methyloxy)-8-quinolinyl [cyclohexanecarboxamide hydrochloride)

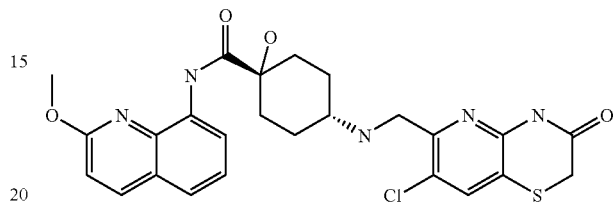

(a) Methyl 6-amino-5-bromo-3-chloropyridine-2-carboxylate

To a solution methyl 6-amino-5-bromopyridine-2-carboxylate (20.04 g) in acetic acid (900 ml) was added N-chlorosuccinimide (14 g) and the resultant solution was heated to 120° C. for 1 hour. The solution was then evaporated and treated with excess aqueous sodium bicarbonate and extracted with dichloromethane. The organic fraction was dried and evaporated to give the product (21.98 g).

MS (+ve ion electrospray) m/z 265 and 267 (MH$^+$)

(b) Methyl 7-chloro-3-oxo-3,4-dihydro-2H-pyrido[3,2-b][1,4]thiazine-6-carboxylate This was prepared (51%) from the ester (a) (23.8 g) by the method of Example (1g) to give a solid (11.8 g).

MS (+ve ion electrospray) m/z 257 (MH$^+$)

(c) 7-Chloro-3-oxo-3,4-dihydro-2H-pyrido[3,2-b][1,4]thiazine-6-carboxylic acid This compound was prepared (96%) from the ester (b) (11.84 g) by the method of Example (1 h) to give a solid (9.6 g).

MS (APCI$^-$) m/z 243 ([M−H]$^-$)

(d) 7-Chloro-6-hydroxymethyl-3-oxo-3,4-dihydro-2H-pyrido[3,2-b][1,4]thiazine This compound was prepared (70%) from the carboxylic acid (c) by the method of Example (1i).

MS (+ve ion electrospray) m/z 231 (MH$^+$)

(e) 7-Chloro-3-oxo-3,4-dihydro-2H-pyrido[3,2-b][1,4]thiazine-6-carboxaldehyde This compound was prepared (49%) from the alcohol (d) by the method of Example (1j) to give a solid (2.01 g).

MS (+ve ion electrospray) m/z 229 (MH+)

(f) Title Compound

This was prepared from amine dihydrochloride (5e) (100 mg) and aldehyde (e) (58 mg) by the method of Example (5f) affording, after workup and chromatography the free base of the title compound as a white solid (55 mg).

$^1$H NMR δ (CD$_3$OD) 8.65 (1H, d), 8.05 (1H, d), 7.70 (1H, s), 7.50 (1H, d), 7.28 (1H, t), 6.95 (1H, d), 4.18 (3H, s), 4.00 (2H, s), 3.50 (2H, s), 2.62 (1H, m), 2.10 (2H, m), 2.00-1.80 (4H, m), 1.65 (2H, m).

MS (+ve ion electrospray) m/z 528 (MH+).

This material was converted into the dihydrochloride by the method of Example (1) affording a white solid (57 mg).

Example 25

1-Hydroxy-t-4-[(3-oxo-3,4-dihydro-2H-pyrido[3,2-b][1,4]thiazin-6-ylmethyl)-amino]-r-cyclohexanecarboxylic acid (3-methyl-quinoxalin-5-yl)-amide dihydrochloride (cis-1-hydroxy-N-(3-methyl-5-quinoxalinyl)-4-{[(3-oxo-3,4-dihydro-2H-pyrido[3,2-b][1,4thiazin-6-yl)methyl]amino}cyclohexanecarboxamide hydrochloride)

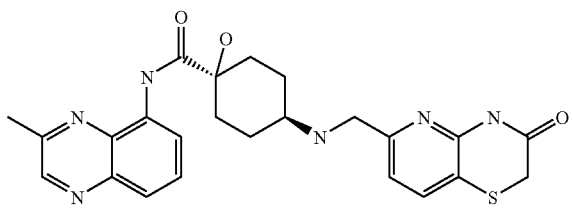

(a) 1,1,1-Trifluoro-methanesulfonic acid 3-methyl-quinoxalin-5-yl ester

A solution of 3-methyl-quinoxalin-5-ol (prepared as described by Y. Abe et al, J. Med. Chem., 1998, 41 (21), 4062) (630 mg, 3.9 mmol) in dichloromethane (5 ml) was treated with triethylamine (0.6 ml) then N-phenyltrifluoromethanesulfonimide (2.12 g) was added. The mixture was stirred overnight, washed with saturated aqueous sodium carbonate, dried and evaporated. The residue was chromatographed eluting with 40% ethyl acetate in petrol affording a pale yellow solid (1.04 g, 90%).

MS (+ve ion electrospray) m/z 293 (MH+).

(b) [4-r-Hydroxy-4-(3-methyl-quinoxalin-5-ylcarbamoyl)-c-cyclohexyl]-carbamic acid tert-butyl ester This was prepared from amide (1f) (450 mg) and triflate (a) (500 mg) by the method of Example (1l). Chromatography on silica eluting with 2-5% methanol in dichloromethane afforded a white solid (320 mg, 47%).

MS (+ve ion electrospray) m/z 401 (MH$^+$).

(c) t-4-Amino-1-hydroxy-r-cyclohexanecarboxylic acid (3-methyl-quinoxalin-5-yl)-amide This was prepared from carbamate (b) (320 mg) by the procedure of Example (9j) affording a white solid (210 mg, 88%).

MS (+ve ion electrospray) m/z 301 (MH$^+$).

(d) Title Compound

This was prepared from amine (c) (100 mg) and aldehyde (1j) (64 mg) by the method of Example (1n) affording, after workup and chromatography the free base of the title compound as a white solid (64 mg, 41%).

$^1$H NMR δ (CDCl$_3$) 8.80-8.75 (2H, m), 7.80-7.70 (2H, m), 7.65 (1H, d), 6.95 (1H, d), 3.88 (2H, s), 3.50 (2H, s), 2.79 (3H, s), 2.65 (1H, m), 2.10 (2H, m), 2.00-1.80 (4H, m), 1.65 (2H, m).

MS (+ve ion electrospray) m/z 479 (MH+).

This material was converted into the dihydrochloride by the method of Example (1) affording a white solid (75 mg).

Example 26

1-Hydroxy-t-4-[(3-oxo-3,4-dihydro-2H-pyrido[3,2-b][1,4]thiazin-6-ylmethyl)-amino]-r-cyclohexanecarboxylic acid (2-methyl-1-oxo-1,2-dihydro-isoquinolin-8-yl)-amide hydrochloride (cis-1-hydroxy-N-(2-methyl-1-oxo-1,2-dihydro-8-isoquinolinyl)-4-{[(3-oxo-3,4-dihydro-2H-pyrido[3,2-b][1,4]thiazin-6-yl)methyl]amino}cyclohexanecarboxamide hydrochloride)

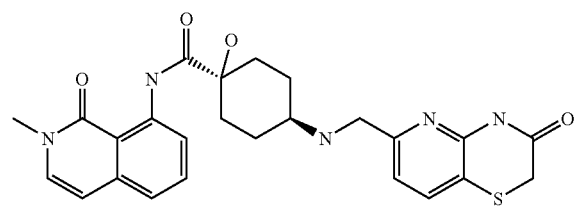

(a) 8-Bromo-isoquinoline-N-oxide

A solution of 8-bromo-isoquinoline (prepared by the method of F. T. Tyson, J.A.C.S., 1939, 61, 183) (1.25 g, 6 mmol) in acetic acid (5 ml) was treated with 27% aqueous hydrogen peroxide solution (1.8 ml) and heated at 75° C. overnight. The mixture was evaporated and the residue partitioned between aqueous sodium carbonate solution and dichloromethane, re-extracting with dichloromethane twice more. The combined organic extracts were dried and evaporated. The residue was triturated with ether/petrol and isolated by filtration (1.14 g, 85%).

MS (+ve ion electrospray) m/z 225 (MH+)

(b) 8-Bromo-2H-isoquinolin-1-one

A suspension of (a) (630 mg, 2.8 mmol) in DMF (10 ml) was treated with trifluoroacetic acid anhydride (4 ml). The clear solution was stirred at room temperature overnight then evaporated. The residue was treated with dilute aqueous sodium carbonate solution and extracted several times with 5% methanol/dichloromethane. The combined organic extracts were washed with brine, dried and evaporated. The crude product was chromatographed on silica eluting with 0-10% methanol in dichloromethane affording a white solid (180 mg, 29%).

MS (+ve ion electrospray) m/z 225 (MH+)

(c) 8-Bromo-2-methyl-2H-isoquinolin-1-one

A solution of (b) (180 mg, 0.8 mmol) in DMF (5 ml) was treated with potassium carbonate (140 mg) and methyl iodide (0.062 ml) and stirred for 3 days then evaporated. The residue was partitioned between dilute aqueous sodium chloride solution and dichloromethane, re-extracting with dichloromethane twice more. The combined organic extracts were dried and evaporated affording a yellow solid (180 mg, 94%).

MS (+ve ion electrospray) m/z 239 (MH+)

(d) [4-r-Hydroxy-4-(2-methyl-1-oxo-1,2-dihydro-isoquinolin-8-ylcarbamoyl)-c-cyclohexyl]-carbamic acid tert-butyl ester This was prepared from amide (1f) (200 mg) and bromide (c) (180 mg) according to the procedure for Example (1l) affording a brown gum (290 mg, 92%).
MS (+ve ion electrospray) m/z 416 (MH+).

(e) t-4-Amino-1-hydroxy-r-cyclohexanecarboxylic acid (2-methyl-1-oxo-1,2-dihydro-isoquinolin-8-yl)-amide This was prepared from carbamate (d) (280 mg) by the procedure of Example (1m) affording a brown gum (210 mg, 100%).

MS (+ve ion electrospray) m/z 316 (MH+).

(f) Title Compound
Amine (e) (110 mg) and aldehyde (1j) (68 mg) were reacted together with sodium cyanoborohydride (30 mg) according to the procedure of Example (1n) affording, after workup and chromatography, the free base of the title compound as a white solid (85 mg, 49%).
$^1$H NMR δ(CDCl$_3$) 13.65 (1H, bs), 8.80 (1H, d), 7.65-7.55 (2H, m), 7.20 (1H, d), 7.05-6.95 (2H, m), 6.48 (1H, d), 3.90 (2H, s), 3.55 (3H, s), 3.45 (2H, s), 2.70 (1H, m), 2.20-1.60 (8H, m)

MS (+ve ion electrospray) m/z 494 (MH+).

This material was converted into the hydrochloride salt by the method of Example (1) affording the title compound as a white solid (82 mg).

Example 27

1-Hydroxy-t-4-[(3-oxo-3,4-dihydro-2H-pyrido[3,2-b][1,4]thiazin-6-ylmethyl)-amino]-r-cyclohexanecarboxylic acid (1-methoxy-isoquinolin-8-yl)-amide hydrochloride (cis- 1-hydroxy-N-[1-(methyloxy)-8-isoquinolinyl]-4-{[(3-oxo-3,4-dihydro-2H-pyrido[3,2-b][1,4]thiazin-6-yl)methyl]amino}cyclohexanecarboxamide hydrochloride)

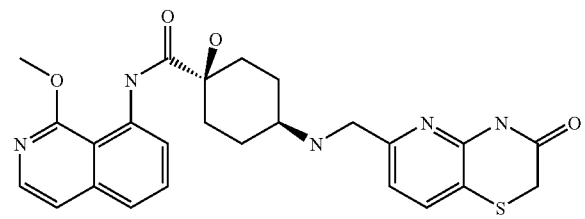

(a) 8-Bromo-1-methoxy-isoquinoline

A solution of N-oxide (26a) (500 mg, 2.2 mmol) in methanol (15 ml) was treated at 0° C. with methyl chloroformate (0.22 ml, 2.9 mmol) and triethylamine (0.64 ml, 4.5 mmol). The mixture was stirred overnight then evaporated. The residue was partitioned between dilute aqueous sodium chloride solution and dichloromethane, re-extracting with dichloromethane. The combined organic extracts were dried and evaporated affording an oil which was chromatographed on silica eluting with dichloromethane affording an oil (280 mg, 53%).

MS (+ve ion electrospray) m/z 239 (MH+)

(b) [r-4-Hydroxy-4-(1-methoxy-isoquinolin-8-ylcarbamoyl)-c-cyclohexyl]-carbamic acid tert-butyl ester This was prepared from amide (1f) (300 mg) and bromide (a) (270 mg) according to the procedure for Example (1l) affording an off-white solid (160 mg, 34%).

MS (+ve ion electrospray) m/z 416 (MH+).

(c) t-4-Amino-1-hydroxy-r-cyclohexanecarboxylic acid (1-methoxy-isoquinolin-8-yl)-amide This was prepared from carbamate (c) (160 mg) by the procedure of Example (1m) affording a brown gum (130 mg, 100%).

MS (+ve ion electrospray) m/z 316 (MH+).

(d) Title Compound
Amine (c) (130 mg) and aldehyde (1j) (86 mg) were reacted together with sodium cyanoborohydride (30 mg) according to the procedure of Example (1n) affording, after workup and chromatography, the free base of the title compound as a white solid (58 mg, 29%).
$^1$H NMR δ(CDCl$_3$) 11.90 (1H, bs), 8.82 (1H, d), 7.95 (1H, d), 7.20 (1H, d), 7.60-7.50 (2H, m), 7.45 (1H, d), 7.20 (1H, d), 6.95 (1H, d), 4.20 (3H, s), 3.95 (2H, s), 3.50 (2H, s), 2.70 (1H, m), 2.20-1.60 (8H, m)

MS (+ve ion electrospray) m/z 494 (MH+).

This material was converted into the hydrochloride salt by the method of Example (1) affording the title compound as a white solid (64 mg).

Example 28

1-Hydroxy-t-4-[(3-oxo-3,4-dihydro-2H-pyrido[3,2-b][1,4]thiazin-6-ylmethyl)-amino]-r-cyclohexanecarboxylic acid (5-methoxy-quinolin-4-yl)-amide dihydrochloride (cis-1-hydroxy-N-[5-(methyloxy)-4-quinolinyl]-4-{[(3-oxo-3,4-dihydro-2H-pyrido[3,2-b][1,4thiazin-6-yl)methyl]amino}cyclohexanecarboxamide hydrochloride)

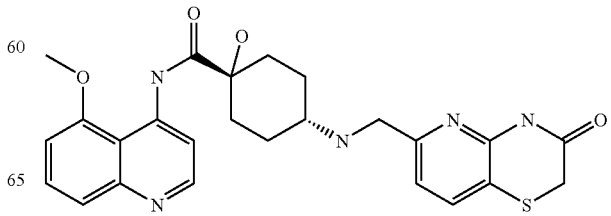

(a) 5-[(2-Bromo-5-methoxy-phenylamino)-methylene]-2,2-dimethyl-[1,3]dioxane-4,6-dione A solution of 2-bromo-5-methoxy-phenylamine (16.1 g, 80 mmol), 2,2-dimethyl-[1,3]dioxane-4,6-dione (Meldrum's acid) (13.7 g, 95 mmol) and triethyl orthoformate (14.1 g, 95 mmol) in ethanol (82 ml) was heated to reflux for 2 hours then allowed to cool to room temperature. Filtration and drying in vacuo afforded a white solid (25.7 g, 91%)

MS (APCI⁻) m/z 354 (M−H)

(b) 8-Bromo-5-methoxy-1H-quinolin-4-one

Dowtherm A (30 ml) was heated to reflux and enamine (a) (10 g) was added portionwise (CAUTION—vigorous evolution of $CO_2$ and acetone) over 2 minutes. Heating was continued for a further 2 minutes then the mixture was allowed to cool to room temperature. Filtration and drying in vacuo afforded a brown solid (5.4 g, 76%).

MS (APCI⁻) m/z 253 (M−H)

(c) 5-Methoxy-1H-quinolin-4-one

Quinolone (b) (5.4 g, 21 mmol) was dissolved in a mixture of dioxin (300 ml) and 2M aqueous sodium hydroxide solution (21 ml, 42 mmol) then hydrogenated over 10% palladium on charcoal (2.3 g) for 18 hours. The mixture was filtered, neutralised (5M hydrochloric acid) and concentrated when crystallisation commenced. Filtration, washing with water and drying in vacuo afforded a solid (2.5 g, 70%).

MS (APCI⁻) m/z 174 (M−H)

(d) 4-Bromo-5-methoxy-quinoline

A solution of quinolone (c) (3.2 g, 18 mmol) in DMF (22 ml) was treated with phosphorous tribromide (2.2 ml). After 2 hours the mixture was added to water and neutralised with saturated aqueous sodium bicarbonate solution. Filtration and drying afforded a yellow solid (3.6 g, 85%).

MS (+ve ion electrospray) m/z 239 (MH+)

(e) [r-4-Hydroxy-4-(5-methoxy-quinolin-4-ylcarbamoyl)-cyclohexyl]-c-carbamic acid tert-butyl ester This was prepared from amide (1f) (516 mg) and bromide (d) (478 mg) according to the procedure for Example (1l) affording an off-white solid (150 mg, 18%).

MS (+ve ion electrospray) m/z 416 (MH+)

(f) t-4-Amino-1-hydroxy-r-cyclohexanecarboxylic acid (5-methoxy-quinolin-4-yl)-amide This was prepared from carbamate (e) (470 mg) by the procedure of Example (9j) affording a white solid (302 mg, 85%).

MS (+ve ion electrospray) m/z 316 (MH⁺)

(g) Title Compound

Amine (f) (302 mg) and aldehyde (1j) (186 mg) were reacted together with sodium cyanoborohydride (122 mg) according to the procedure of Example (1n) affording, after workup and chromatography, the free base of the title compound as a white solid (41 mg, 9%).

¹H NMR δ($CD_3OD$) 8.80 (2H, m), 8.80-8.60 (3H, m), 7.15 (1H, d), 7.05 (1H, d), 4.15 (3H, s), 4.05 (2H, s), 3.50 (2H, s), 2.80 (1H, m), 2.10-1.60 (8H, m)

MS (+ve ion electrospray) m/z 494 (MH+)

This material was converted into the dihydrochloride salt by the method of Example (1) affording the title compound as a white solid (26 mg).

Example 29

1-Hydroxy-t-4-[(3-oxo-3,4-dihydro-2H-pyrido[3,2-b][1,4]oxazin-6-ylmethyl)-amino]-r-cyclohexanecarboxylic acid [1,6]naphthyridin-4-ylamide (cis-1-hydroxy-N-1,6-naphthyridin-4-yl-4-{[(3-oxo-3,4-dihydro-2H-pyrido[3,2-b][1,4]oxazin-6-yl)methyl]amino}cyclohexanecarboxamide)

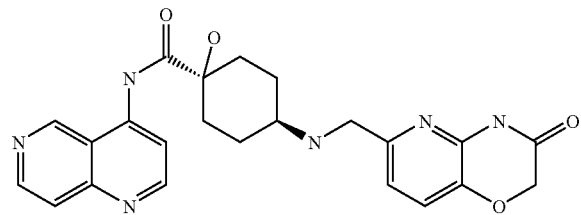

(a) 2,2-Dimethyl-5-(pyridin-4-ylaminomethylene)-[1,3]dioxane-4,6-dione

A mixture of 2,2-dimethyl-[1,3]dioxane-4,6-dione (Meldrum's acid) (8.4 g, 59 mmol) and trimethyl orthoformate (50 mL) was heated to reflux for 2 hours. 4-Aminopyridine (5 g, 53 mmol) was added and the mixture heated for a further 0.25 hour. The resulting solid was washed with a small amount of cold ethanol and dried in vacuo (7.3 g, 55%).

MS (APCI⁻) m/z 247 ([M−H]⁻)

(b) 1-H-[1,6]Naphthyridin-4-one

Dowtherm A (60 mL) was brought to reflux and (a) (6.3 g, 25.4 mmol) was added portionwise over 2 minutes. The mixture was heated for a further 5 minutes then allowed to cool to room temperature. The resulting solid was washed with a small amount of cold ethanol and dried in vacuo (2.6 g, 69%).

MS (APCI⁻) m/z 145 ([M−H]⁻)

(c) 4-Bromo-[1,6]naphthyridine

Phophorous tribromide (0.38 ml, 4 mmol) was added to DMF (10 mL) with vigorous stirring. Naphthyridone (b) (584 mg, 4 mmol) was added. After 0.5 hours the mixture was added to ice/water, neutralised with aqueous sodium bicarbonate solution and extracted with ethyl acetate. Drying and evaporation afforded a solid (240 mg, 29%).

MS (+ve ion electrospray) m/z 210 (MH+).

(d) [r-4-Hydroxy-4-([1,6]naphthyridin-4-ylcarbamoyl)-c-cyclohexyl]-carbamic acid tert-butyl ester This was prepared from amide (1f) (142 mg) and bromide (c) (105 mg) according to the procedure for Example (1l) affording an off-white solid (142 mg, 74%).

MS (+ve ion electrospray) m/z 387 (MH+)

(e) t-4-Amino-1-hydroxy-r-cyclohexanecarboxylic acid [1,6]naphthyridin-4-ylamide trifluoroacetate This was prepared from carbamate (d) (112 mg) according to the procedure for Example (9j) affording a white solid.

MS (+ve ion electrospray) m/z 287 (MH+).

(f) Title Compound

Amine trifluoroacetate (e) (prepared above, ca 0.4 mmol) was reductively alkylated with aldehyde (7j) (71 mg) according to the procedure for Example (7k) affording the title compound as a white solid (70 mg).

MS (+ve ion electrospray) m/z 449 (MH$^+$).
$^1$H NMR δ (d6-DMSO) 9.60 (1H, s), 9.05 (1H, d), 8.80 (1H, d), 8.18 (1H, d), 7.90 (1H, d), 7.40 (1H, d), 7.10 (1H, d), 4.70 (2H, s), 3.85 (2H, s), 2.75 (1H, m), 2.20-1.90 (6H, m), 1.80 (2H, m)

Example 30

1-Hydroxy-t-4-[(3-oxo-3,4-dihydro-2H-pyrido[3,2-b][1,4]thiazin-6-ylmethyl)-amino]-r-cyclohexanecarboxylic acid (2-methyl-quinoxalin-5-yl)-amide dihydrochloride (cis-1-hydroxy-N-(2-methyl-5-quinoxalinyl)-4-{[(3-oxo-3,4-dihydro-2H-pyrido[3,2-b][1,4]thiazin-6-yl)methyl]amino}cyclohexanecarboxamide hydrochloride)

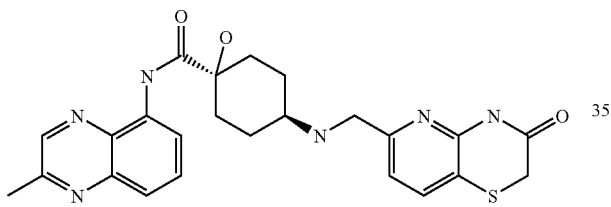

(a) 1,1,1-Trifluoro-methanesulfonic acid 2-methyl-quinoxalin-5-yl ester

This was prepared from 2-methyl-quinoxalin-5-ol (prepared as described by Y. Abe et al, J. Med. Chem., 1998, 41 (21), 4062) according to the procedure for Example (25a).

MS (+ve ion electrospray) m/z 293 (MH+).

(b) [r-4-Hydroxy-4-(2-methyl-quinoxalin-5-ylcarbamoyl)-c-cyclohexyl]-carbamic acid tert-butyl ester This was prepared from triflate (a) and amide (1f) according to the procedure for Example (11).

MS (+ve ion electrospray) m/z 401 (MH$^+$).

(c) t-4-Amino-1-hydroxy-r-cyclohexanecarboxylic acid (2-methyl-quinoxalin-5-yl)-amide This was prepared from carbamate (b) according to the procedure for Example (9j).

MS (+ve ion electrospray) m/z 301 (MH$^+$).

(d) Title Compound

This was prepared from amine (c) (100 mg) and aldehyde (1j) (64 mg) by the method of Example (1n) affording, after workup and chromatography the free base of the title compound as a white solid (93 mg, 59%).

$^1$H NMR δ (CDCl$_3$) 8.72 (1H, m), 8.60 (1H, s), 7.75-7.70 (2H, m), 7.55 (1H, d), 6.95 (1H, d), 3.90 (2H, s), 3.50 (2H, s), 2.75 (3H, m), 2.68 (1H, m), 2.10 (2H, m), 2.00-1.80 (4H, m), 1.65 (2H, m).

MS (+ve ion electrospray) m/z 479 (MH+).

This material was converted into the dihydrochloride by the method of Example (1) affording a white solid (75 mg).

Example 31

(1R,3S,4R)-3-Fluoro-4-[(3-oxo-3,4-dihydro-2H-pyrido[3,2-b][1,4]oxazin-6-ylmethyl)-amino]-cyclohexanecarboxylic acid (6-methoxy-[1,5]naphthyridin-4-yl)-amide dihydrochloride ((1R,3S,4R)-3-fluoro-N-[6-(methyloxy)-1,5-naphthyridin-4-yl]-4-{[(3-oxo-3,4-dihydro-2H-pyrido[3,2-b][1,4]oxazin-6-yl)methyl]amino}cyclohexanecarboxamide hydrochloride)

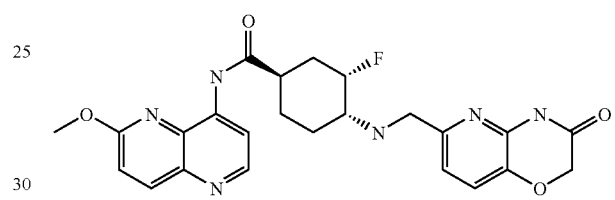

(a) (R)-Ethyl-4-trimethylsilyloxycyclohex-3-enecarboxylate

To (S,S)-bis α-methyl benzylamine (9 g, 40 mmol) in THF (200 mL) under argon was added dibutyl magnesium in heptane (20 mL, 1M) and the mixture heated to reflux. After 1.5 hours, the mixture was cooled to −78° C. and trimethylsilyl chloride (10.1 mL) and N,N-dimethylpropyleneurea (1.2 mL) added dropwise. After a further 20 minutes ethyl-4-oxocyclohexane carboxylate (2.87 mL, 18 mmol) was added dropwise. The reaction was stirred at −78° C. for 16 hours, then saturated sodium hydrogen carbonate (100 mL), water (100 mL) and hexane (200 mL) were added. The organic soluble material was purified by chromatography on silica gel eluting with 0-5% diethyl ether in hexane to give an oil (3.5 g, 80%).

$^1$H NMR δ(CDCl$_3$) 4.88 (1H, m), 4.20 (2H, q), 2.50 (1H, m), 2.35 (2H, m), 2.10 (2H, m), 2.05 (1H, m), 1.85 (1H, m), 1.30 (3H, t), 0.20 (9H, s)

(b) (1R,3S)-3-Fluoro-4-oxo-cyclohexanecarboxylic acid ethyl ester

Silyl enol ether (a) (3.5 g) in acetonitrile (40 mL) at 0° C. was treated portionwise with 1-chloromethyl-4-fluoro-1,4-diazoniabicyclo[2.2.2]octanebis(tetrafluoroborate), (Selectfluor™), (6.16 g). After 75 min, saturated sodium hydrogen carbonate (50 mL) and water (50 mL) were added and the mixture extracted with ethyl acetate. The organic soluble material was purified by careful chromatography on silica gel eluting with 5-60% diethyl ether in hexane to give an oil (1.02 g).

$^1$H NMR δ(CDCl$_3$) 5.06 (1H, m), 4.20 (2H, q), 3.05 (1H, m), 2.60-2.40 (2H, m), 2.30-2.20 (2H, m), 2.10 (2H, m), 1.30 (3H, t)

(c) (1R,3S,4R)-3-Fluoro-4-((R)-1-phenyl-ethylamino)-cyclohexanecarboxylic acid ethyl ester Ketone (b) (1.02 g, 5.4 mmol) in dichloroethane (24 mL) and acetic acid (1 mL) was treated with (R)-α-methyl benzylamine (0.88 mL) and sodium triacetoxyborohydride (2.2 g). After 4.5 hours, the reaction mixture was loaded onto a silica gel column packed in 0.5% (2M ammonia in methanol) in dichloromethane and eluted with 0.5-10% (2M ammonia in methanol) in dichloromethane to give an oil (1.2 g).

$^1$H NMR δ(d-6 MeOH) 7.50 (5H, m), 4.95 (1H, m), 4.62 (1H, q), 4.15 (2H, q), 3.20 (1H, m), 2.90 (1H, m), 2.50 (1H, m), 2.10 (1H, m), 1.95 (1H, m), 1.75 (1H, m), 1.70 (3H, d), 1.55 (2H, m), 1.25 (3H, t)

(d) (1R,3S,4R)-3-Fluoro-4-((R)-1-phenyl-ethylamino)-cyclohexanecarboxylic acid acetate A solution of ester (c) (1.5 g) in methanol (50 mL) was treated with lithium hydroxide (630 mg). After 2 hours acetic acid (1 mL) was added and the mixture was evaporated to dryness. Chromatography on silica eluting with 1:9:90 (acetic acid:methanol:dichloromethane) afforded an oil (1.02 g).

$^1$H NMR δ(d-6 MeOH) 7.50 (5H, m), 5.25 (1H, m), 4.62 (1H, q), 3.20 (1H, m), 2.60 (1H, m), 2.40 (1H, m), 2.30 (3H, s), 2.10 (1H, m), 1.95 (1H, m), 1.75 (1H, m), 1.70 (3H, d), 1.60-1.40 (2H, m)

(e) (1R,3S,4R)-3-Fluoro-4-((R)-1-phenyl-ethylamino)-cyclohexanecarboxylic acid amide A solution of (d) (75 mg) in DMF (2 mL) was treated with ammonium bicarbonate (80 mg), 1-hydroxy-7-azabenzotriazole (57 mg), and 1-ethyl-3-(3-dimethylaminopropyl)carbodiimide hydrochloride (60 mg). After 2.5 hours the reaction mixture was evaporated and the residue partitioned between ethyl acetate/dilute brine. The organic extract was dried and evaporated. The residue was chromatographed eluting with 2-8% methanol/dichloromethane affording a white solid (52 mg).

$^1$H NMR δ(CDCl$_3$) 7.30 (3H, m), 7.20 (2H, m), 5.40 (1H, bs), 5.30 (1H, bs), 5.02 (1H, m), 4.00 (1H, q), 2.40-2.20 (4H, m), 1.90 (1H, m), 1.78 (1H, m), 1.55-1.45 (2H, m), 1.30 (3H, d)

(f) (1R,3S,4R)-4-Amino-3-fluoro-cyclohexanecarboxylic acid amide

A solution of of (e) (280 mg) in ethanol (15 ml) and 20% palladium(II) hydroxide on charcoal (80 mg) was hydrogenated at 50 p.s.i. for 16 hours. Filtration and evaporation afforded a white solid (230 mg).

$^1$H NMR δ 4.75 (1H, m), 2.70 (1H, m), 2.55 (1H, m), 2.15 (1H, m), 1.90-1.55 (5H, m)

(g) ((1R,2S,4R)-4-Carbamoyl-2-fluoro-cyclohexyl)-carbamic acid tert-butyl ester A solution of (f) (230 mg) in dichloromethane (10 mL) was treated with di-tert-butyl dicarbonate (324 mg). After 4 hours the mixture was concentrated and treated with ether and hexane. The resultant precipitate was isolated by filtration and dried in vacuo affording a solid (250 mg).

$^1$H NMR δ 4.78 (1H, m), 3.50 (1H, m), 2.45 (1H, m), 2.15 (1H, m), 1.95-1.60 (5H, m), 1.45 (9H, s)

(h) [(1R,2S,4R)-2-Fluoro-4-(6-methoxy-[1,5]naphthyridin-4-ylcarbamoyl)-cyclohexyl]-carbamic acid tert-butyl ester This was prepared from amide (g) (250 mg) and 1,1,1-Trifluoro-methanesulfonic acid 6-methoxy-[1,5]naphthyridin-4-yl ester (WO02096907 Example 1(b)) (478 mg) according to the procedure for Example (1l) affording an off-white solid (390 mg).

MS (+ve ion electrospray) m/z 419 (MH+)

(i) (1R,3S,4R)-4-Amino-3-fluoro-cyclohexanecarboxylic acid (6-methoxy-[1,5]naphthyridin-4-yl)-amide This was prepared from carbamate (e) (390 mg) by the procedure of Example (9j) affording a white solid (269 mg).

MS (+ve ion electrospray) m/z 319 (MH$^+$)

(j) Title Compound

Amine (i) (100 mg) and aldehyde (7j) (66 mg) were reacted together with sodium cyanoborohydride according to the procedure of Example (1n) affording, after workup and chromatography, the free base of the title compound as a white solid (107 mg).

$^1$H NMR δ (d6-DMSO) 9.85 (1H, bs), 8.67 (1H, d), 8.40 (1H, d), 8.26 (1H, d), 7.05 (1H, d), 5.05 (1H, d), 4.60 (2H, s), 4.15 (3H, s), 4.75 (2H, s), 3.05 (1H, m), 2.70 (1H, m), 2.25 (1H, m), 1.90 (3H, m), 1.55 (2H, m)

MS (+ve ion electrospray) m/z 481 (MH+)

This material was converted into the dihydrochloride salt by the method of Example (1) affording the title compound as a white solid (110 mg).

Example 32

(1R,3S,4R)-3-Fluoro-4[(7-fluoro-3-oxo-3,4-dihydro-2H-pyrido[3,2-b][1,4]thiazin-6-ylmethyl)-amino]-cyclohexanecarboxylic acid (6-methoxy-[1,5]naphthyridin-4-yl)-amide dihydrochloride((1R,3S,4R)-3-fluoro-4-{[(7-fluoro-3-oxo-3,4-dihydro-2H-pyrido[3,2-b][1,4]thiazin-6-yl)methyl]amino}-N-[6-(methyloxy)-1,5-naphthyridin-4-yl] cyclohexanecarboxamide hydrochloride)

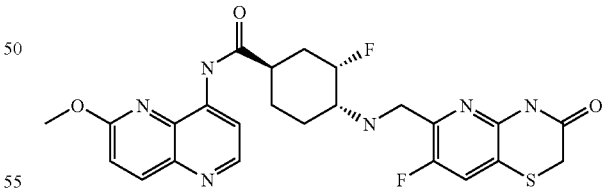

Amine (31i) (100 mg) and aldehyde (23f) (66 mg) were reacted together with sodium cyanoborohydride according to the procedure of Example (1n) affording, after workup and chromatography, the free base of the title compound as a white solid (102 mg).

$^1$H NMR δ (d6-DMSO) 8.70 (1H, d), 8.42 (1H, d), 8.28 (1H, d), 7.85 (1H, d), 7.32 (1H, d), 5.05 (1H, d), 4.15 (3H, s), 3.85 (2H, s), 3.58 (2H, s), 3.05 (1H, m), 2.70 (1H, m), 2.25 (1H, m), 1.90 (3H, m), 1.55 (2H, m)

MS (+ve ion electrospray) m/z 515 (MH+)

This material was converted into the dihydrochloride salt by the method of Example (1) affording the title compound as a white solid (117 mg).

Example 33

1-Hydroxy-t-4-[(3-oxo-3,4-dihydro-2H-pyrido[3,2-b][1,4]oxazin-6-ylmethyl)-amino]-c-cyclohexanecarboxylic acid (3-methyl-1,2,3,4-tetrahydro-quinoxalin-5-yl)-amide dihydrochloride (cis-1-hydroxy-N-(3-methyl-1,2,3,4-tetrahydro-5-quinoxalinyl)-4-{[(3-oxo-3,4-dihydro-2H-pyrido[3,2-b][1,4]oxazin-6-yl)methyl]amino}cyclohexanecarboxamide hydrochloride)

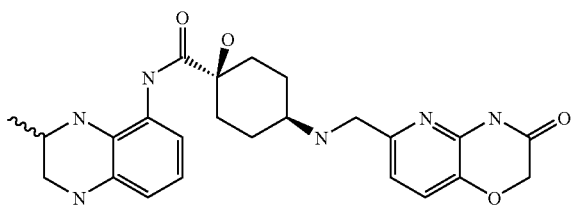

The free base of the title compound was prepared in 11% yield from amine (25c) and aldehyde (7j) according to the general reductive alkylation procedure of Example (In), affording an oil after chromatography (17 mg).

$^1$H NMR δ (CDCl$_3$) 8.80 (1H, bs), 7.18 (1H, d), 6.85 (1H, d), 6.73 (1H, d), 6.58 (1H, t), 6.38 (1H, d), 4.60 (2H, s), 3.85 (2H, s), 3.40 (1H, m), 3.25 (1H, m), 2.85 (1H, m), 2.60 (1H, m), 2.10-1.50 (7H, m), 1.18 (3H, d)

MS (+ve ion electrospray) m/z 467 (MH+)

This material was converted into the dihydrochloride salt by dissolving in CDCl$_3$ (1 ml) and treating with 0.4M HCl in dioxan (0.2 ml) then evaporating to give a white solid (22 mg).

Example 34

1-Hydroxy-t-4-[(3-oxo-3,4-dihydro-2Hpyrido[3,2-b][1,4]thiazin-6-ylmethyl)-amino]-r-cyclohexanecarboxylic acid (3-methoxy-quinoxalin-5-yl)-amide hydrochloride (cis-1-hydroxy-N-[3-(methyloxy)-5-quinoxalinyl]-4-{[(3-oxo-3,4-dihydro-2H-pyrido[3,2-b][1,4]thiazin-6-yl)methyl]amino}cyclohexanecarboxamide hydrochloride)

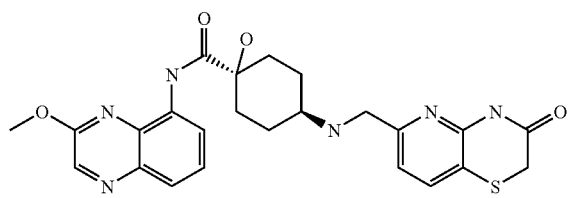

(a) 2-Nitro-6-triisopropylsilanyloxy-phenylamine

A solution of 2-amino-3-nitro-phenol (42.9 g, 278 mmol) and imidazole (28.4 g, 417 mmol) in tetrahydrofuran (750 ml) was treated with chloro-triisopropyl-silane (62.3 g, 323 mmol). After 18 hours the mixture was filtered, diluted with ethyl acetate, washed with water, dried and evaporated to give an oil (91 g).

MS (+ve ion electrospray) m/z 311 (MH$^+$).

(b) 3-Triisopropylsilanyloxy-benzene-1,2-diamine

A solution of (a) (91 g) in ethanol (500 ml) was hydrogenated over 10% palladium on charcoal (8.5 g) for 3 days then filtered and evaporated to give an oil (80.7 g).

MS (+ve ion electrospray) m/z 281 (MH+).

(c) 8-Triisopropylsilanyloxy-1H-quinoxalin-2-one

A solution of (b) (80.7 g) in ethanol (1 liter) was treated with a 50% solution of ethyl glyoxalate in toluene (60 ml, 294 mmol) and heated to reflux for 2 hours. The mixture was left at room temperature overnight and filtered affording 5-triisopropylsilanyloxy-1H-quinoxalin-2-one. The filtrate was evaporated and the residue chromatographed eluting with a 0-3% gradient of methanol in dichloromethane affording 8-triisopropylsilanyloxy-1H-quinoxalin-2-one as a white solid (14.9 g).

MS (+ve ion electrospray) m/z 319 (MH+).

(d) 2-Methoxy-8-triisopropylsilanyloxy-quinoxaline

A solution of (c) (2.0 g, 6.2 mmol) in dichloromethane/methanol/acetonitrile (40 ml/4 ml/40 ml) was treated with triethylamine (1.1 ml, 8 mmol) then a solution of (trimethylsilyl)diazomethane in hexane (2M; 4 ml, 8 mmol). The mixture was stirred overnight then evaporated. The residue was chromatographed on silica eluting with dichloromethane affording an oil (1.0 g, 48%).

MS (+ve ion electrospray) m/z 333 (MH+).

(e) 3-Methoxy-quinoxalin-5-ol

A solution of (d) (6.95 g, 21 mmol) in tetrahydrofuran/methanol (280 ml/140 ml) was treated with caesium fluoride (4.73 g, 31.4 mmol) and stirred for 18 hours. The mixture was evaporated and the residue partitioned between diethyl ether and dilute aqueous hydrochloric acid. The aqueous phase was further extracted with diethyl ether and the combined extracts dried and evaporated to give an oil (4.2 g).

MS (+ve ion electrospray) m/z 177 (MH+).

(f) 1,1,1-Trifluoro-methanesulfonic acid 3-methoxy-quinoxalin-5-yl ester

A solution of (e) (4.23 g, 21 mmol) in dichloromethane (35 ml) was treated with triethylamine (4.5 ml, 32.1 mmol) then N-phenyltrifluoromethanesulfonimide (11.4 g, 32 mmol) was added. The mixture was stirred overnight then washed with saturated aqueous sodium carbonate solution. The aqueous phase was further extracted with dichloromethane and the combined organic extracts were dried and evaporated. The residue was chromatographed on silica eluting with 50% hexane in dichloromethane and then dichloromethane, affording an oil (5.6 g, 87%).

MS (+ve ion electrospray) m/z 309 (MH+).

(g) [r-4-Hydroxy-4-(3-methoxy-quinoxalin-5-ylcarbamoyl)-c-cyclohexyl]-carbamic tert-butyl ester This was prepared from amide (1f) and triflate (f) according to the method of Example (18b) affording a white solid (320 mg).

MS (+ve ion electrospray) m/z 417 (MH$^+$).

(h) t-4-Amino-1-hydroxy-r-cyclohexanecarboxylic acid (2-methyl-quinolin-8-yl)-amide This was prepared in quantitative yield from carbamate (g) by the procedure of Example (1m) affording a white solid (243 mg).

MS (+ve ion electrospray) m/z 317 (MH$^+$).

(i) Title Compound

The free base of the title compound was prepared in 72% yield from amine (1) and aldehyde (1j) according to the general reductive alkylation procedure of Example (1n), affording a white solid after chromatography (135 mg).

$^1$H NMR δ (CDCl$_3$) 8.70 (1H, d), 8.50 (1H, s), 7.73 (1H, d), 7.65 (1H, d), 7.75 (1H, t), 6.95 (1H, d), 4.18 (3H, s), 4.03 (2H, s), 2.90 (1H, m), 2.20-1.70 (8H, m).

MS (+ve ion electrospray) m/z 495 (MH$^+$).

This material was converted into the hydrochloride salt by the method of Example (1) affording the title compound as a white solid (103 mg).

Example 35 t-4-[(2,3-Dihydro-[1,4]dioxino[2,3-c]pyridin-7-ylmethyl)-amino]-1-hydroxy-c-cyclohexanecarboxylic acid (2-methyl-quinolin-8-yl)-amide dihydrochloride (cis-4-[(2,3-dihydro[1,4]dioxino[2,3-c]pyridin-7-ylmethyl)amino]-1-hydroxy-N-(2-methyl-8-quinolinyl)cyclohexanecarboxamide hydrochloride)

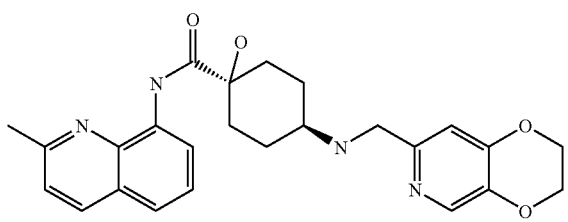

(a) 5-Benzyloxy-2-hydroxymethyl-1H-pyridin-4-one

A mixture of 5-benzyloxy-2-hydroxymethyl-4-pyrone (prepared from Kojic acid by the method of D. Erol, J. Med. Chem., 1994, 29, 893) (9.7 g, 40 mmol), concentrated aqueous (880) ammonia (100 ml), and ethanol (20 ml) was heated to reflux overnight. The mixture was allowed to cool to room temperature then filtered. The resultant solid was washed with ether and dried in vacuo (5.9 g).

MS (APCI+) m/z 232 (MH+).

(b) (2,3-Dihydro-[1,4]dioxino[2,3-c]pyridin-7-yl)-methanol

A solution of (a) (2 g, 8.7 mmol) in water (220 ml) containing sodium hydroxide (17 mmol) was hydrogenated over 10% palladium on charcoal (1 g) for 4 hours. The mixture was filtered and evaporated to give a white solid. This solid was dissolved in N,N-dimethylformamide (8 ml) then treated with potassium carbonate (2.9 g) and 1,2-dibromoethane (0.6 ml, 7 mmol). The mixture was heated at 85° C. overnight. The cooled mixture was evaporated onto silica and chromatographed eluting with 10-30% methanol in ethyl acetate affording a white solid (250 mg, 21%).

MS (APCI+) m/z 168 (MH+).

(c) 2,3-Dihydro-[1,4]dioxino[2,3-c]pyridine-7-carbaldehyde

A solution of (b) (250 mg, 1.5 mmol) in dichloromethane (5 ml) was treated with manganese dioxide (650 mg, 7.5 mmol). After 3 days the mixture was filtered and evaporated affording a white solid (150 mg, 61%).

MS (APCI+) m/z 166 (MH+).

(d) Title Compound

A solution of amine (18c) (0.6 g, 2 mmol) and aldehyde (c) (0.33 g, 2 mmol) in DMF (10 ml) was treated with sodium triacetoxyborohydride (1.28 g, 6 mmol). After 5 hours the mixture was treated with 5M aqueous hydrochloric acid dropwise until no further effervescence was observed and then basified with half-saturated aqueous sodium bicarbonate solution (~100 ml). The resulting precipitate was filtered, washed with water and dried in vacuo. The crude product was chromatographed on silica eluting with 2-10% methanol in dichloromethane affording the free base of the title compound as a white solid (0.58 g, 64%).

$^1$H NMR δ (CDCl$_3$) 8.75 (1H, m), 8.10 (1H, s), 8.00 (1H, d), 7.45 (2H, m), 7.30 (1H, d), 6.82 (1H, s), 4.30 (4H, m), 3.85 (2H, s), 2.75 (3H, s), 2.80 (1H, m), 2.20-1.85 (6H, m), 1.60 (2H, m).

MS (+ve ion electrospray) m/z 449 (MH$^+$).

This material was converted into the dihydrochloride salt by the method of Example (1) affording the title compound as a white solid (0.61 g).

Example 36 t-4-[(2,3-Dihydro-[1,4]dioxino[2,3-c]pyridin-7-ylmethyl)-amino]-cyclohexanecarboxylic acid (2-methyl-quinolin-8-yl)-amide dihydrochloride (trans-4-[(2,3-dihydro[1,4]dioxino[2, 3-c]pyridin-7-ylmethyl)amino]-N-(2-methyl-8-quinolinyl)cyclohexanecarboxamide hydrochloride)

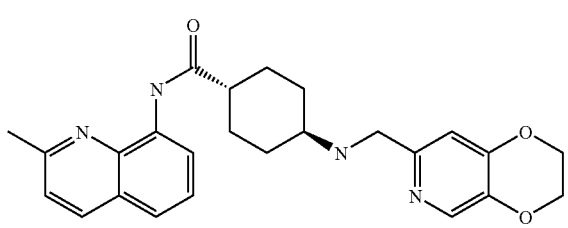

(a) [4-(2-Methyl-quinolin-8-ylcarbamoyl)-cyclohexyl]-carbamic acid tert-butyl ester This was prepared from amide (3a) and triflate (18a) according to the method of Example (18b) affording a white solid.

MS (+ve ion electrospray) m/z 384 (MH+).

(b) 4-Amino-cyclohexanecarboxylic acid (2-methyl-quinolin-8-yl)-amide

This was prepared from carbamate (a) by the procedure of Example (1m) affording a white solid.

MS (+ve ion electrospray) m/z 284 (MH+).

(c) Title Compound

A solution of amine (b) (570 mg, 2 mmol) and aldehyde (35c) (330 mg, 2 mmol) were reacted together according to the general reductive alkylation procedure of Example (35d) affording after chromatography the free base of the title compound as a white solid (690 mg, 79%).

¹H NMR δ (CDCl₃) 8.92 (1H, bs), 8.70 (1H, m), 8.10 (1H, s), 8.00 (1H, d), 7.42 (1H, d), 7.30 (1H, d), 6.88 (1H, s), 4.30 (4H, m), 4.00 (2H, s), 2.76 (3H, s), 2.75 (1H, m), 2.50 (1H, m), 2.20-2.10 (4H, m), 1.80-1.45 (4H, m).

MS (+ve ion electrospray) m/z 433 (MH+).

This material was converted into the dihydrochloride salt by the method of Example (1) affording the title compound as a white solid (0.71 g).

Example 37

(1R,3S,4R)-4-[(2,3-Dihydro-[1,4]dioxino[2,3-c]pyridin-7-ylmethyl)-amino]-3-hydroxy-cyclohexanecarboxylic acid (2-cyano-quinolin-8-yl)-amide hydrochloride ((1R,3S,4R)-N-(2-cyano-8-quinolinyl)-4-[(2,3-dihydro[1,4]dioxino[2,3-c]pyridin-7-ylmethyl)amino]-3-hydroxycyclohexanecarboxamide hydrochloride)

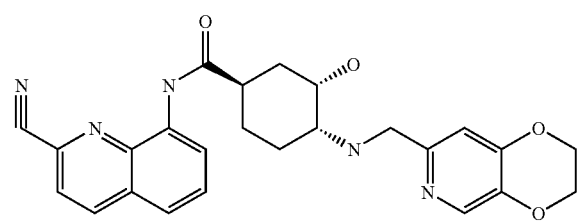

The free base of the title compound was prepared in 40% yield from amine (9j) and aldehyde (35c) according to the general reductive alkylation procedure of Example (1n), affording a white solid after chromatography (350 mg).

¹H NMR δ (d6-DMSO) 9.95 (1H, bs), 8.55 (2H, m), 8.15 (1H, d), 8.05 (1H, s), 7.80 (2H, m), 6.98 (1H, s), 4.55 (1H, bs), 4.30 (4H, m), 4.05 (1H, m), 3.80 (1H, d), 3.70 (1H, d), 3.10 (1H, m), 2.10-1.50 (7H, m).

MS (+ve ion electrospray) m/z 460 (MH+).

This material was converted into the hydrochloride salt by the method of Example (1) affording the title compound as a white solid (380 mg).

Example 38 t-4-[(2,3-Dihydro-[1,4]dioxino[2,3-c]pyridin-7-ylmethyl)-amino]-1-hydroxy-r-cyclohexanecarboxylic acid (2-cyano-quinolin-8-yl)-amide hydrochloride (cis-N-(2-cyano-8-quinolinyl)-4-[(2,3-dihydro[1,4]dioxino[2,3-c]pyridin-7-ylmethyl)amino]-1-hydroxycyclohexanecarboxamide hydrochloride)

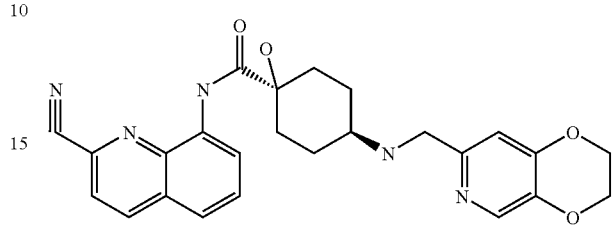

The free base of the title compound was prepared in 47% yield from amine (10b) and aldehyde (35c) according to the general reductive alkylation procedure of Example (1n), affording a yellow solid after chromatography (420 mg).

¹H NMR δ (d6-DMSO) 11.08 (1H, bs), 8.85 (1H, m), 8.75 (1H, d), 8.15 (1H, d), 8.02 (1H, s), 7.80 (2H, m), 6.95 (1H, s) 4.35 (4H, m), 4.05 (1H, m), 3.70 (2H, s), 3.10 (1H, m), 2.10-1.50 (7H, m).

MS (+ve ion electrospray) m/z 460 (MH+).

This material was converted into the hydrochloride salt by the method of Example (1) affording the title compound as a white solid (410 mg).

Example 39

(1R,3R,4R)-4-[(2,3-Dihydro-[1,4]dioxino[2,3-c]pyridin-7-ylmethyl)-amino]-3-methoxy-cyclohexanecarboxylic acid (2-methyl-quinolin-8-yl)-amide dihydrochloride ((1R,3R,4R)-4-[(2,3-dihydro[1,4]dioxino[2,3-c]pyridin-7-ylmethyl)amino]-3-(methyloxy)-N-(2-methyl-8-quinolinyl)cyclohexanecarboxamide hydrochloride

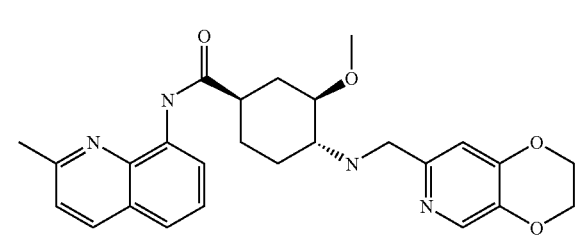

(a) (1R,3R,4S)-4-Bromo-3-hydroxy-cyclohexanecarboxylic acid methyl ester

A solution of bromolactone (9a) (46.6 g, 230 mmol) in methanol (600 ml) was treated with sodium bicarbonate (21 g, 250 mmol) and stirred for 18 hours. The mixture was evaporated and the solid residue extracted with dichloromethane (2×500 ml). The combined extracts were evaporated to afford an oil (52.4 g, 97%).

MS (+ve ion electrospray) m/z 238 (MH+).

(b) (1R,3R,4R)-4-Azido-3-hydroxy-cyclohexanecarboxylic acid methyl ester

A solution of bromide (a) (52.4 g, 221 mmol) in DMF (1.2 liters) was treated with sodium azide (21.5 g, 331 mmol) and heated at 60° C. for 8 hours. The mixture was stirred at room temperature overnight and then evaporated. The residue was extracted with warm iso-propanol (2×300 ml). Evaporation afforded an oil which was chromatographed on silica eluting with a gradient of ethyl acetate in petroleum ether affording an oil (31 g) which was a 2:1 mixture of desired (1R,3R,4R)-4-azido-3-hydroxy-cyclohexanecarboxylic acid methyl ester to (R)-3-oxo-cyclohexanecarboxylic acid methyl ester. Further chromatography on silica eluting with a methanol/dichloromethane gradient afforded the desired intermediate as an oil (18.4 g, 42%)

MS (+ve ion electrospray) m/z 200 (MH$^+$).

(c) (1R,3R,4R)-4-Amino-3-hydroxy-cyclohexanecarboxylic acid methyl ester acetate A solution of azide (b) (18.4 g, 92 mmol) in methanol/acetic acid (360 ml/40 ml) was hydrogenated over 10% palladium on charcoal paste (50% w/w with water, 15 g) for 18 hours. The mixture was filtered through keiselguhr, evaporated, and then triturated with ether to afford a white solid that was isolated by filtration and dried in vacuo (15.6 g, 72%).

MS (+ve ion electrospray) m/z 174 (MH$^+$).

(d) (1R,3R,4R)-4-tert-Butoxycarbonylamino-3-hydroxy-cyclohexanecarboxylic acid methyl ester The acetate salt (c) (15.6 g, 66 mmol) was suspended in tetrahydrofuran (200 ml) and treated with di-tert-butyl carbonate (16 g, 73 mmol) and diisopropylethylamine (14 ml, 10.4 g, 80 mmol). The mixture was heated at 50° C. for 18 hours then evaporated to dryness. The residue was partitioned between water and ethyl acetate. The aqueous phase was further extracted with ethyl acetate and the combined extracts washed with brine, dried and evaporated to give a solid (18.5 g, 100%).

MS (+ve ion electrospray) m/z 274 (MH$^+$).

(e) (1R,3R,4R)-4-tert-Butoxycarbonylamino-3-methoxy-cyclohexanecarboxylic acid methyl ester A mixture of alcohol (d) (6.5 g, 24 mmol), silver(I) oxide (16.5 g, 72 mmol), methyl iodide (4.5 ml) and 3 A molecular sieves (10 g) in dichloromethane (100 ml) was stirred at room temperature for 18 hours. The mixture was filtered and evaporated. The residue was chromatographed on silica eluting with 1:2 ethyl acetate:petrol affording an oil (5.47 g, 80%).

MS (+ve ion electrospray) m/z 288 (MH$^+$).

(f) (1R,3R,4R)-4-tert-Butoxycarbonylamino-3-methoxy-cyclohexanecarboxylic acid The ester (e) (5.47 g, 19 mmol) and lithium hydroxide monohydrate (0.96 g, 23 mmol) in methanol/water (50 ml/50 ml) were stirred at room temperature for 18 hours then evaporated to dryness. The residue was partitioned between ethyl acetate and water (30 ml) containing sodium dihydrogen phosphate (7 g). The aqueous phase was further extracted with ethyl acetate and the combined extracts washed with brine, dried and evaporated to give a solid (5.0 g, 96%).

MS (+ve ion electrospray) m/z 274 (MH+).

(g) ((1R,2R,4R)-4-Carbamoyl-2-methoxy-cyclohexyl)-carbamic acid tert-butyl ester A solution of the acid (f) (5.0 g, 18 mmol) and 1-hydroxy-7-azabenzotriazole (2.73 g, 20 mmol) in DMF (200 ml) was treated with (3-dimethylamino-propyl)-ethyl-carbodiimide hydrochloride (3.87 g, 20 mmol) and ammonium hydrogen carbonate (5.8 g, 73 mmol). The mixture was stirred at room temperature for 18 hours then evaporated to dryness. The residue was partitioned between ethyl acetate and saturated aqueous sodium bicarbonate solution. The organic extract was dried and evaporated. Trituration with ether and filtration afforded a white solid (3.72 g, 75%).

MS (+ve ion electrospray) m/z 273 (MH+).

(h) [(1R,2R,4R)-2-Methoxy-4-(2-methyl-quinolin-8-ylcarbamoyl)-cyclohexyl]-carbamic acid tert-butyl ester This was prepared from triflate (18a) (110 mg, 0.37 mmol) and amide (g) (100 mg, 0.37 mmol) by the same procedure as for Example (18b) affording after chromatography a white solid (110 mg, 72%).

MS (+ve ion electrospray) m/z 414 (MH+).

(i) (1R,3R,4R)-4-Amino-3-methoxy-cyclohexanecarboxylic acid (2-methyl-quinolin-8-yl)-amide Carbamate (h) (110 mg, 0.27 mmol) was dissolved in dichloromethane/triluoroacetic acid (2 ml/2 ml). After 1 hour the mixture was evaporated to dryness and the residue triturated with ether. The residue was then redissolved in 10% methanol in dichloromethane (20 ml) and treated with macroporous triethylammonium methylpolystyrene carbonate resin (2.8 mmol/g; 2.7 g, Argonaut Technologies). After 1 hour the mixture was filtered and the resin washed several times alternately with 10% methanol in dichloromethane then methanol. The combined filtrate and washings were evaporated affording a white solid (80 mg, 95%).

MS (+ve ion electrospray) m/z 314 (MH+).

(j) Title Compound

The free base of the title compound was prepared in 63% yield from amine (39i) and aldehyde (35c) according to the general reductive alkylation procedure of Example (35d), affording a white solid after chromatography (76 mg).

$^1$H NMR δ (CDCl$_3$) 9.95 (1H, bs), 8.72 (1H, m), 8.12 (1H, s), 8.02 (1H, d), 7.45 (1H, d), 7.31 (1H, d), 6.85 (1H, s), 4.30 (4H, m), 3.90 (1H, d), 3.78 (1H, d), 3.40 (3H, s), 3.20 (1H, m), 2.75 (3H, s), 2.65-2.45 (2H, m), 2.25-2.05 (3H, m), 1.75-1.30 (3H, m).

MS (+ve ion electrospray) m/z 463 (MH+).

This material was converted into the dihydrochloride salt by the method of Example (1) affording the title compound as a white solid (85 mg).

Example 40

1-Hydroxy-t-4-[(3-oxo-3,4-dihydro-2H-pyrido[3,2-b][1,4]thiazin-6-ylmethyl)-amino]-r-cyclohexanecarboxylic acid (6-cyano-quinolin-4-yl)-amide dihydrochloride (cis-N-(6-cyano-4-quinolinyl)-1-hydroxy-4-{[(3-oxo-3,4-dihydro-2H-pyrido[3,2-b][1,4]thiazin-6-yl)methyl]amino}cyclohexanecarboxamide hydrochloride)

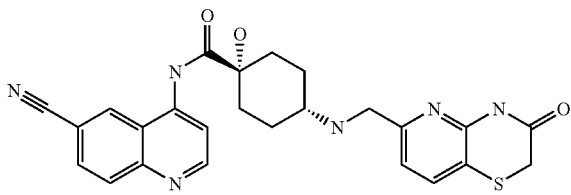

(a) 4-[(2,2-Dimethyl-4,6-dioxo-[1,3]dioxan-5-ylidenemethyl)-amino]-benzonitrile A mixture of 4-aminobenzonitrile (12.5 g, 0.106 mol), 2,2-dimethyl-[1,3]dioxane-4,6-dione (Meldrum's acid) (18.3 g, 0.127 mol) and triethyl orthoformate (16 ml) in ethanol (100 ml) was refluxed for 3 hours. After cooling to room temperature the product was filtered, washed with cold ethanol and air dried to afford an off-white solid (27.9 g, 97%).

MS (ES) m/e 273 (M+H)$^+$.

(b) 4-Oxo-1,4-dihydro-quinoline-6-carbonitrile

Benzonitrile (a) (27.5 g) was added portionwise over 5 minutes to refluxing Dowtherm A (200 ml). After refluxing an additional 5 minutes, the mixture was allowed to cool to room temperature and diluted with ether (200 ml) with stirring. The product was filtered off, washed thoroughly with ether and air dried to provide a gold solid (16.2 g, 94%).

MS (ES) m/e 171 (M+H)$^+$.

(c) 4-Bromo-quinoline-6-carbonitrile

A solution of quinolinone (b) (12.0 g, 70.5 mmol) in DMF (60 ml) was treated dropwise with phosphorus tribromide (8.0 ml, 84.6 mmol) over 10 minutes (exothermic). After allowing to stir and cool to room temperature, ice water (100 ml) was added and the mixture was stirred 30 minutes, then basified to pH8 by dropwise addition of 50% NaOH with cooling. The resultant solid was filterd off, washed with water and air dried to afford a tan solid (14.3 g, 87%).

MS (ES) m/e 234 (M+H)$^+$.

(d) [4-(6-Cyano-quinolin-4-ylcarbamoyl)-r-4-hydroxy-c-cyclohexyl]-carbamic acid tert butyl ester This was prepared from bromide (c) (350 mg, 1.5 mmol) and amide (1f) (387 mg, 1.5 mmol) by the same procedure as for Example (1l) affording after chromatography a white solid (580 mg, 94%).

MS (+ve ion electrospray) m/z 411 (MH$^+$).

(e) t-4-Amino-1-hydroxy-r-cyclohexanecarboxylic acid (6-cyano-quinolin-4-yl)-amide This was prepared from carbamate (d) (580 mg) by TFA deprotection and basic workup by the same procedure as Example (1m) affording a white solid (280 mg, 64%).

MS (+ve ion electrospray) m/z 311 (MH$^+$)

(f) Title Compound

A mixture of amine (e) (0.7 mmol) and aldehyde (1j)(136 mg, 0.7 mmol) in methanol/DMF/acetic acid (6 ml/6 ml/0.6 ml) was stirred at ambient temperature in the presence of 3 Å molecular sieves. After 2 hours sodium cyanoborohydride (88 mg, 1.4 mmol) was added and the mixture stirred overnight. The mixture was acidified with a few drops of 5M HCl then basified with saturated sodium hydrogen carbonate. The resulting precipitate was isolated by filtration and dried in vacuo. This was chromatographed on silica eluting with a gradient of 0-10% methanol in dichloromethane affording the free base of the title compound as a white solid (160 mg, 47%).

$^1$H NMR δ (DMSO) 10.80 (1H, bs), 10.35 (1H, bs), 8.95 (1H, d), 8.70 (1H, d), 8.12 (1H, d), 8.10-8.00 (2H, m), 7.75 (1H, d), 7.12 (1H, d), 4.00 (2H, s), 3.55 (2H, s), 2.50 (1H, m), 2.00-1.40 (8H, m).

MS (+ve ion electrospray) m/z 489 (MH$^+$).

This material was converted into the dihydrochloride salt by the method of Example (1) affording the title compound as a white solid (0.17 g).

Example 41 t-4[(2,3-Dihydro-[1,4]dioxino[2,3-c]pyridin-7-ylmethyl)-amino]-1-hydroxy-r-cyclohexanecarboxylic acid (3-methoxy-quinoxalin-5-yl)-amide hydrochloride (cis-4-[(2,3-dihydro[1,4]dioxino[2,3-c]pyridin-7-ylmethyl)amino]-1-hydroxy-N-[3-(methyloxy)-5-quinoxalinyl]cyclohexanecarboxamide hydrochloride)

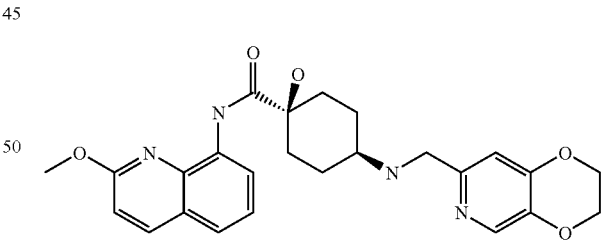

The free base of the title compound was prepared in 65% yield from amine (34h) and aldehyde (35c) according to the general reductive alkylation procedure of Example (35d), affording a white solid after chromatography (0.50 g).

$^1$H NMR δ (CDCl$_3$) 10.80 (1H, bs), 8.48 (1H, s), 8.08 (1H, s), 7.72 (1H, d), 7.53 (1H, t), 6.78 (1H, s), 4.30 (4H, m), 4.10 (3H, s), 3.85 (2H, s), 2.70 (1H, m), 2.25-1.50 (8H, m).

MS (+ve ion electrospray) m/z 466 (MH$^+$).

This material was converted into the hydrochloride salt by the method of Example (1) affording the title compound as a white solid (0.57 g).

Example 42 t-4-[(2,3-Dihydro[1,4]dioxino[2,3-c]pyridin-7-ylmethyl)amino]-1-hydroxy-N-(3-methyl-5-quinoxalinyl)-r-cyclohexanecarboxamide dihydrochloride(cis-4-[(2,3-dihydro[1,4]dioxino[2,3-c]pyridin-7-ylmethyl)amino]-1-hydroxy-N-(3-methyl-5-quinoxalinyl)cyclohexanecarboxamide hydrochloride)

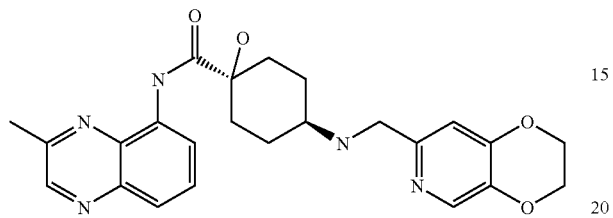

(a) Title Compound

A mixture of amine (25c) (0.24 mg, 0.75 mmol) and aldehyde (35c) (0.12 mg, 0.75 mmol) in DMF (7 ml) was treated with sodium triacetoxyborohydride (0.21 g, 1 mmol). After 18 hours the mixture was treated with more sodium triacetoxyborohydride (0.3 g) and stirred for a further 8 hours. The reaction mixture was diluted to 20 mL with water and an equal volume of saturated aqueous sodium bicarbonate solution was added. After cooling down to 4° C. for 1 hour, the precipitate formed was filtered, washed with water and dried in vacuo. The crude product was chromatographed on silica eluting with 2-10% methanol in dichloromethane affording the free base of the title compound as a white solid (160 mg, 47.5%).

$^1$H NMR δ (CDCl$_3$) 8.80-8.75 (2H, m), 8.1 (1H, s), 7.80-7.70 (2H, m), 6.79 (1H, s), 4.33-4.24 (4H, m), 3.84 (2H, s), 2.77 (3H, s), 2.65 (1H, m), 2.10 (2H, m), 2.00-1.80 (4H, m), 1.65 (2H, m).

MS (+ve ion electrospray) m/z 450 (MH+).

This material, as a solution in chloroform/methanol, was treated with an excess of 4M HCl in dioxan and evaporated to dryness. The solid was triturated under ether, filtered and dried under vacuum to provide the title compound.

Biological Activity

The MIC (μg/ml) of test compounds against various organisms was determined including:

*S. epidermidis* CL7, *S. aureus* WCUH29, *S. pneumoniae* 1629, *S. pyogenes* CN10, *H. influenzae* ATCC 49247, *E. faecalis* 2, *M. catarrhalis* Ravasio, *E. coli* 7623.

Examples 5, 7-22, 25, 26, 31, 32, 34, 37, 38, 40, 41 have an MIC≦2 μg/ml versus all these organisms Examples 1, 3, 6, 23, 27, 28, 35, 36, 42 have an MIC≦8 μg/ml versus all these organisms Examples 24, 29, 33, 39 have an MIC≦2 μg/ml versus some of these organisms Examples 2, 4, 30 has an MIC≦16 μg/ml versus at least one of these organisms

What is claimed is:

1. A compound selected from the compounds of formula (I); pharmaceutically acceptable salts of compounds of formula (I), and pharmaceutically acceptable N-oxides of compounds of formula (I), wherein formula (I) is:

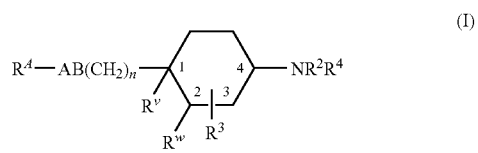

wherein:
R$^V$ and R$^W$ are hydrogen or R$^V$ and R$^W$ together are a bond;
R$^A$ is an optionally substituted bicyclic carbocyclic or heterocyclic ring system of structure:

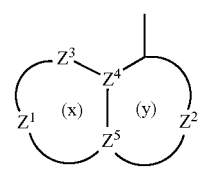

containing 0-3 heteroatoms in each ring in which:
at least one of rings (x) and (y) is aromatic;
one of Z$^4$ and Z$^5$ is C or N and the other is C;
Z$^3$ is N, NR$^{13}$, O, S(O)$_x$, CO, CR$^1$ or CR$^1$R$^{1a}$;
Z$^1$ and Z$^2$ are independently a 2 or 3 atom linker group each atom of which is independently selected from N, NR$^{13}$, O, S(O)$_x$, CO, CR$^1$ and CR$^1$R$^{1a}$; such that each ring is independently substituted with 0-3 groups R$^1$ and/or R$^{1a}$;
R$^1$ and R$^{1a}$ are independently selected from hydrogen; hydroxy; (C$_{1-6}$) alkoxy optionally substituted by (C$_{1-6}$) alkoxy, amino, piperidyl, guanidino or amidino any of which is optionally N-substituted by one or two (C$_{1-6}$) alkyl, acyl or (C$_{1-6}$)alkylsulphonyl groups, CONH$_2$, hydroxy, (C$_{1-6}$)alkylthio, heterocyclylthio, heterocyclyloxy, arylthio, aryloxy, acylthio, acyloxy or (C$_{1-6}$)alkylsulphonyloxy; (C$_{1-6}$)alkoxy-substituted (C$_{1-6}$)alkyl; hydroxy (C$_{1-6}$)alkyl; halogen; (C$_{1-6}$)alkyl; (C$_{1-6}$)alkylthio; trifluoromethyl; trifluoromethoxy; cyano; carboxy; nitro; azido; acyl; acyloxy; acylthio; (C$_{1-6}$)alkylsulphonyl; (C$_{1-6}$)alkylsulphoxide; arylsulphonyl; arylsulphoxide or an amino, piperidyl, guanidino or amidino group optionally N-substituted by one or two (C$_{1-6}$)alkyl, acyl or (C$_{1-6}$)alkylsulphonyl groups, or when Z$^3$ and the adjacent atom are CR$^1$ and CR$^{1a}$, R$^1$ and R$^{1a}$ may together represent (C$_{1-2}$)alkylenedioxy,
wherein acyl is (C$_{1-6}$)alkoxycarbonyl, formyl, or (C$_{1-6}$) alkylcarbonyl;
provided that R$^1$ and R$^{1a}$, on the same carbon atom are not both optionally substituted hydroxyl or amino;
provided that
(i) when R$^A$ is optionally substituted quinolin-4-yl:
it is unsubstituted in the 6-position; or
it is substituted by at least one hydroxy (C$_{1-6}$)alkyl, cyano or carboxy group at the 2-, 5-, 6-, 7- or 8-position; or
it is substituted by at least one trifluoromethoxy group; or
R$^3$ is halogen;
(ii) when R$^A$ is optionally substituted quinazolin-4-yl, cinnolin-4-yl, 1,5-naphthyridin-4-yl, 1,7-naphthyridin-4-yl or 1,8-naphthyridin-4-yl:

it is substituted by at least one hydroxy $(C_{1-6})$alkyl, cyano or carboxy group at the 2-, 5-, 6-, 7- or 8-position as available; or it is substituted by at least one trifluoromethoxy group; or $R^3$ is halogen;

$R^2$ is hydrogen, or $(C_{1-4})$alkyl or $(C_{2-4})$alkenyl optionally substituted with 1 to 3 groups selected from:

amino optionally substituted by one or two $(C_{1-4})$alkyl groups; carboxy; $(C_{1-4})$alkoxycarbonyl; $(C_{1-4})$alkylcarbonyl; $(C_{2-4})$alkenyloxycarbonyl; $(C_{2-4})$alkenylcarbonyl; aminocarbonyl wherein the amino group is optionally substituted by hydroxy, $(C_{1-4})$alkyl, hydroxy$(C_{1-4})$alkyl, aminocarbonyl$(C_{1-4})$alkyl, $(C_{2-4})$alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$alkenyloxycarbonyl or $(C_{2-4})$alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; halogen; $(C_{1-4})$alkylthio; trifluoromethyl; hydroxy optionally substituted by $(C_{1-4})$alkyl, $(C_{2-4})$alkenyl, $(C_{1-4})$alkoxycarbonyl, $(C_{1-4})$alkylcarbonyl, $(C_{2-4})$alkenyloxycarbonyl, $(C_{2-4})$alkenylcarbonyl; oxo; $(C_{1-4})$alkylsulphonyl; $(C_{2-4})$alkenylsulphonyl; or $(C_{1-4})$aminosulphonyl wherein the amino group is optionally substituted by $(C_{1-4})$alkyl or $(C_{2-4})$alkenyl;

$R^3$ is hydrogen; or when $R^V$ and $R^W$ are a bond, $R^3$ is in the 2-, 3- or 4-position and when $R^v$ and $R^w$ are not a bond, $R^3$ is in the 1-, 2-, 3- or 4-position and $R^3$ is:

carboxy; $(C_{1-6})$alkoxycarbonyl; aminocarbonyl wherein the amino group is optionally substituted by hydroxy, $(C_{1-6})$alkyl, hydroxy$(C_{1-6})$alkyl, aminocarbonyl$(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $(C_{1-4})$alkyl or ethenyl optionally substituted with any of the groups listed above for $R^3$ and/or 0 to 2 groups $R^{12}$ independently selected from:

halogen; $(C_{1-6})$alkylthio; trifluoromethyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy$(C_{1-6})$alkyl, aminocarbonyl$(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl; or hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; or amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; or halogen;

provided that when $R^3$ is in the 4-position it is not optionally substituted hydroxyl or amino or halogen;

in addition when $R^3$ is disubstituted with a hydroxy or amino containing substituent and a carboxy containing substituent these may optionally together form a cyclic ester or amide linkage, respectively;

$R^{10}$ is selected from $(C_{1-4})$alkyl and $(C_{2-4})$alkenyl either of which may be optionally substituted by a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; $(C_{1-6})$alkylsulphonyl; trifluoromethylsulphonyl; $(C_{2-6})$alkenylsulphonyl; $(C_{1-6})$alkoxycarbonyl; $(C_{1-6})$alkylcarbonyl; $(C_{2-6})$alkenyloxycarbonyl; and $(C_{2-6})$alkenylcarbonyl;

$R^4$ is a group —U—$R^5{}_2$ where $R^5{}_2$ is a group,

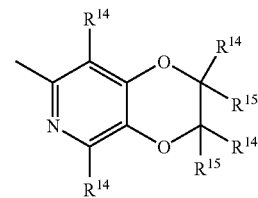

each of $R^{14}$ and $R^{15}$ is independently selected from: H; $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; aryl; aryl$(C_{1-4})$alkyl; aryl$(C_{1-4})$alkoxy;

each $R^{13}$ is independently H; trifluoromethyl; $(C_{1-4})$alkyl optionally substituted by hydroxy, carboxy, $(C_{1-6})$ alkoxycarbonyl, $(C_{1-6})$alkoxy, $(C_{1-6})$alkylthio, halo or trifluoromethyl; $(C_{2-4})$alkenyl; aryl; aryl $(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl;

each x is independently 0, 1 or 2;

U is CO, $SO_2$ or $CH_2$;

n is 0 or 1 and AB is $NR^{11}CO$, $CONR^{11}$, $CO-CR^8R^9$, $CR^6R^7-CO$, $O-CR^8R^9$, $CR^6R^7-O$, $NHR^{11}-CR^8R^9$, $CR^6R^7-NHR^{11}$, $NR^{11}SO_2$, $CR^6R^7-SO_2$ or $CR^6R^7-CR^8R^9$, provided that when $R^v$ and $R^w$ are a bond and n=0, B is not $NR^{11}$, O or $SO_2$, or n is 0 and AB is NH—CO—NH or NH—CO—O and $R^V/R^W$ are not a bond;

or n is 0 and AB is $CR^6R^7SO_2NR^2$, $CR^6R^7CONR^2$ or $CR^6R^7CH_2NR^2$ and $R^V/R^W$ are not a bond;

provided that $R^6$ and $R^7$, and $R^8$ and $R^9$ are not both optionally substituted hydroxy or amino;

and wherein:

each of $R^6$, $R^7$, $R^8$ and $R^9$ is independently selected from: H; $(C_{1-6})$alkoxy; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl;

or $R^6$ and $R^8$ together represent a bond and $R^7$ and $R^9$ are as above defined;

and each $R^{11}$ is independently H; trifluoromethyl; $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl;

or where one of $R^3$ and $R^6$, $R^7$, $R^8$ or $R^9$ contains a hydroxy or amino group they may together form a cyclic ester or amide linkage or where $R^3$ contains a carboxy group and A or B is NH they may be condensed to form a cyclic amide.

2. The compound according to claim 1 wherein $R^4$ is optionally substituted isoquinolin-5-yl, quinolin-8-yl, thieno[3,2-b]pyridin-7-yl, 2,3-dihydro-[1,4]dioxino[2,3-b]pyridin-8-yl, quinoxalin-5-yl, isoquinolin-8-yl, [1,6]-naphthyridin-4-yl, 1,2,3,4-tetrahydroquinoxalin-5-yl or 1,2-dihydroisoquinoline-8-yl.

3. The compound according to claim 1 wherein $R^1$ is hydrogen, methoxy, methyl, cyano or halogen and $R^{1a}$ is H.

4. The compound according to claim 1 wherein $R^2$ is hydrogen.

5. The compound according to claim 1 wherein $R^3$ is hydrogen, fluoro or hydroxy substituted in the 1-or 3-position.

6. The compound according to claim 1 wherein n is 0 and either A and B are both $CH_2$, A is CHOH or $CH_2$ and B is $CH_2$ or A is NH and B is CO.

7. The compound according to claim 1 wherein $R^5_2$ is 2,3-dihydro-[1,4]dioxino[2,3-c]pyridin-7-yl.

8. A compound selected from:

Cis-4-[(2,3-dihydro[1,4]dioxino[2,3-c]pyridin-7-ylmethyl)amino]-1-hydroxy-N-(2-methyl-8-quinolinyl)cyclohexanecarboxamide;

trans-4-[(2,3-dihydro[1,4]dioxino[2,3-c]pyridin-7-ylmethyl)amino]-N-(2-methyl-8-quinolinyl)cyclohexanecarboxamide;

(1R,3S,4R)-N-(2-cyano-8-quinolinyl)-4-[(2,3-dihydro[1,4]dioxino[2,3-c]pyridin-7-ylmethyl)amino]-3-hydroxycyclohexanecarboxamide;

cis-N-(2-cyano-8-quinolinyl)-4-[(2,3-dihydro[1,4]dioxino[2,3-c]pyridin-7-ylmethyl)amino]-1-hydroxycyclohexanecarboxamide;

(1R3R4R)-4-[(2,3-dihydro[1,4]dioxino[2,3-c]pyridin-7-ylmethyl)amino]-3-(methyloxy)-N-(2-methyl-8-quinolinyl)cyclohexanecarboxamide;

cis-4-[(2,3-dihydro[1,4]dioxino[2,3-c]pyridin-7-ylmethyl)amino]-1-hydroxy-N-[3-(methyloxy-5-quinoxalinyl]cyclohexanecarboxamide;

cis-4-[(2,3-dihydro[1,4]dioxino[2,3-c]pyridin-7-ylmethyl)amino]-1-hydroxy-N-(3-methyl-5-quinoxalinyl)cyclohexanecarboxamide;

pharmaceutically acceptable salts of the foregoing compounds; and pharmaceutically acceptable N-oxides of the foregoing compounds.

9. A method of treatment of bacterial infection due to *Staphylococcus aureus, Staphylococcus epidermidis, Streptococcus pneumoniae, Streptococcus pyogenes, Enterococcus faecalis, Haemophilus influenzae, E. coli,* or *Moraxella catarrhalis* in mammals, which method comprises the administration to a mammal in need of such treatment an effective amount of the compound according to claim 1.

10. A pharmaceutical composition comprising the compound according to claim 1, and a pharmaceutically acceptable carrier.

11. A process for preparing a compound according to claim 1, which process comprises reacting a compound of formula (IV) with a compound of formula (V):

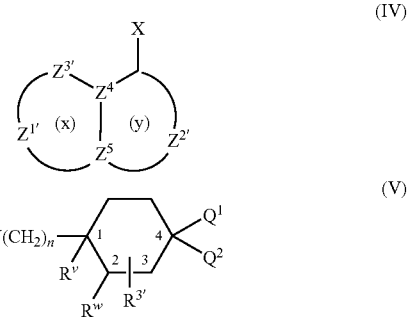

wherein n is as defined in formula (I); $Z^{1'}$, $Z^{2'}$, $Z^{3'}R^{1'}$ and $R^{3'}$ are $Z^1$, $Z^2$, $Z^3$, $R^1$ and $R^3$ as defined in formula (I) or groups convertible thereto; $Z^4$, $Z^5$, $R^v$ and $R^w$ are as defined in formula (I);

$Q^1$ is $NR^{2'}R^{4'}$ or a group convertible thereto wherein $R^{2'}$ and $R^{4'}$ are $R^2$ and $R^4$ as defined in formula (I) or groups convertible thereto and $Q^2$ is H or $R^{3'}$ or $Q^1$ and $Q^2$ together form an optionally protected oxo group;

and X and Y may be the following combinations:

(i) one of X and Y is $CO_2R^y$ and the other is $CH_2CO_2R^x$;

(ii) X is $CHR^6R^7$ and Y is $C(=O)R^9$;

(iii) X is $CR^7=PR^z_3$ and Y is $C(=O)R^9$;

(iv) X is C(=O)R$^7$ and Y is CR$^9$=PR$^z{}_3$;
(v) one of Y and X is COW and the other is NHR$^{11'}$, NCO or NR$^{11'}$COW;
(vi) X is NHR$^{11}$ and Y is C(=O)R$^8$ or X is C(=O)R$^6$ and Y is NHR$^{11'}$;
(vii) X is NHR$^{11'}$ and Y is CR$^8$R$^9$;
(viii) X is W or OH and Y is CH$_2$OH;
(ix) X is NHR$^{11'}$ and Y is SO$_2$W;
(x) one of X and Y is (CH$_2$)$_p$—W and the other is (CH$_2$)$_q$NHR$^{11'}$, (CH$_2$)$_q$OH, (CH$_2$)$_q$SH or (CH$_2$)$_q$SCOR$^x$ where p+q=1;
(xi) one of X and Y is OH and the other is —CH=N$_2$;
(xii) X is NCO and Y is OH or NH$_2$;
(xiii) X is CR$^6$R$^7$SO$_2$W, A'COW, CR$^6$=CH$_2$ or oxirane and Y is NHR$^{2'}$;
(xiv) X is W and Y is CONHR$^{11}$ or OCONH$_2$
(xv) X is W and Y is —C≡CH followed by hydrogenation of the intermediate —C=C— group;
in which W is a leaving group; R$^x$ and R$^y$ are (C$_{1-6}$)alkyl; R$^z$ is aryl or (C$_{1-6}$)alkyl; A' and NR$^{11'}$ are A and NR$^{11}$ as defined in formula (I), or groups convertible thereto; and oxirane is:

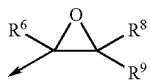

wherein R$^6$, R$^8$ and R$^9$ are as defined in formula (I);
and thereafter optionally or as necessary converting Q$^1$ and Q$^2$ to NR$^2$R$^{4'}$; converting A', Z$^{1'}$, Z$^{2'}$, Z$^{3'}$, R$^{1'}$, R$^{2'}$, R$^{3'}$, R$^{4'}$ and NR$^{11'}$ to A, Z$^1$, Z$^2$, Z$^3$, R$^1$, R$^2$, R$^3$, R$^4$ and NR$^{11'}$; converting A-B to other A-B, interconverting R$^v$, R$^w$, R$^1$, R$^2$, R$^3$ and/or R$^4$, and/or forming a pharmaceutically acceptable derivative thereof.

12. A method of treatment of bacterial infection due to *Staphylococcus aureus, Staphylococcus epidermidis, Streptococcus pneumoniae, Streptococcus pyogenes, Enterococcus faecalis, Haemophilus influenzae, E. coli,* or *Moraxella catarrhalis* in mammals, which method comprises the administration to a mammal in need of such treatment an effective amount of the compound according to claim 8.

13. A pharmaceutical composition comprising the compound according to claim 8, and a pharmaceutically acceptable carrier.

14. The compound according to claim 1 wherein R$^A$ is 2-methyl-1-oxo-1,2-dihydro-isoquinolin-8yl.

15. The compound according to claim 1 wherein R$^A$ is 3-methoxy-quinoxalin-5-yl.

16. The compound according to claim 1 wherein the compound is a compound of formula (I).

17. A method of treatment of bacterial infection due to *Staphylococcus aureus, Staphylococcus epidermidis, Streptococcus pneumoniae, Streptococcus pyogenes, Enterococcus faecalis, Haemophilus influenzae, E. coli,* or *Moraxella catarrhalis* in mammals, which method comprises the administration to a mammal in need of such treatment an effective amount of the compound according to claim 16.

18. A pharmaceutical composition comprising the compound according to claim 16, and a pharmaceutically acceptable carrier.

19. The compound according to claim 1 wherein the compound is a pharmaceutically acceptable salt of a compound of formula (I).

20. A method of treatment of bacterial infection due to *Staphylococcus aureus, Staphylococcus epidermidis, Streptococcus pneumoniae, Streptococcus pyogenes, Enterococcus faecalis, Haemophilus influenzae, E. coli,* or *Moraxella catarrhalis* in mammals, which method comprises the administration to a mammal in need of such treatment an effective amount of the compound according to claim 19.

21. A pharmaceutical composition comprising the compound according to claim 19, and a pharmaceutically acceptable carrier.

22. A compound selected from:
Cis-4-[(2,3-dihydro[1,4]dioxino[2,3-c]pyridin-7-ylmethyl)amino]-1-hydroxy-N-(2-methyl-8-quinolinyl)cyclohexanecarboxamide hydrochloride;
trans-4-[(2,3-dihydro[1,4]dioxino[2,3-c]pyridin-7-ylmethyl)amino]-N-(2-methyl-8-quinolinyl)cyclohexanecarboxamide hydrochloride;
(1R,3S,4R)-N-(2-cyano-8-quinolinyl)-4-[(2,3-dihydro[1,4]dioxino[2,3-c]pyridin-7-ylmethyl)amino]-3-hydroxycyclohexanecarboxamide hydrochloride;
cis-N-(2-cyano-8-quinolinyl)-4-[(2,3-dihydro[1,4]dioxino[2,3-c]pyridin-7-ylmethyl)amino]-1-hydroxycyclohexanecarboxamide hydrochloride;
(1R3R4R)-4-[(2,3-dihydro[1,4]dioxino[2,3-c]pyridin-7-ylmethyl)amino]-3-(methyloxy)-N-(2-methyl-8-quinolinyl)cyclohexanecarboxamide hydrochloride;
cis-4-[(2,3-dihydro[1,4]dioxino[2,3-c]pyridin-7-ylmethyl)amino]-1-hydroxy-N-[3-(methyloxy-5-quinoxalinyl]cyclohexanecarboxamide hydrochloride;
cis-4-[(2,3-dihydro[1,4]dioxino[2,3-c]pyridin-7-ylmethyl)amino]-1-hydroxy-N-(3-methyl-5-quinoxalinyl)cyclohexanecarboxamide hydrochloride.

23. A method of treatment of bacterial infection due to *Staphylococcus aureus, Staphylococcus epidermidis, Streptococcus pneumoniae, Streptococcus pyogenes, Enterococcus faecalis, Haemophilus influenzae, E. coli,* or *Moraxella catarrhalis* in mammals, which method comprises the administration to a mammal in need of such treatment an effective amount of the compound according to claim 22.

24. A pharmaceutical composition comprising the compound according to claim 22, and a pharmaceutically acceptable carrier.

* * * * *